(12) United States Patent
Cohen et al.

(10) Patent No.: US 7,332,480 B2
(45) Date of Patent: *Feb. 19, 2008

(54) COMPOSITIONS FOR THE REGULATION OF CYTOKINE ACTIVITY

(75) Inventors: Irun R. Cohen, Rehovot (IL); Ofer Lider, Rehovot (IL); Liora Cahalon, Givataim (IL); Oded Shoseyov, Shimshon (IL); Raanan Margalit, Rehovot (IL)

(73) Assignee: Yeda Research and Development Co. Ltd., Rechovot (IL)

( * ) Notice: Subject to any disclaimer, the term of this patent is extended or adjusted under 35 U.S.C. 154(b) by 225 days.

This patent is subject to a terminal disclaimer.

(21) Appl. No.: 10/831,288

(22) Filed: Apr. 26, 2004

(65) Prior Publication Data

US 2004/0198697 A1    Oct. 7, 2004

Related U.S. Application Data

(60) Division of application No. 09/495,723, filed on Feb. 1, 2000, now Pat. No. 6,750,207, which is a division of application No. 08/486,127, filed on Jun. 7, 1995, now Pat. No. 6,020,323, which is a continuation-in-part of application No. 08/436,330, filed as application No. PCT/US93/10868 on Nov. 9, 1993, now Pat. No. 5,861,382, which is a continuation-in-part of application No. 08/096,739, filed on Jul. 23, 1993, now abandoned, which is a continuation-in-part of application No. 07/974,750, filed on Nov. 10, 1992, now abandoned, which is a continuation-in-part of application No. 07/878,188, filed on May 1, 1992, now abandoned.

(51) Int. Cl.
*A61K 31/7016* (2006.01)
*A61K 31/727* (2006.01)
*C08B 37/10* (2006.01)

(52) U.S. Cl. .................. 514/53; 514/56; 536/21; 536/123.13

(58) Field of Classification Search ............. 514/53, 514/54, 56, 61
See application file for complete search history.

(56) References Cited

U.S. PATENT DOCUMENTS

| | | | |
|---|---|---|---|
| 1,950,100 A * | 3/1934 | Crandall, Jr. .............. 514/54 |
| 4,401,662 A | 8/1983 | Lormeau et al. |
| 4,446,314 A | 5/1984 | Jordan |
| 4,468,385 A * | 8/1984 | Callahan et al. ............ 514/24 |
| 4,539,398 A | 9/1985 | Rosenberg |
| 4,607,025 A | 8/1986 | Petitou et al. |
| 4,727,063 A | 2/1988 | Naggi et al. |
| 4,774,231 A | 9/1988 | Petitou et al. |
| 4,801,583 A | 1/1989 | Petitou et al. |
| 4,818,816 A | 4/1989 | Petitou et al. |
| 4,882,318 A | 11/1989 | Vlodavsky et al. |
| 4,889,808 A | 12/1989 | Rappaport |
| 4,933,326 A | 6/1990 | Bianchini et al. |
| 4,943,630 A | 7/1990 | Jacquinet et al. |
| 4,973,580 A | 11/1990 | Mascellani et al. |
| 4,981,955 A | 1/1991 | Lopez |
| 4,987,223 A | 1/1991 | Choay et al. |
| 4,990,502 A | 2/1991 | Lormeau et al. |
| 5,010,063 A | 4/1991 | Piani et al. |
| 5,034,520 A | 7/1991 | Lormeau et al. |
| 5,474,987 A | 12/1995 | Cohen et al. |
| 5,580,858 A * | 12/1996 | Ippolito et al. ............. 514/25 |
| 5,686,431 A | 11/1997 | Cohen et al. |
| 5,861,382 A | 1/1999 | Cohen et al. |
| 5,908,837 A | 6/1999 | Cohen et al. |
| 6,020,323 A | 2/2000 | Cohen et al. |
| 6,750,207 B1 | 6/2004 | Cohen et al. |
| 2003/0130230 A1 | 7/2003 | Cahalon et al. |
| 2004/0198697 A1 | 10/2004 | Cohen et al. |

FOREIGN PATENT DOCUMENTS

| | | |
|---|---|---|
| EP | 0114589 | 1/1984 |
| EP | 0375976 | 4/1990 |
| EP | 0394971 | 10/1990 |
| EP | 0669827 | 5/2001 |
| JP | 08092104 | * 9/1994 |
| WO | WO 88/05301 | 7/1988 |
| WO | WO89/05645 | * 6/1989 |
| WO | WO 90/03791 | 4/1990 |
| WO | WO93/24506 | * 12/1993 |
| WO | WO 94/11006 | 5/1994 |
| WO | WO01/72762 | * 10/2001 |
| WO | WO 03/047501 | 6/2003 |

OTHER PUBLICATIONS

S. A. Riley et al. "A Comparison of Sucralfate and Prednisone Enemas in the Treatment of Active Distal Ulcerative Colitis" (1989) The Scandinavian Journal of Gastroenterology, vol. 24, No. 8, pp. 1014-1018.*

(Continued)

*Primary Examiner*—Shaojia Anna Jiang
*Assistant Examiner*—Eric S Olson

(57) ABSTRACT

Substances comprising carboxylated and/or sulfated oligosaccharides in substantially purified form, including compositions containing same and methods of using same, are disclosed for the regulation of cytokine activity in a host. For instance, the secretion of Tumor Necrosis Factor Alpha (TNF-α) can be either inhibited or augmented selectively by administration to the host of effective amounts of substances or their compositions comprising specific oligosaccharides in substantially purified form. Thus, the present invention also relates to pharmaceutical compositions and their use for the prevention and/or treatment of pathological processes involving the induction of active cytokine secretion, such as TNF-α. The invention also relates to the initiation of a desirable immune system-related response by the host to the presence of activators, including pathogens. The substances and pharmaceutical compositions of the present invention may be daily, at very low effective doses, typically below 0.1 mg/kg human, or at intervals of up to about 5-8 days, preferably once a week.

19 Claims, 54 Drawing Sheets

OTHER PUBLICATIONS

Basic and Clinical Immunology, 1984, Published by Lange Medical Publications, edited by Daniel P. Sites et al., Chapter 12 pp. 152-186.*

The Merck Manual of Diagnosis and Therapy, seventeenth edition, 1999, Published by Merck Research Laboratories, pp. 426-430, 872-875.*

Shlomchik et al. "The Role of B Cells in lpr/lpr-induced Autoimmunity" Journal of Experimental Medicine (1994) vol. 180, pp. 1295-1306.*

Smith et al., "Neutralization of Endogenous Tumor Necrosis Factor Ameliorates the Severity of Myosin-Induced Myocarditis" Circulation Research (1992) vol. 70, No. 4, pp. 856-863.*

Broekhutse et al., "Experimental Autoimmune Anterior Uveitis (EAAU). III. Induction by Immunization with Purified Uveal and Skin Melanins" Experimental Eye Research (1993) vol. 56, pp. 575-583.*

Timar et al. "Interactions of Exogenous Heparan Sulfate with Tumor Cells of Different Metastatic Phenotype", Invasion Metastasis, 10: 301-315, 1990.

Vlodavsky et al. "Modulation of Neovascularization and Metastasis by Species of Heparin", Adv. Exp. Med. Biol., 13: 317-327, 1992.

Hershkoviz et al. "Disaccharides Generated From Heparan Sulphate or Heparin Modulate Chemokine-Induced T-Cell Adhesion to Extracellular Matrix", Immunology, 99: 87-93, 2000.

Lider et al. "A Disaccharide That Inhibits Tumor Necrosis Factor ALPHA Is Formed From the Extracellular Matrix by the Enzyme Heparanase", Proc. Natl. Acad. Sci. USA, 92: 5037-5041, 1995.

Cahalon et al. "Heparin Disaccharides Inhibit Tumor Necrosis Factor-Alpha Production by Macrophages and Arrest Immune Inflammation in Rodents", Internat. Immunology, 9(10): 1517-1522, 1997.

Horvath et al. "Low Dose Heparin and Early Kidney Transplant Function", Aust. N.Z. J. Med., 5: 537-539, 1975.

Kariya et al. "Preparation of Unsaturated Disaccharides by Eliminative Cleavage of Heparin and Heparan Sulfate With Heparitinases", Comp. Biochem. Physiol., 103B: 473-479, 1992.

Lider et al. "Inhibition of T Lymphocyte Heparanase by Heparin Prevents T Cell Migration and T Cell-Mediated Immunity", Eur. J. Immunol., 20: 493-499, 1990.

Lider et al. "Suppression of Experimental Autoimmune Diseases and Prolongation of Allograft Survival by Treatment of Animals With Low Doses of Heparins", J. Clin. Invest., 83: 752-756, 1989.

Neparstek et al. "Activated T Lymphocytes Produce A Matrix-Degrading Heparan Sulphate Endoglycosidase", Nature, 310: 241-244, 1984.

Psuja "Affinity of Binding of Radiolabeled (125 I) Heparin and Low Molecular Weight Heparin Fraction CY 222 to Endothelium in Culture", Folio Haematol., 114(3): 429-436, 1987.

Toivonen et al. "Rat Adjuvant Arthritis as A Model to Test Potential Antirheumatic Agents", Meth. and Find. Exptl. Clin. Pharmacol., 4(6): 359-363, 1982.

Asselot et al. "Heparin Fragments Regulate Collagen Phenotype and Fibronectin Synthesis in the Skin of Genetically Diabetic Mice", Biochem. Pharmacol., 38: 895-899, 1989.

Asselot-Chapel et al. "Biosyntheses of Intersitial Collagens and Fibronectin by Porcine Aorta Smooth Muscle Cells. Modulation by Low-Molecular-Weight Heparin Fragments", Biochim. Biophys. Acta, 993: 240-244, 1989.

Rodén et al. "Heparin—An Introduction", Heparin and Related Polysaccharides, Plenum Press, p. 1-20, 1992.

Bezouška et al. "Oligosaccharide Ligands for NKR-P1 Protein Activate NK Cells and Cytotoxicity", Nature, 372: 150-157, 1994.

Grant "Oligosaccharide", Grant & Hackh's Chemical Dictionary, 5 Ed.: 409, 1987.

The Merck Manuel of Diagnosis and Therapy seventeenth edition, 1999, Published by Merck Research Laboratories, pp. 426-430 and 872-875.

Venkataraman et al. "Sequencing Complex Polysaccharides", Science, 286: 537-542, 1999.

Müller et al. "Involvement of Chemokine Receptors in Breast Cancer Metastasis", Nature, 410: 50-56, 2001.

Sehgal et al. "Molecular Characterization of CXCR-4: A Potential Brain Tumor-Associated Gene", Journal of Surgical Oncology, 69: 239-248, 1998.

Sehgal et al. "CXCR-4, A Chemokine Receptor, Is Overexpressed in and Required for Proliferation of Glioblastoma Tumor Cells", Journal of Surgical Oncology, 69: 99-104, 1998.

Rossi et al. "The Biology of Chemokines and Receptors", Annu. Rev. Immunol., 18: 217-242, 2000.

Braun et al. "The CC Chemokine CKβ-11/MIP-3β/ELC/Exodus 3 Mediates Tumor Rejection of Murine Breast Cancer Cells Through NK Cells", The Journal of Immunology, 164: 4025-4031, 2000.

Bleul et al. "The Lymphocyte Chemoattractant SDF-1 Is A Ligand for LESTR/Fusin and Blocks HIV-1 Entry", Nature, 382: 829-833, 1996.

Murdoch et al. "Chemokine Receptors and Their Role in Inflammation and Infectious Diseases", Blood, 95(10): 3032-3043, 2000.

Oberlin et al. "The CXC Chemokine SDF-1 Is the Ligand for LESTR/Fusin and Prevents Infection by T-Cell-Line-Adapted HIV-1", Nature, 382: 833-835, 1996.

Nagasawa et al. "Defects of B-Cell Lymphopoiesis and Bone-Marrow Myelopoiesis in Mice Lacking the CXC Chemokine PBSF/SDF-1", Nature, 382: 635-638, 1996.

McGrath et al. "Embryonic Expression and Function of the Chemokine SDF-1 and Its Receptor, CXCR4", Developmental Biology, 213: 442-456, 1999.

Ponomaryov et al. "Induction of the Chemokine Stromal-Derived Factor-1 Following DNA Damage Improves Human Stem Cell Function", The Journal of Clinical Investigation, 106(11): 1331-1339, 2000.

Gonzalo et al. "Critical Involvement of the Chemotactic Axis CXCR4/Stromal Cell-Derived Factor-1α in the Inflammatory Component of Allergic Airway Disease", The Journal of Immunology, 165: 499-508, 2000.

Peled et al. "The Chemokine SDF-1 Stimulates Integrin-Mediated Arrest of CD34+ Cells on Vascular Endothelium Under Shear Flow", The Journal of Clinical Investigation, 104(9): 1199-1211, 1999.

Peled et al. "Dependence of Human Stem Cell Engraftment and Repopulation of NOD/SCID Mice on CXCR4", Science, 283: 845-848, 1999.

Sawada et al. "Disturbed CD4+ T Cell Homeostasis and In Vitro HIV-1 Susceptibility in Transgenic Mice Expressing T Cell Line-Tropic HIV-1 Receptors", Journal of Experimental Medicine, 187(9): 1439-1449, 1998.

Aiuti et al. "The Chemokine SDF-1 Is A Chemoattractant for Human CD34+ Hematpoietic Progenitor Cells and Provides A New Mechanism to Explain the Mobilization of CD34+ Progenitors to Peripheral Blood", Journal of Experimental Medicine, 185(1): 111-120, 1997.

Peled et al. "The Chemokine SDF-1 Activates the Integrins LFA-1, VLA-4, and VLA-5 on Immature Human CD34+ Cells: Role in Transendothelial/Stromal Migration and Engraftment of NOD/SCID Mice", Blood, 95(11): 3289-3296, 2000.

Edinger et al. "Noninvasive Assessment of Tumor Cell Proliferation in Animal Models", Neoplasia, 1(4): 303-310, 1999.

Contag et al. "Bioluminescent Indicators in Living Mammals", Nature Medicine, 4(2): 245-247, 1998.

Condiotti et al. "Effect of Interleukin-12 on Antitumor Activity of Human Umbilical Cord Blood and Bone Marrow Cytotoxic Cells", Experimental Hematology, 26: 571-579, 1998.

Chowers et al. "Disaccharides Derived From Heparin or Heparan Sulfate Regulate IL-8 and IL-1β Secretion by Intestinal Epithelial Cells", Gastroenterology, 120: 449-459, 2001.

Goodman et al. "Anticoagulant, Thrombolytic, and Antiplatelet Drugs", The Pharmacological Basis of Theapeutics, II(Chap.55): 1312-1315, 1992.

* cited by examiner

FIG. 5

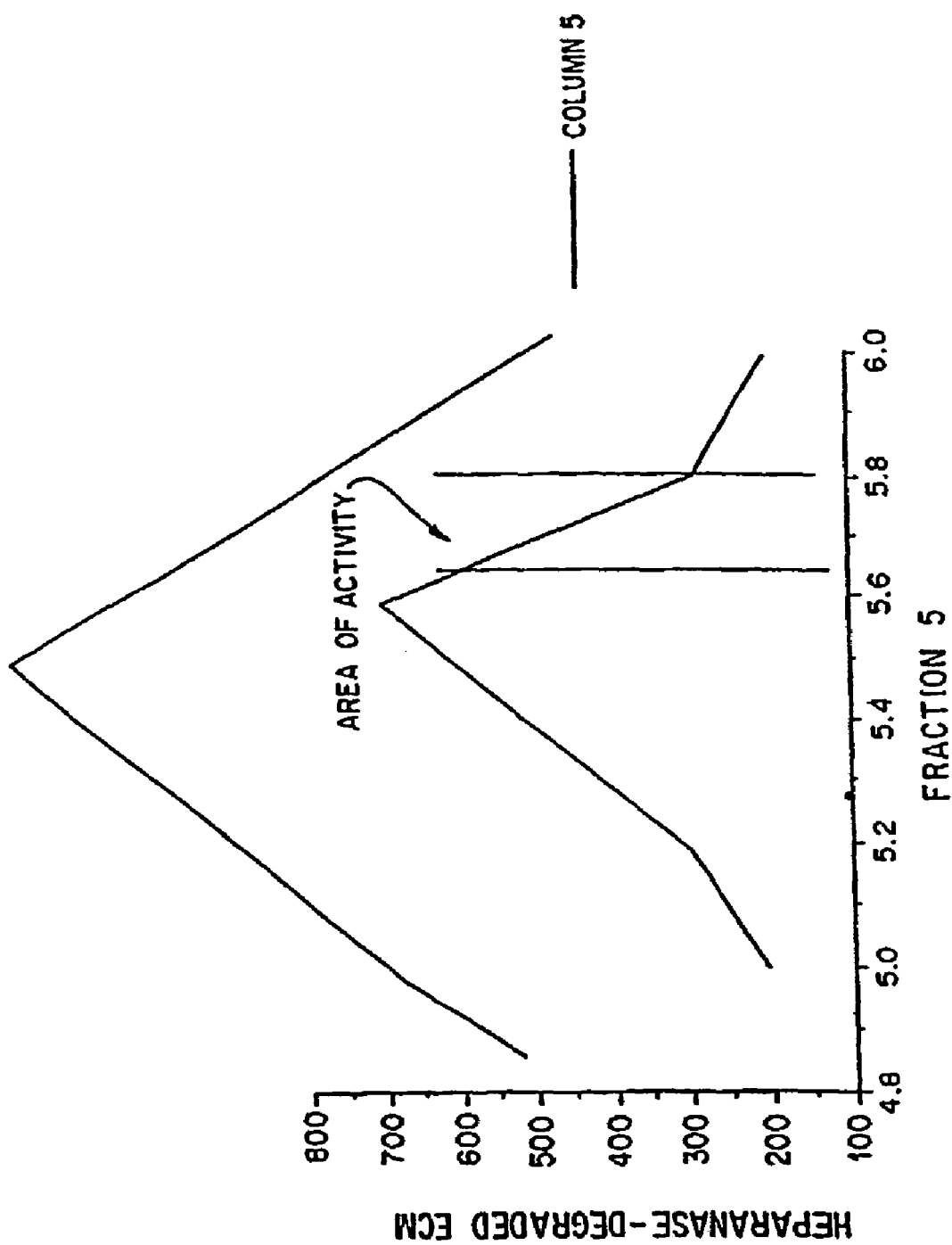

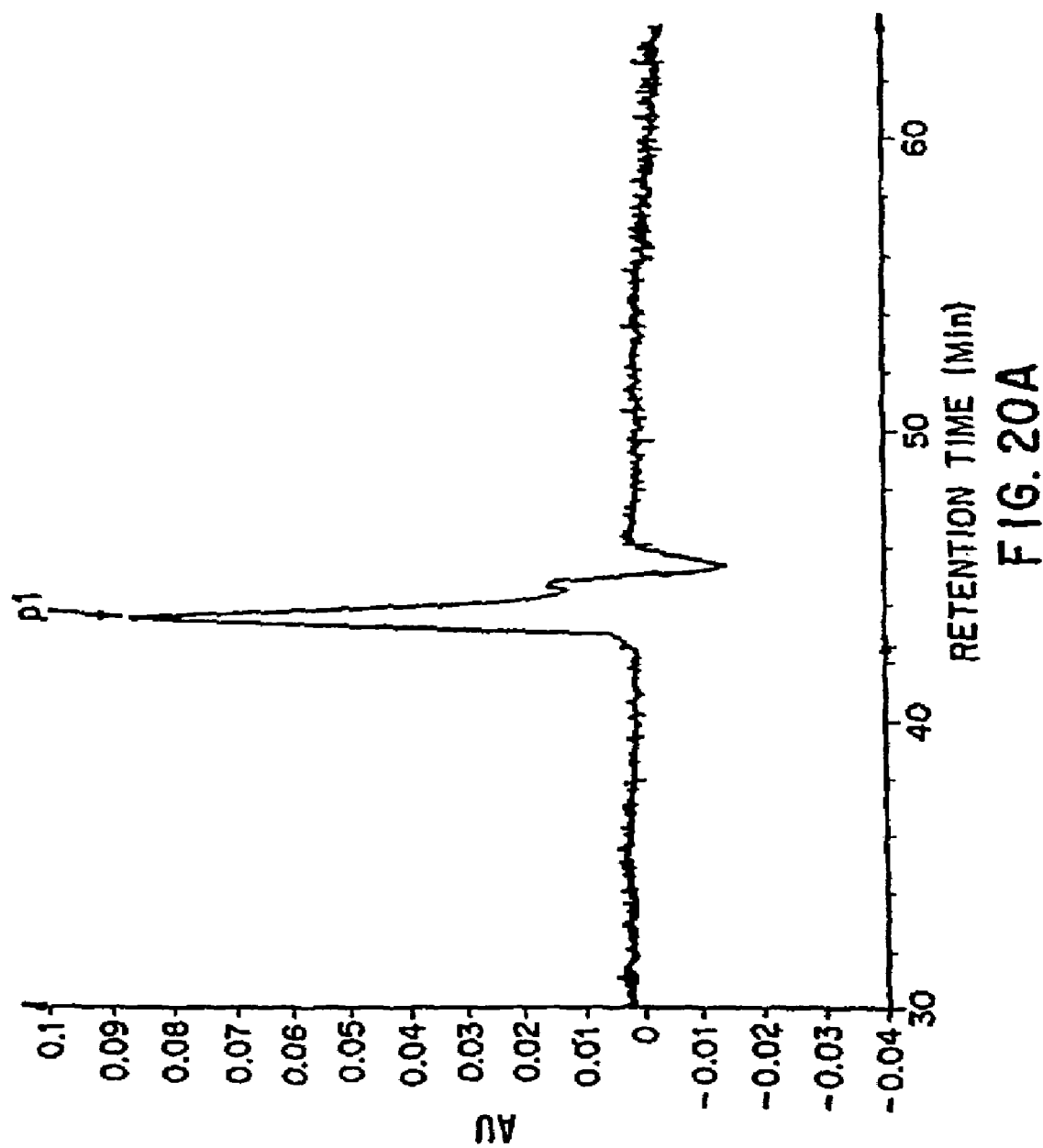

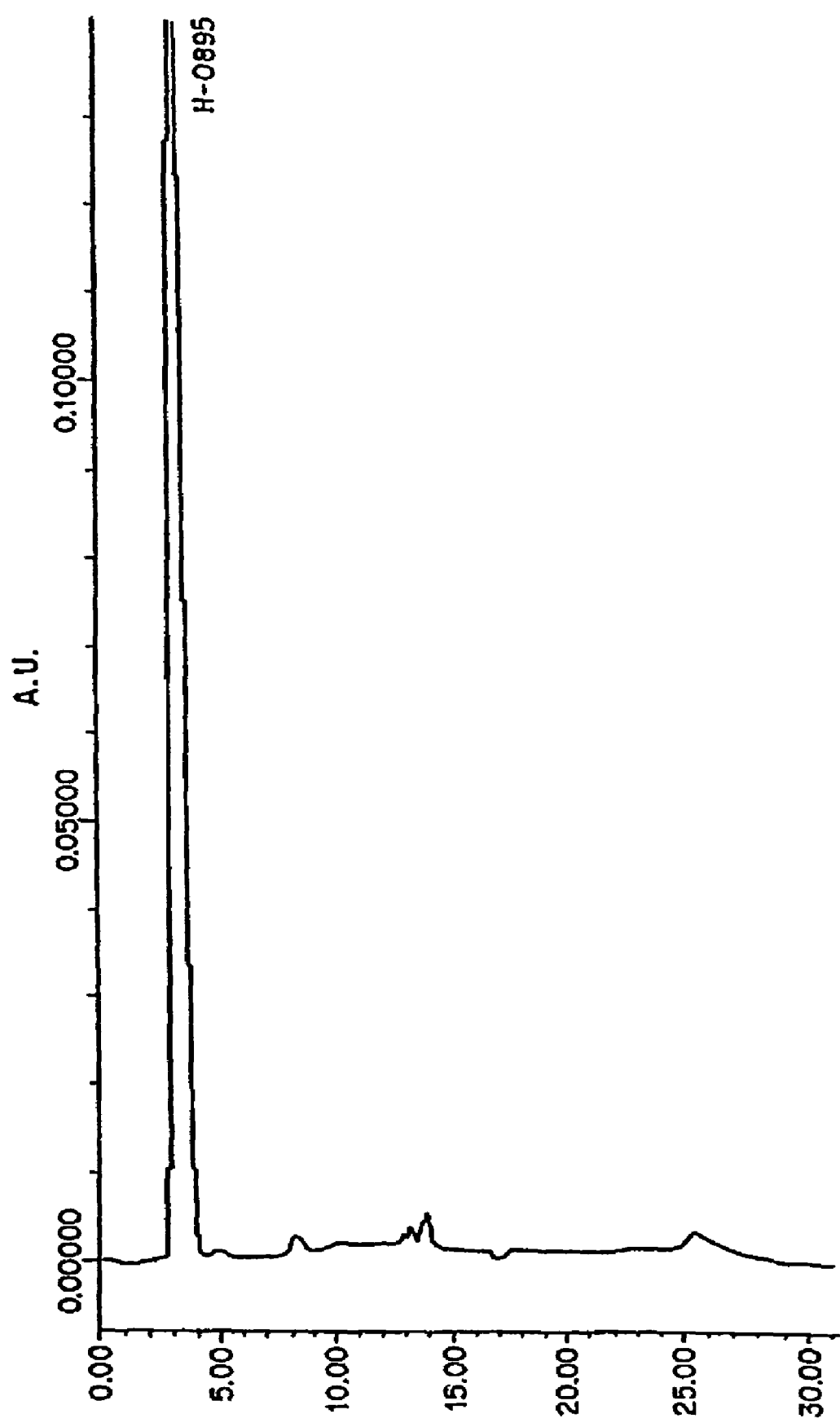

COMPOSITIONS FOR THE REGULATION OF CYTOKINE ACTIVITY

CROSS REFERENCE TO RELATED APPLICATIONS

The present application is a Divisional Application of U.S. Application 09/495,723 filed Feb. 1, 2000 now U.S. Pat. No. 6,750,207, which is a divisional of U.S. application Ser. No. 08/486,127 filed Jun. 7, 1995, which issued as U.S. Pat. No. 6,020,323, which is a continuation-in-part of U.S. patent application Ser. No. 08/436,330 filed Jun. 29, 1995, which issued as U.S. Pat. No. 5,861,382, which is the U.S. National Phase of International Application No. PCT/US93/10868 having International filing date of Nov. 9, 1993, which is a continuation-in-part of U.S. application Ser. No. 08/096,739 filed Jul. 23, 1993, now abandoned, which is a continuation-in-part of U.S. application Ser. No. 07/974,750, filed Nov. 10, 1992, now abandoned, which, is a continuation-in-part of U.S. application Ser. No. 07/878,188 filed May 1, 1992, which is now abandoned, the complete disclosures of which are incorporated by reference herein.

1. FIELD OF THE INVENTION

The present invention relates to substances, their compositions, and methods for the regulation of cytokine activity, for instance, the up regulation or down regulation of Tumor Necrosis Factor alpha (TNF-α) activity. In particular, substances and pharmaceutically acceptable compositions are disclosed which, when administered to a host in effective amounts, either inhibit or augment the secretion of active TNF-α by host cells. It is thought that the secretion of active cytokines, for example TNF-α, by the host's immune effector cells (e.g., the host's activated macrophages) may be regulated by the methods of the present invention.

The present invention also relates to methods for the prevention and/or treatment of pathological processes or, conversely, the initiation of a beneficial immune system-related response involving the induction of cytokine production, secretion, and/or activity. Selected compositions of the present invention comprise an effective low dosage of a low molecular weight heparin (LMWH) to be administered at intervals of up to between five to eight days. Still other compositions include substances comprising carboxylated and/or sulphate oligosaccharides in substantially purified form obtained from a variety of primary sources including chromatographic separation and purification of LMWHs, enzymatically degraded heparin and enzymatically degraded extracellular matrix (DECM).

Individually, the substances, compositions containing same, and pharmaceutical compositions especially suited for parenteral, oral, or topical administration, inhibit or augment TNF-α secretion by resting T cells and/or macrophages in vitro in response to activation by immune effector cell activators, including, but not limited to, T cell-specific antigens, T cell mitogens, macrophage activators, residual extracellular matrix (RECM), fibronectin, laminin or the like. In vivo data, showing inhibition of experimental delayed type hypersensitivity (DTH), are also presented in further support of the in vitro results.

2. BACKGROUND OF THE INVENTION

2.1. Tumor Necrosis Factor Alpha

TNF-α, a cytokine produced by monocytes (macrophages) and T lymphocytes, is a key element in the cascade of factors that produce the inflammatory response and has many pleiotropic effects as a major orchestrator of disease states (Beutler, B. and Cerami, A., *Ann. Rev. Immunol.* (1989) 7:625-655).

The biologic effects of TNF-α depend on its concentration and site of production: at low concentrations, TNF-α may produce desirable homeostatic and defense functions, but at high concentrations, systemically or in certain tissues, TNF-α can synergize with other cytokines, notably inter-leukin-1 (IL-1) to aggravate many inflammatory responses.

The following activities have been shown to be induced by TNF-α (together with IL-1); fever, slow-wave sleep, hemodynamic shock, increased production of acute phase proteins, decreased production of albumin, activation of vascular endothelial cells, increased expression of major histocompatibility complex (MHC) molecules, decreased lipoprotein lipase, decreased cytochrome P450, decreased plasma zinc and iron, fibroblast proliferation, increased synovial cell collagenase, increased cyclo-oxygenase activity, activation of T cells and B cells, and induction of secretion of the cytokines, TNF-α itself, IL-1, IL-6, and IL-8. Indeed, studies have shown that the physiological effects of these cytokines are interrelated (Philip, R. and Epstein, L. B., *Nature* (1986) 323(6083):86-89; Wallach, D. et al., *J. Immunol.* (1988) 140(9):2994-2999).

How TNF-α exerts its effects is not known in detail, but many of the effects are thought to be related to the ability of TNF-α to stimulate cells to produce prostaglandins and leukotrienes from arachidonic acid of the cell membrane.

TNF-α, as a result of its pleiotropic effects, has been implicated in a variety of pathologic states in many different organs of the body. In blood vessels, TNF-α promotes hemorrhagic shock, down regulates endothelial cell thrombomodulin and enhances a procoagulant activity. It causes the adhesion of white blood cells and probably of platelets to the walls of blood vessels, and so, may promote processes leading to atherosclerosis, as well as to vasculitis.

TNF-α activates blood cells and causes the adhesion of neutrophils, eosinophils, monocytes/macrophages and T and B lymphocytes. By inducing IL-6 and IL-8, TNF-α augments the chemotaxis of inflammatory cells and their penetration into tissues. Thus, TNF-α has a role in the tissue damage of autoimmune diseases, allergies and graft rejection.

TNF-α has also been called cachectin because it modulates the metabolic activities of adipocytes and contributes to the wasting and cachexia accompanying cancer, chronic infections, chronic heart failure, and chronic inflammation. TNF-α may also have a role in anorexia nervosa by inhibiting appetite while enhancing wasting of fatty tissue.

TNF-α has metabolic effects on skeletal and cardiac muscle. It has also marked effects on the liver: it depresses albumin and cytochrome P450 metabolism and increases production of fibrinogen, 1-acid glycoprotein and other acute phase proteins. It can also cause necrosis of the bowel.

In the central nervous system, TNF-α crosses the blood-brain barrier and induces fever, increased sleep and anorexia. Increased TNF-α concentration is associated with multiple sclerosis. It further causes adrenal hemorrhage and affects production of steroid hormones, enhances collagenase and PGE-2 in the skin, and causes the breakdown of bone and cartilage by activating osteoclasts.

In short, TNF-α is involved in the pathogenesis of many undesirable inflammatory conditions in autoimmune diseases, graft rejection; vasculitis and atherosclerosis. It may have roles in heart failure and in the response to cancer. For these reasons, ways have been sought to regulate the production, secretion, or availability of active forms of TNF-α as a means to control a variety of diseases.

The prime function of the immune-system is to protect the individual against infection by foreign invaders such as microorganisms. It may, however, also attack the individual's own tissues leading to pathologic states known as autoimmune diseases. The aggressive reactions of an individual's immune system against tissues from other individuals are the reasons behind the unwanted rejections of transplanted organs. Hyper-reactivity of the system against foreign substances causes allergy giving symptoms like asthma, rhinitis and eczema.

The cells mastering these reactions are the lymphocytes, primarily the activated T lymphocytes, and the pathologic inflammatory response they direct depends on their ability to traffic through blood vessel walls to and from their target tissue. Thus, reducing the ability of lymphocytes to adhere to and penetrate through the walls of blood vessels may prevent autoimmune attack, graft rejection and allergy. This would represent a new therapeutic principle likely to result in better efficacy and reduced adverse reactions compared to the therapies used today.

Atherosclerosis and vasculitis are chronic and acute examples of pathological vessel inflammation. Atherosclerosis involves thickening and rigidity of the intima of the arteries leading to coronary diseases, myocardial infarction, cerebral infarction and peripheral vascular diseases, and represents a major cause of morbidity and mortality in the Western world. Pathologically, atherosclerosis develops slowly and chronically as a lesion caused by fatty and calcareous deposits. The proliferation of fibrous tissues leads ultimately to an acute condition producing sudden occlusion of the lumen of the blood vessel.

TNF-α has been shown to facilitate and augment human immunodeficiency virus (HIV) replication in vitro (Matsuyama, T. et al., *J. Virol.* (1989) 63(6):2504-2509; Michihiko, S. et al., *Lancet* (1989) 1(8648):1206-1207) and to stimulate HIV-1 gene expression, thus, probably triggering the development of clinical AIDS in individuals latently infected with HIV-1 Okamoto, T. et al., *AIDS Res. Hum. Retroviruses* (1989) 5(2):131-138).

Hence, TNF-α, like the inflammatory response of which it is a part, is a mixed blessing. Perhaps in understanding its physiologic function, one may better understand the purpose of inflammation as a whole and gain insight into the circumstances under which "TNF-α deficiency" and "TNF-α excess" obtain. How best to design a rational and specific therapeutic approach to diseases that involve the production of this hormone may thus be closer at hand.

2.2. Heparin

Heparin is a glycosaminoglycan, a polyanionic sulfated polysaccharide, which is used clinically to prevent blood clotting as an antithrombotic agent. In animal models, heparin has been shown to reduce the ability of autoimmune T lymphocytes to reach their target organ (Lider, O. et al., *Eur. J. Immunol.* (1990) 20:493-499). Heparin was also shown to suppress experimental autoimmune diseases in rats and to prolong the allograft survival in a model of skin transplantation in mice, when used in low doses (5 μg for mice and 20 μg for rats) injected once a day (Lider, O. et al., *J. Clin. Invest.* (1989) 83:752-756).

The mechanisms behind the observed effects are thought to involve inhibition of release by T lymphocytes of enzyme (s) necessary for penetration of the vessel wall, primarily the enzyme heparanase that specifically attacks the glycosaminoglycan moiety of the sub-endothelial extracellular matrix (ECM) that lines blood vessels (Naparstek, Y. et al., *Nature* (1984) 310:241-243). Expression of the heparanase enzyme is associated with the ability of autoimmune T lymphocytes to penetrate blood vessel walls and to attack the brain in the model disease experimental autoimmune encephalomyelitis (EAE).

European Patent Application EP 0114589 (Folkman et al.) describes a composition for inhibition of angiogenesis in mammals in which the active agents consist essentially of (1) heparin or a heparin fragment which is a hexasaccharide or larger and (2) cortisone or hydrocortisone or the 11-α isomer of hydrocortisone. According to the disclosure, heparin by itself or cortisone by itself are ineffective; only the combination of both gives the desired effects. Although there is no proof in the literature that there is a connection between angiogenesis and autoimmune diseases, the description on page 5 of the patent application connects angiogenesis with psoriasis and with arthritis, indicating the use of high doses of 25,000 units to 47,000 units of heparin per day (i.e., about 160 to about 310 mg per day).

Horvath, J. E. et al., in *Aust. N.Z.J. Med.* (1975) 5(6): 537-539, describe the effect of subanticoagulant doses of subcutaneous heparin on early renal allograft function. The daily dosage is high (5000 U or about 33 mg) and the conclusion of the study is that heparin in subanticoagulant doses has no effect on early graft function or graft survival and that it may be associated with increased hemorrhagic complications.

Toivanen, M. L. et al., *Meth. and Find. Exp. Clin. Pharmacol.* (1982) 4(6):359-363, examined the effect of heparin in high dosage (1000 U/rat or about 7 mg/rat) in the inhibition of adjuvant arthritis in rats and found that heparin enhanced the severity of the rat adjuvant arthritis.

PCT Patent: Application PCT/AU88/00017 published under No. WO88/05301 (Parish et al.) describes sulphated polysaccharides that block or inhibit endoglycosylase activity, such as heparanase activity, for use as antimetastatic and anti-inflammatory agents. Heparin and heparin derivatives, such as periodate oxidized, reduced heparins, that had negligible anticoagulant activity, were shown to have antimetastatic and anti-inflammatory activity when used in dosages within, the range of 1.6-6.6 mg per rat daily, administered by constant infusion (corresponding to 75-308 mg daily for an adult human patient).

Heparin and heparan sulfate are closely related glycosaminoglycan macromolecules. The degradation products of these polymeric macromolecules, which are termed low molecular weight heparins (LMWH), may have the same or greater pharmacologic effects on the blood clotting system as the parent macromolecules. Furthermore, because there is extensive but incomplete post-synthetic processing of the polymer's basic disaccharide subunit, glucuronic acid and N-acetyl glucosamine, the LMWH will be a heterogeneous mixture not only of sizes but also of chemical compositions (See Goodman and Gilman's *The Pharmacological Basis of Therapeutics*, 8th Ed., (Pergamon Press, New York, 1990) pp. 1313-1315. Methods to obtain low molecular weight products from heparin, which are useful as anticoagulants, are described in the art. These methods seek to optimize the persistence in viva or the extent of hemorrhagic side effects of their products (See, for example, Alpino R. R., et al., U.S. Pat. No. 5,010,063; Choay, J., et al., U.S. Pat. No. 4,990,502; Lopez, L. L., et al., U.S. Pat. No. 4,981,955). Others teach the use of affinity chromatographic methods to obtain low molecular weight products (See, for example, Rosenberg, R. D., et al., U.S. Pat. No. 4,539,398 and Jordan, R. E., et al., U.S. Pat. No. 4,446,314).

Psuja, P., as reported in *Folio Haematol. (Leipz)*, (1987) 114:429-436, studied the effect of the heterogeneity of heparins on their interactions with cell surfaces. Psuja reported that there are moderate affinity receptors for LMWH ($D_d$=5.6 µM) found on cultured endothelial cells, but he determined that the upper limit of the fraction of LMWH bound to these receptors was less than 1% of total LMWH.

Other workers have demonstrated effects of LMWH on the metabolism of a variety of cultured cell types. Asselot-Chapel, C., et al., in *Biochem. Pharmacol*. (1989) 38:895-899 and *Biochem. Biophys. Acta*, (1989) 993:240-244, report that LMWH cause cultured smooth muscle cells to decrease the ratio of type III to type I collagen and fibronectin synthesis. Rappaport, R. in U.S. Pat. No. 4,889,808, teaches that LMWH can cause human diploid pulmonary fibroblasts, cultured in the absence of serum, to respond to LMWH by increased secretion of tissue plasminogen activator and related proteins.

Effects of LMWH on complex multicellular systems have been reported. The work of Folkman et al. and Lider et al., in EPO Application 0114589 and *J. Clin. Invest*. (1989) 83:752:756, have been noted above. In addition, Diferrante, N., in published International Application WO 90/03791, teaches the use of LMWH to inhibit the reproduction of HIV in cultures of C8166 transformed human lymphocytes (ALL). However, none of the prior art experiments that have studied the effects of LMWH on cellular metabolism has considered that the heterogeneity of LMWH may produce antagonistic effects. Furthermore, none has shown or suggested a regulatory effect on cytokine activity based on the use of substantially pure oligosaccharide substances.

3. SUMMARY OF THE INVENTION

In the present invention, substances are disclosed which are capable of regulating cytokine activity in a mammalian subject and which are comprised of a carboxylated and/or sulfated oligosaccharide in a substantially purified form. In particular, the substance exhibits a consistent: (a) inhibitory "R" value of about $200,000 \times (\mu g/gm)^{-1}$ or more as determined from an in vivo bioassay that measures the relative inhibition of experimental DTH reactions in mice that have been treated with varying dosages of said substance ranging from 0 to about 2 µg/gm mouse; or (b) augmentative "R" value of about $0.03\% \times (pg/ml)^{-1}$ or more as determined from an in vitro bioassay that measures the relative activity of TNF-α that is secreted by activated human CD4+ T cells in the presence of varying concentrations of said substance from 0 to about $1 \times 10^7$ pg/ml. Preferred substances exhibit in vivo inhibitory "R" values selected from the group consisting of 300,000, 400,000, 500,000 and $600,000\% \times (\mu g/gm)^{-1}$ or more.

Furthermore, the substances of the present invention having an inhibitory effect on the secretion of active TNF-α may, in addition, exhibit a consistent inhibitory "R" value of at least about $0.4\% \times (pg/ml)^{-1}$ as determined from an in vitro bioassay that measures the relative activity of TNF-α that is secreted by activated human CD4+ T cells in the presence of varying concentrations of said substance from 0 to about $1 \times 10^7$ pg/ml.

In one embodiment of the present invention, the carbohydrate or oligosaccharide has a molecular weight of no more than about 3000 daltons, preferably lying in the range of about 400 to about 2000 daltons, most preferably between about 400 and about 1100 daltons. Generally, substances of the present invention which inhibit TNF-α activity, as determined by biological assays (described more fully, below), comprise molecules of various sugar units of which the basic unit of activity is associated with a disaccharide. However, larger oligosaccharide chains of up to about 10 sugar units, containing the basic disaccharide unit of activity can also function to inhibit TNF-α activity. On the other hand, the substances of the present invention, which act to augment the observed activity of TNF-α, are generally of two types: (i) relatively higher molecular weight aggregates of low molecular weight molecules that, in a non-aggregated state, show inhibitory activity; and (ii) disaccharide or monosaccharide subunits that have lost sulfate groups (i.e., have experienced at least some desulfation).

When purified these substances or the compositions that contain them are substantially free of other substances that exert the opposite or antagonistic effect. Thus, a substance exhibiting inhibitory activity ("down" regulation) in a substantially purified form would be substantially free not only of other substances, in general, but of other substances that exhibit augmentation or retard the inhibitory activity of the "down" regulator. The situation would, of course, be reversed in the case of an augmentative substance (i.e., "up" regulators), in which the substance would be substantially free of other substances, particularly those that "down" regulate or antagonize augmentation.

The phrase "regulatory effect" includes both the up regulation or down regulation of any process affecting the availability or resulting activity in vivo or in vitro of cytokines, in general, including IL-1, IL-6, IL-8 and, in particular, TNF-α. Thus, compositions of the present invention may exert a regulatory effect on the host production of TNF-α, on the host secretion of TNF-α, on the extracellular availability of TNF-α, or on the active forms of TNF-α in a host. For instance, but not wishing to be limited by theory, the instant invention may act to elicit the secretion of a substance, such as a protein, which may bind to TNF-α, change its conformation, and, consequently, affect its biological activity. It is also possible that the compositions of the present invention may, in penetrating activated T cells or macrophages, bind to particular oligonucleotide sequences and, thus, affect transcriptional or translational processes that ultimately alter protein synthesis. The compositions may also work through binding to cell surface receptors.

To simplify the following discussion, reference will be made, among others, to the "secretion of active TNF-α" or the regulation of the "activity of TNF-α" with the understanding that a much broader meaning is to be attached to these phrases which encompasses the actual mechanism that is responsible for or the actual manner by which the observed augmentation or inhibition of TNF-α activity is effected by the substances and compositions of the present invention.

The substances of the present invention comprise a carboxylated and/or sulfated oligosaccharide moiety that may be obtained from natural sources, including living organisms. For example, active substances have been isolated and purified from low molecular weight heparin (LMWH) fractions, as well as extracellular matrices that have been degraded by the action of an enzyme, e.g., heparanase derived from animals (mammals),or microorganisms (bacteria). Yet another source of active substances is enzyme-treated heparin (e.g., endoglycosylase-degraded heparin).

Hence, the term "substantially purified form" means that specific steps have been taken to remove non-active components, or components that have an opposing effect, from the oligosaccharide substances and to isolate the active moiety or moieties from mixtures or supernatants, such as those obtained from enzymatic degradation. Specifically, the substances claimed in the present invention are obtained from a rigorous chromatographic process, in which low pressure size-exclusion gel chromatography (i.e., chromatography on Sephadex columns) is but an initial step in the purification scheme. Subsequent to the low pressure separation, high-pressure liquid chromatographic (HPLC) techniques are used to isolate individual component oligosaccharides. Preferably, these steps have resulted in the purification of the individual active substances to substantial homogeneity.

Such a preferred purification step may include, for example, passing mixtures containing the active substance (e.g., fractions obtained from low pressure gel chromatography) through gel permeation HPLC or strong anion exchange (SAX) HPLC columns. Thus, substances comprising oligosaccharides selected from the group consisting of di-, tri-, tetra-, penta-, or hexasaccharides, preferably disaccharides, have been observed and isolated. The oligosaccharides of the present invention are carboxylated and/or sulfated and are, therefore, negatively charged. Particular embodiments of the invention preferentially include disaccharides having three negatively charged groups. Those that exhibit a specific inhibitory activity possess a molecular weight ranging from about 400 to about 2000, preferably, about 400 to about 1100.

The present invention also provides a bioassay for quantifying the effect of a test substance on the secretion of active TNF-α. The bioassay comprises the steps of preincubating human CD4$^+$ T cells in a medium with varying concentrations of a test substance, adding a constant amount of an activator effective to elicit the secretion of TNF-α by the T cells in the absence of said test substance, collecting the medium after a sufficient period of time, and subsequently testing the activity of the TNF-α in the medium. Preferably, the human CD4$^+$ T cells are obtained from peripheral blood mononuclear leukocytes (PBL). Suitable immune effector cell activators include, but are not limited to, T cell-specific antigens, mitogens, macrophage activators, residual extracellular matrix (RECM, defined in Section 4, below), laminin, fibronectin, and the like.

The present invention relies on the specific regulatory activity of particular substances as determined by in vitro and in vivo bioassays described in greater detail, below. Briefly, the substances useful in the present invention display a regulatory (either inhibitory or augmentative) activity relating to the induction of the secretion of active TNF-α which is dose dependent. That is, a plot of the percent inhibition or augmentation versus the dose (e.g., pg/ml of substance) gives rise to a bell-shaped curve from which a maximum percent inhibition (Inh$_{max}$) or augmentation (Aug$_{max}$) is readily apparent. Thus, for every point on such a plot, a "ratio" between the percent inhibition or augmentation and the concentration or dose can be calculated. In the present case, a "specific regulatory activity" or "R" value can be obtained from the ratio of the maximum percent inhibition or augmentation (i.e., Inh$_{max}$ or Aug$_{max}$) and the concentration or dose of test substance which gave rise to such maximum percent regulatory value. Furthermore, an "R" value can be obtained for each bioassay. Hence, an "R" value can be associated from an in vitro mouse spleen cell assay, an ex vivo mouse spleen assay, an in vitro human PBL assay, and an in vivo assay based on experimental DTH reaction. If no effect is observed, an "R" value of zero is assigned.

Another object of the present invention is a method of regulating cytokine activity in a mammalian subject comprising administering to said subject an amount of a substance effective to inhibit or augment the activity of a cytokine in said subject, said substance comprising a carboxylated and/or sulfated oligosaccharide in a substantially purified form and said substance exhibiting a consistent: (a) non-zero inhibitory "R" value as determined from (i) an in vitro bioassay that measures the relative activity of TNF-α that is secreted by activated human CD4$^+$ T cells in the presence of varying concentrations of said substance from 0 to about $1 \times 10^7$ pg/ml, and/or (ii) an in vivo bioassay that measures the relative inhibition of experimental DTH reaction in mice that have been treated with varying dosages of said substance ranging from 0 to about 2 μg/gm mouse; or (b) non-zero augmentative "R" value as determined from an in vitro bioassay that measures the relative activity of TNF-α that is secreted by activated human CD4$^+$ T cells in the presence of varying concentrations of said substance from 0 to about $1 \times 10^7$ pg/ml.

Yet another object of the present invention is a method of using the active substance for the preparation of a pharmaceutical preparation useful for the treatment of the host, which method comprises combining the substance with a pharmaceutically acceptable carrier to provide a unit dose, preferably of low dosage, having an effective amount of the substance. The pharmaceutical preparation may also comprise a stabilizing agent, for example, protamine, in an amount sufficient to preserve a significant, if not substantial, proportion of the initial activity of the substance over an extended period, e.g., about 100 percent over about 3 days. At storage temperatures below room temperature, e.g., about −10 to about 10° C., preferably 4° C., more of the initial activity is preserved, for up to about 4 months.

Because the pharmaceutical compositions of the present invention are contemplated for administration into humans, the pharmaceutical compositions are preferably sterile. Sterilization is accomplished by any means well known to those having ordinary skill in the art, including use of sterile ingredients, heat sterilization or passage of the composition through a sterile filter.

It should also be evident that a primary object of the present invention is to provide a method of treating a host, such as a mammalian subject, suffering from a medical condition the severity of which can be affected by the activity of a cytokine in the host comprising administering to such host an active substance comprising the oligosaccharides of the instant invention in substantially purified form or the pharmaceutical compositions that can be prepared from same. Depending on the medical condition of the particular host substances or compositions can be administered which either reduce the availability or activity of TNF-α or, conversely, enhance TNF-α induction or amplify its activity. Such compositions or pharmaceutical preparations may be administered at low dosage levels and at intervals of up to about 5-8 days, preferably, once a week. Pharmaceutical compositions containing oligosaccharide (e.g., mono-, di-, tri-, or tetrasaccharides, preferably, comprising a disaccharide) substances for parenteral, oral, or topical administration may be administered daily according to convenience and effectiveness and at dosages that would be readily determined by routine experimentation by one of ordinary skill.

The present invention is also related to pharmaceutical preparations for the prevention and/or treatment of pathological processes involving the induction of active TNF-α secretion comprising a pharmaceutically acceptable carrier and a low molecular weight heparin (LMWH) present in a low effective dose for administration at intervals of up to about 5-8 days and which LMWH is capable of inhibiting in vitro secretion of active TNF-α by resting T cells and/or macrophages in response to T cell-specific antigens, mitogens, macrophage activators, residual extracellular matrix (RECM), laminin, fibronectin, and the like.

In a particular embodiment of the present invention the LMWH of the pharmaceutical preparation has an average molecular weight of from about 3,000 to about 6,000 and, furthermore, may be administered every fifth or seventh day.

It is also an objective of the present invention to provide a pharmaceutical preparation to be administered at intervals of up to about 5-8 days for the prevention and/or treatment of pathological processes involving the induction of active TNF-α secretion comprising a pharmaceutically acceptable carrier and a low molecular weight heparin (LMWH) present in a low effective dose.

Active substances and compositions of the present invention are capable of inhibiting experimental delayed type hypersensitivity (DTH) reactions to an applied antigen as evidenced by a reduction in the induration observed after the application of the antigen to the skin up to about five to seven days after the administration of the substance or pharmaceutical composition of same relative to the induration observed after the application of the antigen to the skin in the absence of or after recovery from the administration of the substance or pharmaceutical composition of same. Examples of the applied antigen include, but are not limited to, tetanus, myelin basic protein, purified protein derivative, oxazolone, and the like.

Furthermore, it is an objective of the present invention to provide compositions or pharmaceutical preparations that may be administered in any manner as dictated by the particular application at hand including, but not limited to, enteral administration (including oral or rectal) or parenteral administration (including topical or inhalation with the aid of aerosols). In preferred embodiments, the pharmaceutical compositions of the present invention are administered orally, subcutaneously, intramuscularly, intraperitoneally or intravenously.

Thus, the present invention is useful, for example, in delaying or preventing allograft rejection and treating or preventing a variety of pathological processes such as those related to autoimmune diseases, allergy, inflammatory diseases (in particular, inflammatory bowel disease), or acquired immunodeficiency syndrome (AIDS). The present invention also finds utility in the treatment of diabetes type I, periodontal disease, skin diseases, liver diseases, uveitis, rheumatic diseases (in particular, rheumatoid arthritis), atherosclerosis, vasculitis, or multiple sclerosis.

Moreover, the present invention is useful, in the treatment of tumors, viral infections and bacterial infections by administering a substance of the invention so as to augment the secretion of active TNF-α. Examples of tumor treatment include, but are not limited to, the treatment of breast; colon and prostate cancers as well as lymphomas and other basal cell carcinomas. Bacterial infection treatments include, but are not limited to, the treatment of diphtheria, streptococcus, pneumonia, gonorrhea, leprosy, and tuberculosis. Similarly, examples of viral infections which can be treated by the invention include, but are not limited to, the treatment of influenza, hepatitis, gastroenteritis, mononucleosis, bronchiolitis, and meningitis.

In particular pharmaceutical compositions of is the present invention, low effective doses of the prescribed LMWH active-substance are present. Typically, the pharmaceutical composition contains a single low dose unit of less than 5 mg of LMWH active substance, preferably from about 0.3 to about 3 mg, and most preferably contains a single low dose unit of from 1 to 1.5 mg.

The present invention also contemplates broadly a method of using a low molecular weight heparin (LMWH) which is capable of inhibiting in vitro secretion of active TNF-α by resting T cells and/or macrophages in response to immune effector cell activators for the preparation of a pharmaceutical preparation to be administered at intervals of up to about 5-8 days for the prevention and/or treatment of pathological processes involving induction of TNF-α secretion which method comprises combining a low effective dose of the LMWH with a pharmaceutically acceptable carrier.

Yet another object of the present invention relates to methods for providing sources of active substances according to the present invention which comprise fractionating low molecular weight heparins, enzymatically degrading intact heparin (DH), or enzymatically degrading extracellular matrix (DECM).

A still further object of the present invention is to provide a method of treating a subject or host suffering from a pathological process involving induction of active TNF-α secretion comprising administering to such subject or host a pharmaceutical composition, as described above, at intervals of up to about 5-8 days, preferably once a week. As further described above, pharmaceutical compositions comprising active oligosaccharide may also be administered daily or up to weekly intervals.

The present invention also provides a pharmaceutical composition for the inhibition of the production of active TNF-α comprising a disaccharide of the formula (I) or its pharmaceutically acceptable salt

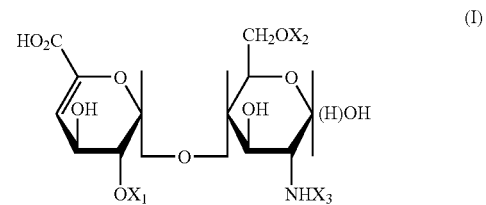

(I)

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates; and a pharmaceutically acceptable carrier. In particular, the pharmaceutical composition may comprise a disaccharide which is 2-O-sulfate-4-deoxy-4-en-iduronic acid-(α-1,4)-2-deoxy-2-N-sulfateglucosamine, 4-deoxy-4-en-iduronic acid-(α-1,4)-2-deoxy-2-N-sulfate-6-O-sulfateglucosamine, 2-O-sulfate-4-deoxy-4-en-iduronic acid-(α-1,4)-2-deoxy-2-N-sulfate-6-O-sulfateglucosamine, or 2-O-sulfate-4-deoxy-4-en-iduronic acid-(α-1,4)-2-deoxy-2-N-acetyl-6-O-sulfateglucosamine.

The present invention also contemplates a pharmaceutical composition for augmenting the production of active TNF-α comprising 4-deoxy-4-en-iduronic acid-(α-1,4)-2-deoxy-2-N-acetylglucosamine or a pharmaceutically acceptable salt thereof and a pharmaceutically acceptable carrier. Such pharmaceutical compositions may, of course, be adapted for various routes of administration including, but not limited to, parenteral administration, oral administration, or topical administration.

Furthermore, a pharmaceutical composition is provided for the inhibition of the production of active TNF-α comprising a compound which is an N-sulfated or N-acetylated 4-deoxy-4-en-glucuronoglucosamine or a pharmaceutically acceptable salt thereof. Such compound, if N-sulfated, has at least one other sulfate group and, if N-acetylated, has at least two sulfate groups. It should be noted that because of the unsaturation (i.e., the double bond at C-4 to C-5) at the "uronic" acid portion of certain of the disaccharides of interest, there is no stereochemistry associated with the C-6 carboxyl group that is essentially in the plane of the six-membered ring. Hence, when the double bond at C-4 to C-5 is present, an iduronic acid is the same as a glucuronic acid. Consequently, the term "uronic" acid is meant to encompass either a glucuronic or an iduronic acid. Likewise, a "urono" group can mean either an idurono or glucurono group.

Yet another aspect of the present invention relates to a pharmaceutical composition for augmenting the production of active TNF-α comprising a non-sulfated N-acetylated 4-deoxy-4-en-glucuronoglucosamine or a pharmaceutically acceptable salt thereof and a pharmaceutically acceptable carrier.

Also contemplated by the present invention is a method of inhibiting the production of an active cytokine in a subject comprising administering to the subject, for example, a mammal, such as a human patient, an effective amount of a disaccharide of the formula (I) or its pharmaceutically acceptable salt

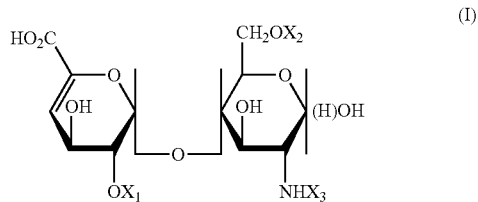

(I)

in which $X_1$ is hydrogen or sulfate; $X_2$ is hydrogen or sulfate; and $X_3$ is sulfate or acetyl, provided that if $X_3$ is sulfate, then at least one of $X_1$ or $X_2$ is sulfate and if $X_3$ is acetyl, then both $X_1$ and $X_2$ are sulfates. Another method relates to augmenting the production of an active cytokine in a subject comprising administering to the subject an effective amount of a disaccharide which is 4-deoxy-4-en-iduronic acid-(α-1,4)-2-deoxy-2-N-acetylglucosamine or a pharmaceutically acceptable salt thereof. Consistent with the objectives of the present invention, such methods include the daily or, preferably, weekly administration of the respective compounds or their pharmaceutically acceptable salts.

The above-mentioned methods may also be utilized for inhibiting or augmenting the production of an active cytokine in a subject comprising administering to the subject an effective amount of the pharmaceutical composition of the present invention.

The present invention also contemplates a method of using a compound which is an N-sulfated or N-acetylated 4-deoxy-4-en-glucuronoglucosamine or a pharmaceutically acceptable salt thereof, the compound if N-sulfated having at least one other sulfate group and the compound if N-acetylated having at least two sulfate groups for the preparation of a pharmaceutical composition for the prevention or treatment of a medical condition caused by or related to the inappropriate production of TNF-α.

Also contemplated is a method of using a compound which is a non-sulfated N-acetylated 4-deoxy-4-en-glucuronoglucosamine or a pharmaceutically acceptable salt thereof for the preparation of a pharmaceutical composition for the treatment of a medical condition responsive to an increased production of TNF-α.

Likewise, methods of preventing or treating a medical condition caused by or related to the inappropriate production of an active cytokine in a subject are also provided comprising administering to the subject an effective amount of a compound which is an N-sulfated or N-acetylated 4-deoxy-4-en-glucuronoglucosamine or a pharmaceutically acceptable salt thereof, the compound if N-sulfated having at least on other sulfate group and the compound if N-acetylated having at least two sulfate groups. Methods of treating a medical condition responsive to an increased production of an active cytokine in a subject area also provided which comprise administering to the subject an effective amount of a compound which is a non-sulfated N-acetylated 4-deoxy-4-en-glucuronoglucosamine or a pharmaceutically acceptable salt thereof. Such treatments are particularly useful in cases involving an autoimmune disease, a neoplastic condition or some form of infection, including those induced by viral, bacterial or fungal agents.

Other objects of the present invention concern methods of protecting a subject from the harmful effects of exposure to radiation comprising administering to the subject an effective amount of a compound which is an N-sulfated or N-acetylated 4-deoxy-4-en-glucuronoglucosamine or a pharmaceutically acceptable salt thereof, the compound if N-sulfated having at least one other sulfate group and the compound if N-acetylated have at least two sulfate groups. Typically, the compounds of the present invention are administered to the subject prior to radiation exposure. Most advantageously, the radioprotective properties of the disclosed compounds may be exploited during radiation therapy.

Further, methods of suppressing allograft rejection in a subject are contemplated comprising administering to the subject an effective amount of a compound which is an N-sulfated or N-acetylated 4-deoxy-4-en-glucuronoglucosamine or a pharmaceutically acceptable salt thereof, the compound if N-sulfated having at least one other sulfate group and the compound if N-acetylated have at least two sulfate groups. The allograft may, of course, include an organ transplant, including, but not limited to, heart, liver, kidney or bone marrow transplants. The disclosed methods may also apply to skin grafts.

Yet another object relates to a method of suppressing the expression of an adhesion molecule in a subject comprising administering to the subject an effective amount of a compound which is an N-sulfated or N-acetylated 4-deoxy-4-en-glucuronoglucosamine or a pharmaceutically acceptable salt thereof, the compound if N-sulfated having at least one other sulfate group and the compound if N-acetylated have at least two sulfate groups. Examples of such adhesion molecules include, but are not limited to, ICAM-1 or ELAM-1.

Also disclosed is an in vitro bioassay for quantifying the effect of a test substance on the secretion of active TNF-α comprising preincubating human $CD4^+$ T cells in a medium with varying concentrations of a test substance, adding a constant amount of an activator effective to elicit the secretion of TNF-α by the T cells in the absence of the test substance, collecting the medium after a sufficient period of time, and subsequently testing the activity of the TNF-α in the medium.

Further objects of the present invention will become apparent to those skilled in the art upon further review of the following disclosure, including the detailed descriptions of specific embodiments of the invention.

BRIEF DESCRIPTION OF THE FIGURES

FIG. 5 illustrates the AA scores obtained from groups of mice that were treated either weekly or daily with various low molecular weight heparins including Fraxiparin, Fraxiparine, and Lovenox.

FIG. 17 shows that the areas of greatest anti-TNF-α effect lie in the subfraction between about 5.65 and about 5.8.

FIGS. 20A and 20B, on the other hand, illustrate the absorption at 206 and 232 nanometers, respectively, of a peak obtained from the HPLC separation of fraction F5.

FIGS. 25A, 25B and 25C illustrate the chromatograms that are obtained from the SAX-HPLC column separation of disaccharide standards obtained from Sigma labeled H-0895, H-1020 and H-9267, respectively.

4. DETAILED DESCRIPTION OF THE INVENTION

Figure 1:
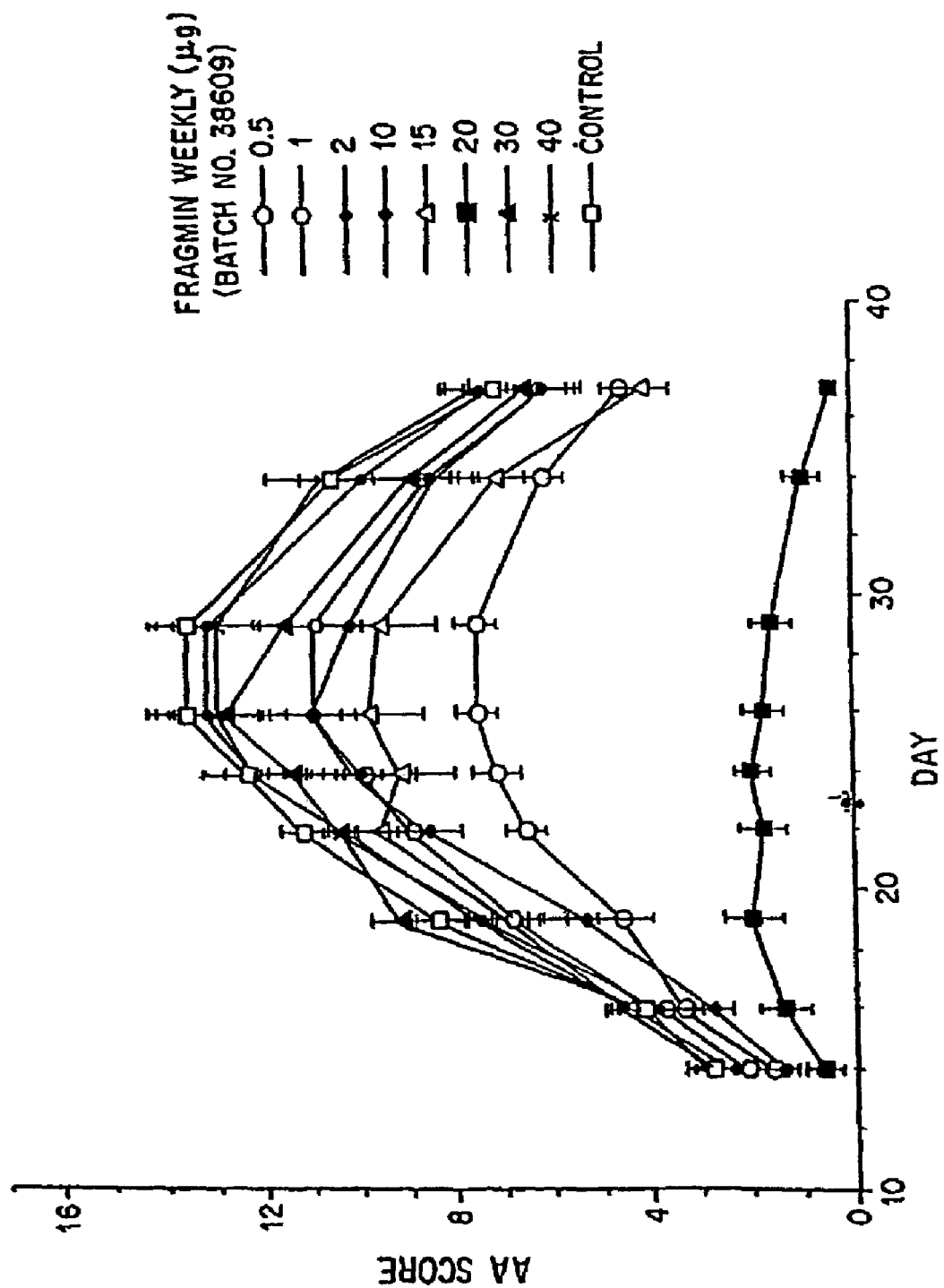
FIG. 1 illustrates the adjuvant arthritis (AA) scores obtained from groups of rats which were treated with weekly administrations of Fragmin at various doses relative to a control group that received only phosphate buffered saline (PBS).

In one aspect of the present invention, it was found that treatment with low molecular weight heparins (LMWHs) inhibited the ability of T cells and madrophages to secrete active TNF-α. In another aspect of the present invention, other substances, comprising carboxylated and/or sulfated oligosaccharides in substantially purified form, are described which collectively represent a means for regulating the biological activity of cytokines, such as TNF-α, in a host. For simplicity, the term "substance(s)" or "active substance(s)" will be used to denote LMWHs, as used in the method of treatment disclosed herein, as well as the substances comprised of carboxylated and/or sulfated oligosaccharides that have been isolated herein in substantially pure form unless otherwise noted.

One functional expression of this effect can be seen in the inhibition in mice and humans of the delayed type hypersensitivity (DTH) reaction, a T cell dependent inflammatory reaction that may also be triggered by cells involving macrophages and other inflammatory cells. Treatment with the active substances at doses affecting active TNF-α production also was able to inhibit a model of autoimmune arthritis called adjuvant arthritis (AA). Active substance treatment also prolonged the survival of allogeneic heart transplants in rats and abrogated insulin dependent diabetes mellitus (IDDM) in NOD mice. Moreover, similar treatment prevented the induction of active TNF-α production by T cells and macrophages in response to the stimulus of damaged or residual subendothelial extracellular matrix. This residual extracellular matrix (RECM) that is responsible for signaling the onset of TNF-α induction (and resulting inflammation) is to be distinguished from the enzyme degraded extracellular matrix (DECM), selected components of which have been isolated herein and have been shown to either shut down TNF-α activity or amplify it.

Since TNF-α at the site of vascular injury probably has a role in the process of atherosclerosis, inhibition of TNF-α activity at the site of damaged subendothelial ECM will ameliorate the pathogenic process of atherosclerosis. A most surprising aspect of treatment with the LMWH active substances is that such treatment is most effective when administered at low doses at weekly intervals. High doses of the LMWH active substances or doses of the LMWH active substances given daily are not effective in inhibiting TNF-α secretion or immune reactions.

Low molecular weight heparins, produced by friactionation or controlled depolymerization of heparins, show improved antithrombotic performance but also different pharmacokinetic properties as compared to heparin: the half-life is doubled and the bioavailability is higher with respect to their anticoagulant effect after subcutaneous injection (Bratt, G. et al., *Thrombosis and Haemostasis* (1985) 53:208; Bone, B. et al., *Thrombosis Research* (1987) 46:845).

According to the present invention it has now been found that the LMWH active substances administered at subanticoagulant doses at several day intervals are effective in the prevention and/or treatment of pathological processes involving induction of active TNF-α. Moreover, it has now been found that discrete substances, comprising an oligosaccharide of from 1-10 sugar units, preferably 2-4 sugar units, can be identified which can either inhibit or augment the activity of TNF-α. These discrete substances can be obtained, for example, from the tissue of a living organism, for instance, from the soluble degradation products of substrate extracellular matrix.

4.1. Sources of Active Substances

The LMWHs to be used according to the invention are derived from LMWHs with an average molecular weight of 3000-6000, such as, for example the LMWHs disclosed in European Patent EP 0014184. Some LMWHs are commercially available under different trade names, e.g., Fragmin®, Fraxiparine®, Fraxiparine®, Lovenox®/Clexane®.

LMWHs can be produced in several different ways: enrichment by fractionation by ethanol and/or molecular sieving, e.g., gel filtration or membrane filtration of the LMWH present in standard heparin and controlled chemical (by nitrous acid, β-elimination or periodate oxidation) or enzymatic (by heparinases) depolymerization. The conditions for depolymerization can be carefully controlled to yield products of desired molecular weights. Nitrous acid depolymerization is commonly used. Also employed is depolymerization of the benzylic ester of heparin by β-elimination, which yields the same type of fragments as enzymatic depolymerization using heparinases. LMWH with low anticoagulant activity and retaining basic chemical structure can be prepared by depolymerization using periodate oxidation or by removing the antithrombin-binding fraction of LMWH, prepared by other methods, using immobilized antithrombin for adsorption.

Fragmin® is a low molecular weight heparin with average molecular weight within the range of 4000-6000 dalton, produced by controlled nitrous acid depolymerization of sodium heparin from porcine intestinal mucosa. It is manufactured by Kabi Pharmacia, Sweden, under the name Fragmin®, for use as an antithrombotic agent as saline solutions for injection in single dose syringes of 2500 IU/0.2 ml and 5000 IU/0.2 ml, corresponding to about 16 mg and 32 mg, respectively.

Fraxiparin®, and Fraxiparine® are LMWHs with average molecular weight of approximately 4500 dalton, produced by fractionation or controlled nitrous acid depolymerization, respectively, of calcium heparin from porcine intestinal mucosa. It is manufactured by Sanofi (Choay Laboratories) for use as an antithrombotic agent in single doses comprising ca. 36 mg, corresponding to 3075 IU/0.3 ml of water.

Lovenox® (Enoxaparin/e), a LMWH fragment produced by depolymerization of sodium heparin from porcine intestinal mucosa, using β-elimination, is manufactured by Pharmuka SF, France and distributed by Rhone-Poulenc under the names Clexane® and Lovenox® for use as antithrombotic agent in single dose syringes comprising 20 mg/0.2 ml and 40 mg/0.4 ml of water.

As shown in the present application, the novel properties of LMWHs that have been discovered and are described herein are common to all LMWHs regardless of the manufacturing process, the structural differences (created by depolymerization or those dependent on variation in the heparin used as raw material) or the anticoagulant activity, provided that the LMWH employed is capable of inhibiting active TNF-α secretion in vitro by resting T cells and/or macrophages in response to activation by contact with T cell-specific antigens, mitogens, macrophage activators, residual ECM or its protein components, such as fibronectin, laminin, or the like.

Another test useful for identifying the LMWHs that are effective for the purpose of the present invention is the inhibition of experimental delayed type hypersensitivity (DTH) skin reactions, a T lymphocyte dependent reaction, to a variety of antigens (for example, tetanus antigen, myelin basic protein (MBP), purified protein derivative (PPD), and oxazolone). The LMWHs also inhibit T cell adhesion to ECM and its protein components.

The LMWHs effective according to the invention are incorporated into pharmaceutical compositions, for example, as water solutions, possibly comprising sodium chloride, stabilizers and other suitable non-active ingredients. The preferable way of administration is by injection, subcutaneous or intravenous, but any other suitable mode of administration is encompassed by the invention, including oral administration.

According to the invention, the LMWH is to be administered at intervals of up to about five to eight days, preferably once a week. The other substances of the present invention, particularly the lower molecular weight (below 2000) oligosaccharides, may be administered in any convenient, effective manner (e.g., by injection, orally, or topically) at dosage regimens that may include daily or weekly administration.

4.2. Loss of Activity of LMWH Preparations Over Time. Influence of Added Stabilizer Time course studies conducted by the inventors demonstrate that LMWH samples, such as Fragmin, lose their ability to inhibit the activity of TNF-α within 72 h at ambient temperature and within a few months at low temperature (e.g., 4° C.).

Table XI, Section 6.1, below, indicates that about 53% of activity of Fragmin® is lost after a day at ambient temperature. After about two days, about 87% of activity is lost, and after about three days, no activity is shown. As shown in Table XII, Section 6.2, below, experiments have shown that Fragmin® loses its anti-DTH reactivity even at colder temperatures (4° C.); the process only requires more time. Conventional non-fractionated heparins, in contrast, do not lose their classic anti-coagulant activities at 4° C.

In an effort to discover an agent capable of stabilizing or preserving the cytokine inhibitory activity of the disclosed LMWH preparations, the inventors turned to a well known heparin additive. Protamine sulfate is known to neutralize the anti-coagulant effects of heparinoid molecules and is used clinically for that purpose (See, Goodman and Gilman's *The Pharmacological Basis of Therapeutics, Eighth Edition*, Pergamon Press, New York, 1990, p. 1317). It has been discovered, however, according to the invention that added protamine sulfate does not neutralize the inhibition of TNF-α-dependent activity by LMWH; in fact, protamine sulfate actually stabilizes this activity (See, Entries in Table XII, below, containing added protamine sulfate).

In summary, one can conclude that (i) diluted LMWH solutions lose activity quickly at 20° C. and more slowly at 4° C. (it should be noted that the activity loss at 4° C. is not a feature of the standard anti-coagulant and anti-thrombotic activities of heparin or LMWH); (ii) added protamine sulfate, the classic neutralizer of the standard activities of heparins, does not interfere with the novel activity of LMWHs against TNF-α described in the present disclosure. Indeed, the inventors have demonstrated that protamine sulfate actually preserves this novel activity.

Figure 10:
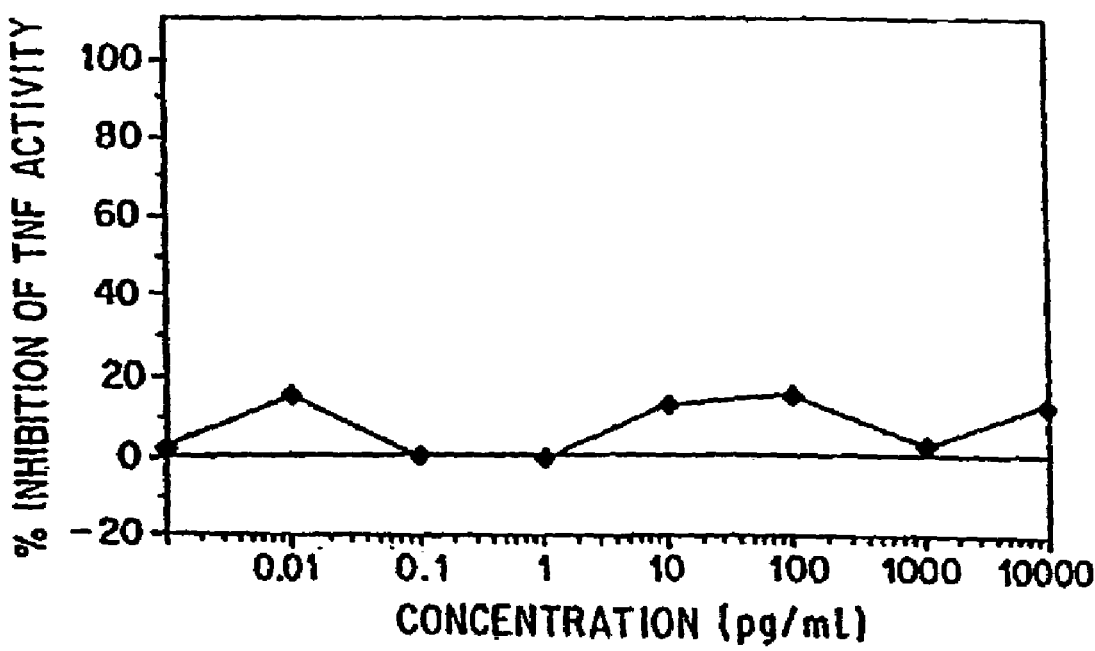
FIG. 10 illustrates the loss of inhibitory activity displayed by inactivated Fragmin.
Figure 11:
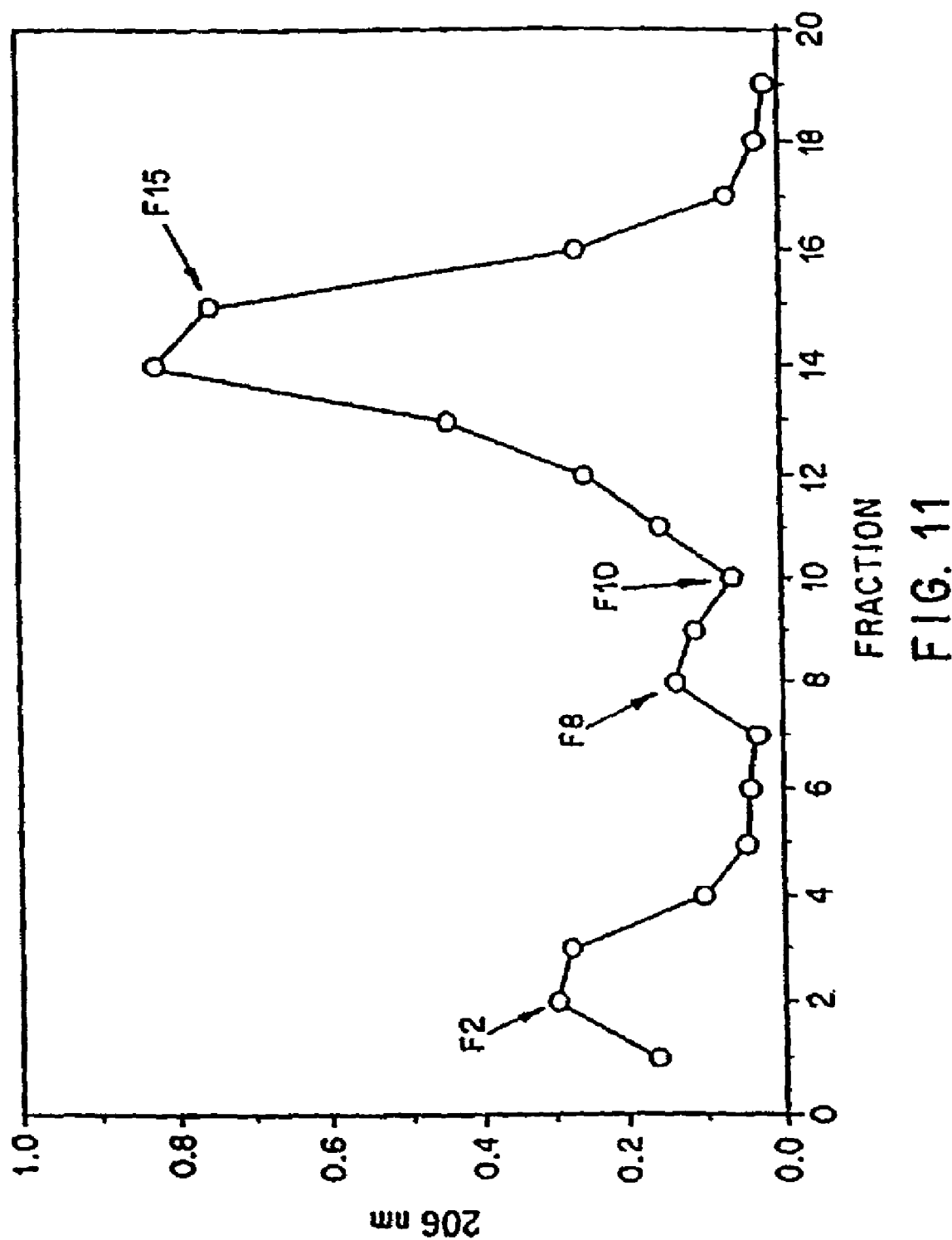
FIG. 11 shows the absorption at 206 nanometers of various fractions obtained from the gel filtration of inactivated Fragmin, including fractions. F2, F8, F10 and F15.
Figure 12:
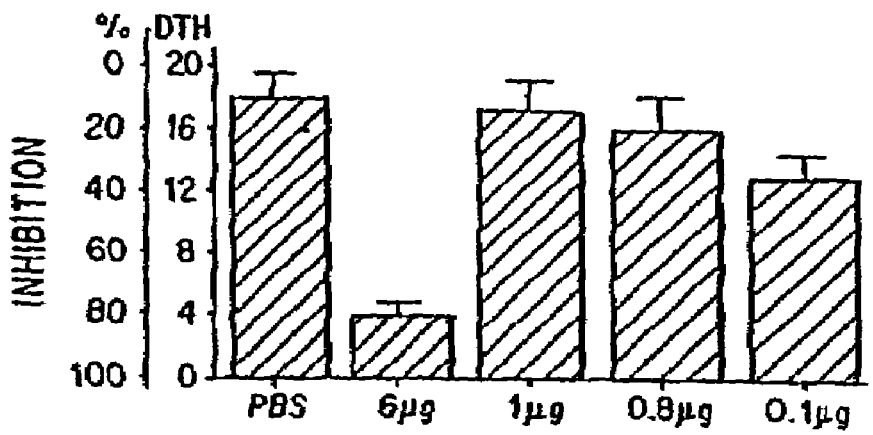
FIGS. 12, 12A and 12B illustrate the effects of active Fragmin; fraction F15, and Fraction F10, respectively, at various doses on the sensitivity of mice to the DTH-reaction.

4.3. Fractionation of LMWH and Preparation of Degraded ECM or Degraded Heparin. Discovery of Distinct Augmentative and Inhibitory Activities For and Against TNF-α Activity As already discussed above, Low Molecular Weight Heparin (Fragmin) inhibits secretion of active TNF-α. Maximal inhibition or $Inh_{max}$ (90%), was observed at a concentration of 1 pg/ml. (See, FIG. 9). By contrast, inactivated Fragmin had no effect on TNF-α production (See, FIG. 10). However, fractionation of the inactivated material by low-pressure size-exclusion gel chromatographic separation using a Sepharose 4B solid support (See, FIG. 11 for a plot of the absorbance at 206 nm versus fraction number) revealed active fractions of both inhibitory (F-15) and augmentative (F8, F2) effects (See, FIG. 11 and Table XIII). The inhibitory fraction of the inactivated Fragmin (F-15) also inhibited the DTH reaction (See, FIGS. 12; relating to active Fragmin®, 12A; relating to fraction F15, and 12B; relating to fraction F10). Fraction F10 had no effect on TNF-α production or DTH reactivity.

A Sepharose 4B size-exclusion gel chromatographic separation was also carried out on the degradation products obtained from heparanase-treated ECM labeled with $^{35}$S-containing sulfate groups. Several types of heparanase enzyme were used in the present investigation. These enzymes include MM5 (Mammalian heparanase from human placentas, obtained commercially from Rad-Chemicals, Weizmann Industrial Park, Ness Ziona, Israel), PC3 (Bacterial endoglycosidase, as described in Shoseiov, O. et al., *Biochem. Biophys. Res. Commun.* (1990) 169:667-672), and an enzyme from a bacterial source obtained from IBEX Technologies, Quebec, Canada. A plot of the radioactivity (CPM) versus fraction number is presented in FIG. 13. Another plot superimposing the elution profiles of fractionated Fragmin and fractionated ECM-heparanase is shown in FIG. 14. The conditions for the Sepharose 4B low-pressure separation are listed in Table I, below.

TABLE I

| Sepharose 4B Chromatography Conditions | |
|---|---|
| Column: | Sepharose 4B (35 cm × 0.7 cm ID) |
| Load: | 1-1.5 ml |
| Flow: | 5 ml/hr |
| Solvent: | PBS (pH = 7.4) |
| Fraction: | 0.2-0.5 ml/tube |
| Detector Absorption Setting: | 206 nm, 280 nm |

The various fractions were assayed for their effect on TNF-α production and these results are presented in Table XV, below. Interestingly, fractions of similar elution properties from the two sources (i.e., F-39 and F-42 from Fragmin and Heparanase-degraded ECM) were found to have similar qualitative biological effects on TNF-α production and/or activity.

Figure 13:
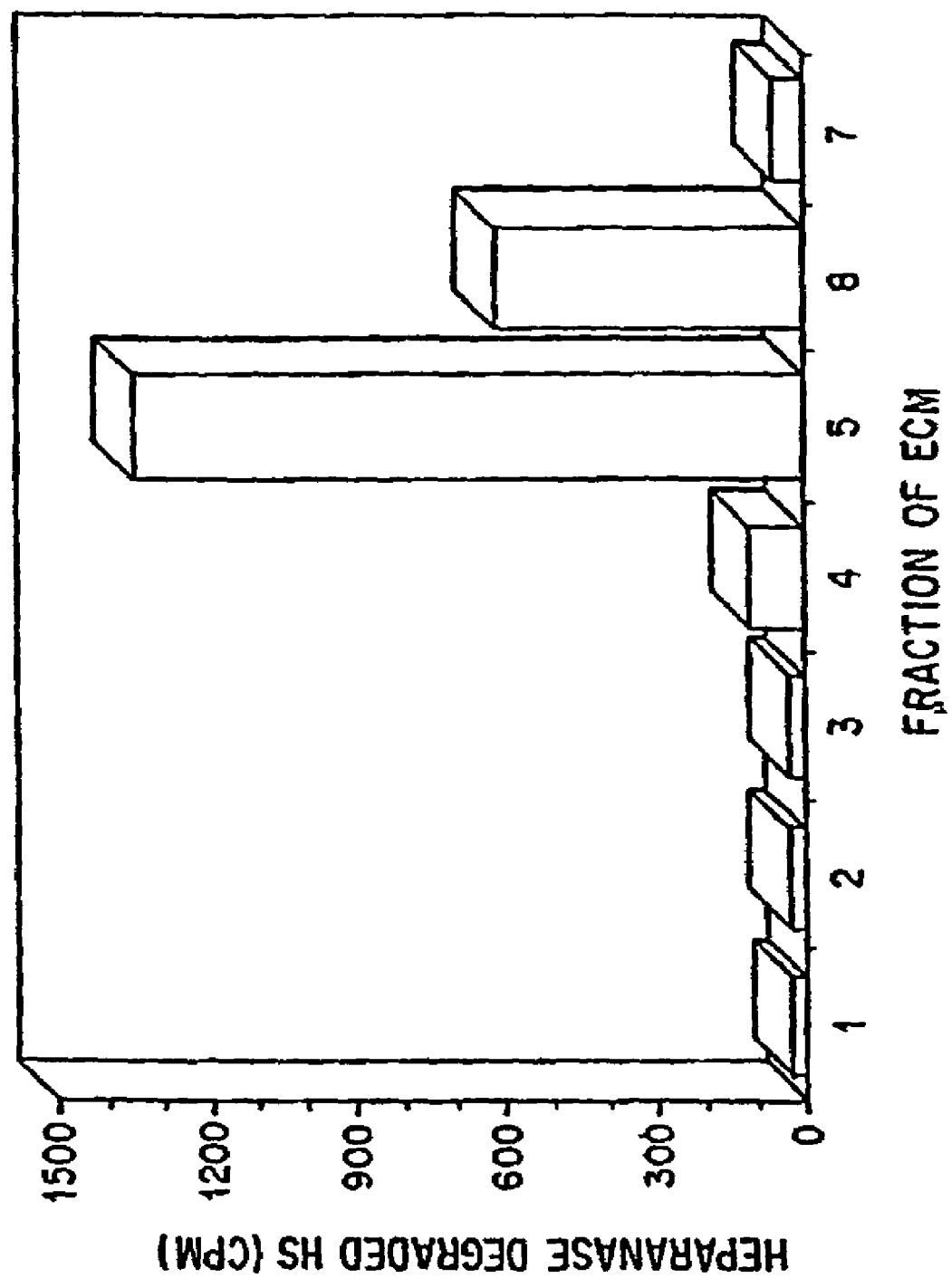
FIGS. 13 and 15 compare the elution profiles of fractions obtained from the Sepharose 4B column separation of Fragmin and heparanase-degraded ECM.
Figure 14:
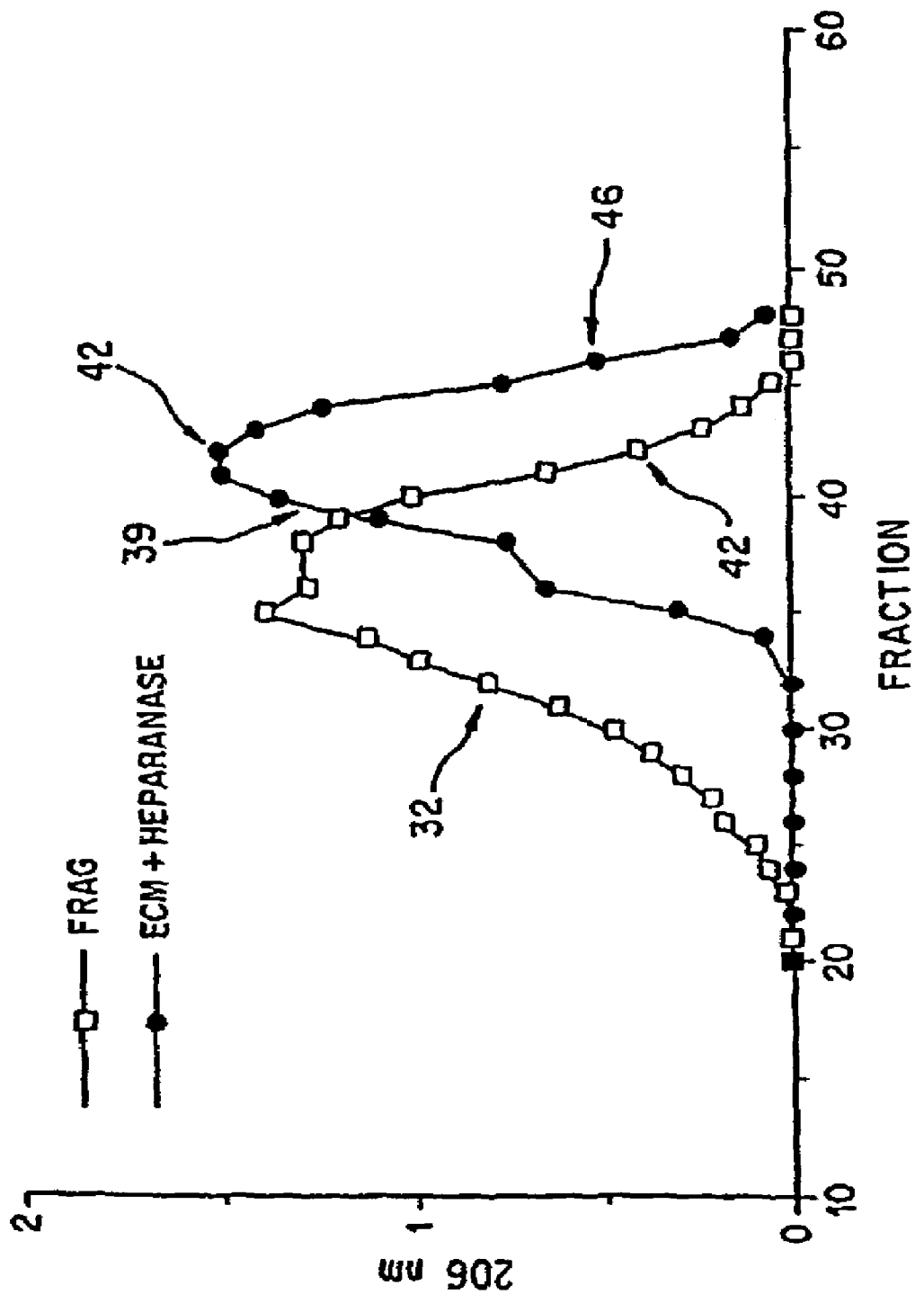
FIG. 14 illustrates the absorption at 206 nanometers versus fraction number for a number of fractions obtained from the Sepharose 4B column separation of Fragmin and heparanase-degraded ECM.
Figure 15:
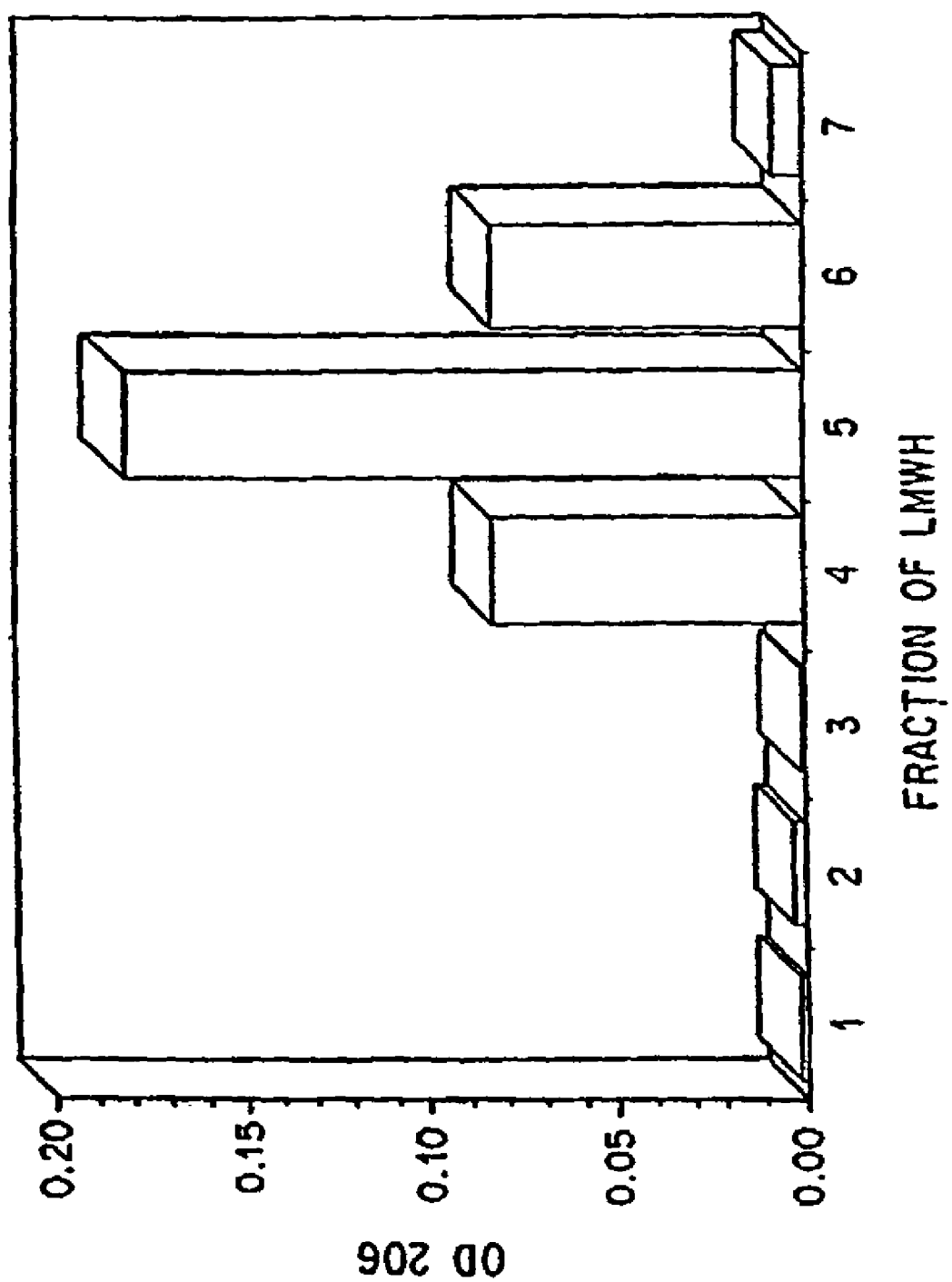

FIGS. 15 and 13 illustrate one way of presenting the elution profile, obtained on Sepharose 4B columns, of LMWH (Fragmin) and $^{35}$S-sulfate labeled oligosaccharides of ECM, produced by purified MM5 heparanase, respectively. It can be seen in FIG. 13 that the heparan sulfate of the ECM (the substrate of heparanase) is degraded by the enzyme to produce heparan sulfate fragments with elution properties comparable to fractionated LMWH.

Figure 16:
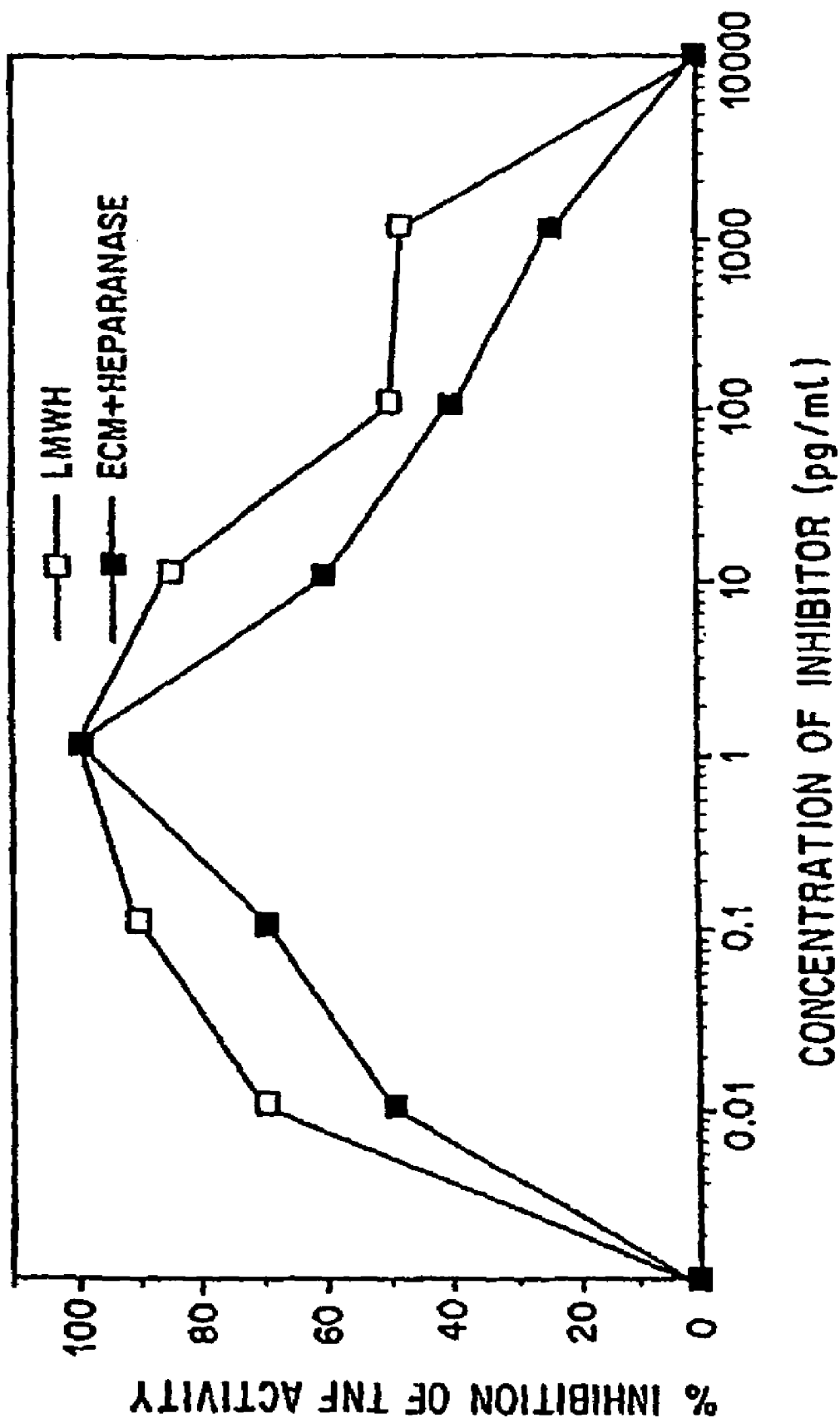
FIG. 16 shows that an oligosaccharide product (fraction 5 from FIG. 13) demonstrated a similar bell-shaped dose/response curve in its ability to inhibit the secretion of active TNF-α.

FIG. 16 shows that an oligosaccharide product (Sepharose 4B fraction #5, FIG. 13), obtained from the ECM+heparanase "soup" (i.e., the mixture obtained from the heparanase degradation of ECM), has a substantially similar dose/response characteristic as LMHW in its effects on the secretion of active TNF-α: that is, both display a bell-shaped dose/response curve and both exhibit maximal inhibition of about 90% at a concentration of about 1 pg/ml with less activity at either lower or higher concentrations. It is advantageous, thus, that the administration of these active substances includes dosages falling within an easily determined "window" of physiological effect.

FIG. 17 shows that the anti-TNF-α effect of the ECM-degradation products is highest in the area of a subfraction (between about 5.65 and about 5.80) of the fragments under peak number 5 of FIG. 13.

Thus, heparan sulfate can be acted upon by heparanase to generate degradation products that, like LMWH, feed back on the T cells and macrophages to shut off active TNF-α production and, consequently, TNF-mediated inflammation.

It has also been discovered that low-molecular weight oligosaccharide fragments, obtained from endoglycosylase treatment of intact heparin, exhibit the desired regulatory effect over TNF-α activity.

4.4. HPLC Separation of LMWH-Fractions and Fragments Obtained from DECM and DH

High performance liquid chromatography ("HPLC") techniques were utilized to obtain better resolution of the fractions from the LMWH (e.g., Fragmin), ECM-degradation, and heparin-degradation samples. Initially two types of HPLC conditions were used. Under the first set of HPLC conditions; a

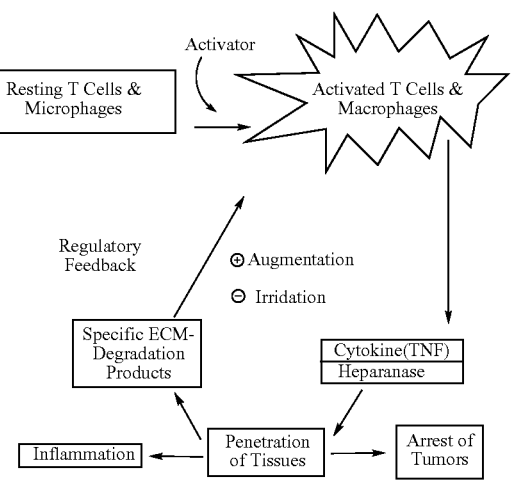

CYTOKINE REGULATORY SCHEME number of individual fractions were separated and isolated; their ability to regulate the secretion of active TNF-α was then examined. To the great surprise of the present inventors, it was discovered that selected fractions can augment the activity of TNF-α in the host while others inhibited TNF-α activity. A second set of HPLC conditions was then utilized to better separate the various components according to their molecular weight.

Figure 18A:
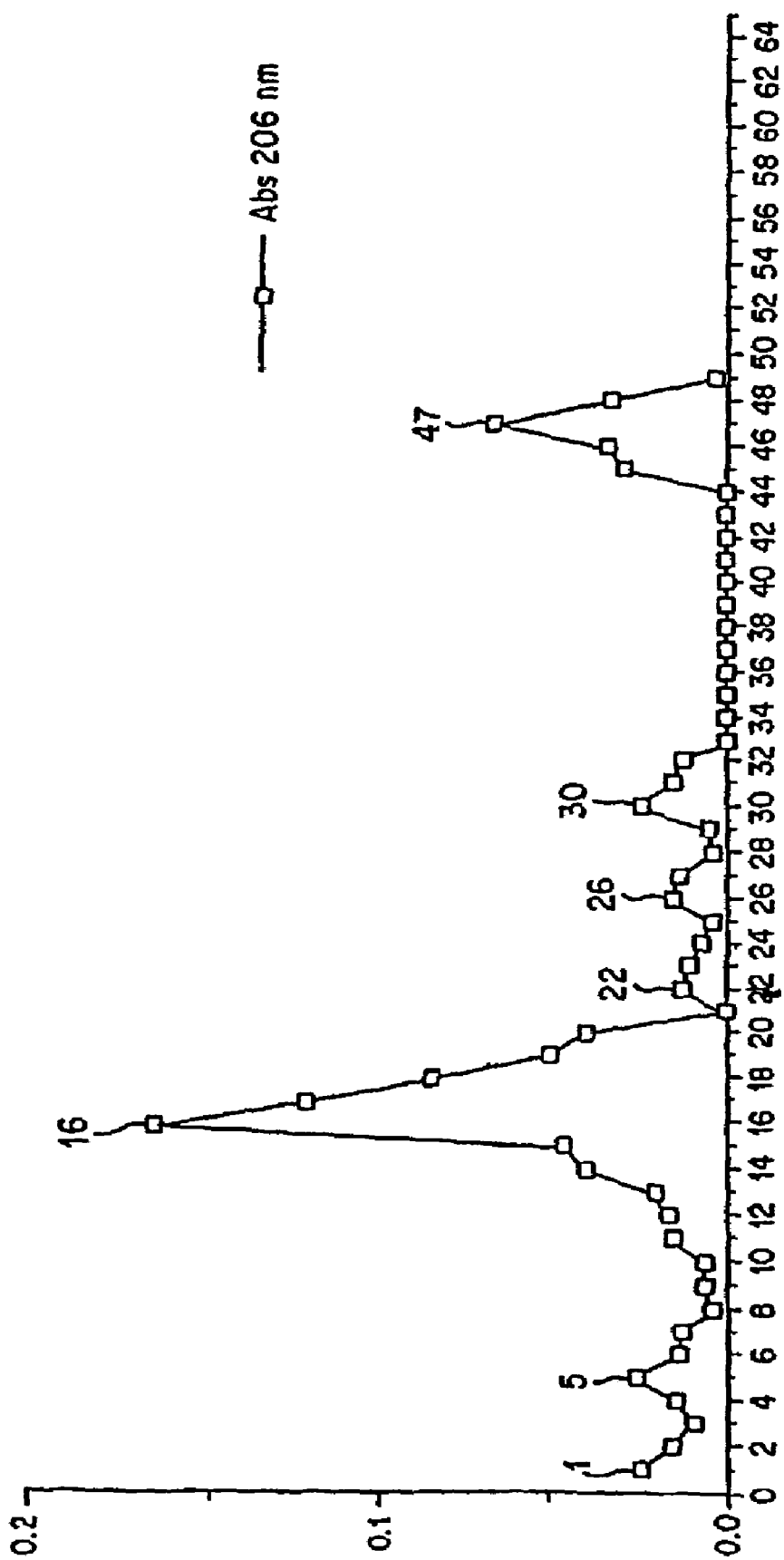
FIGS. 18A and 18B illustrate the chromatogram obtained from the HPLC separation of Fragmin and heparanase-degraded ECM, respectively.
Figure 18B:
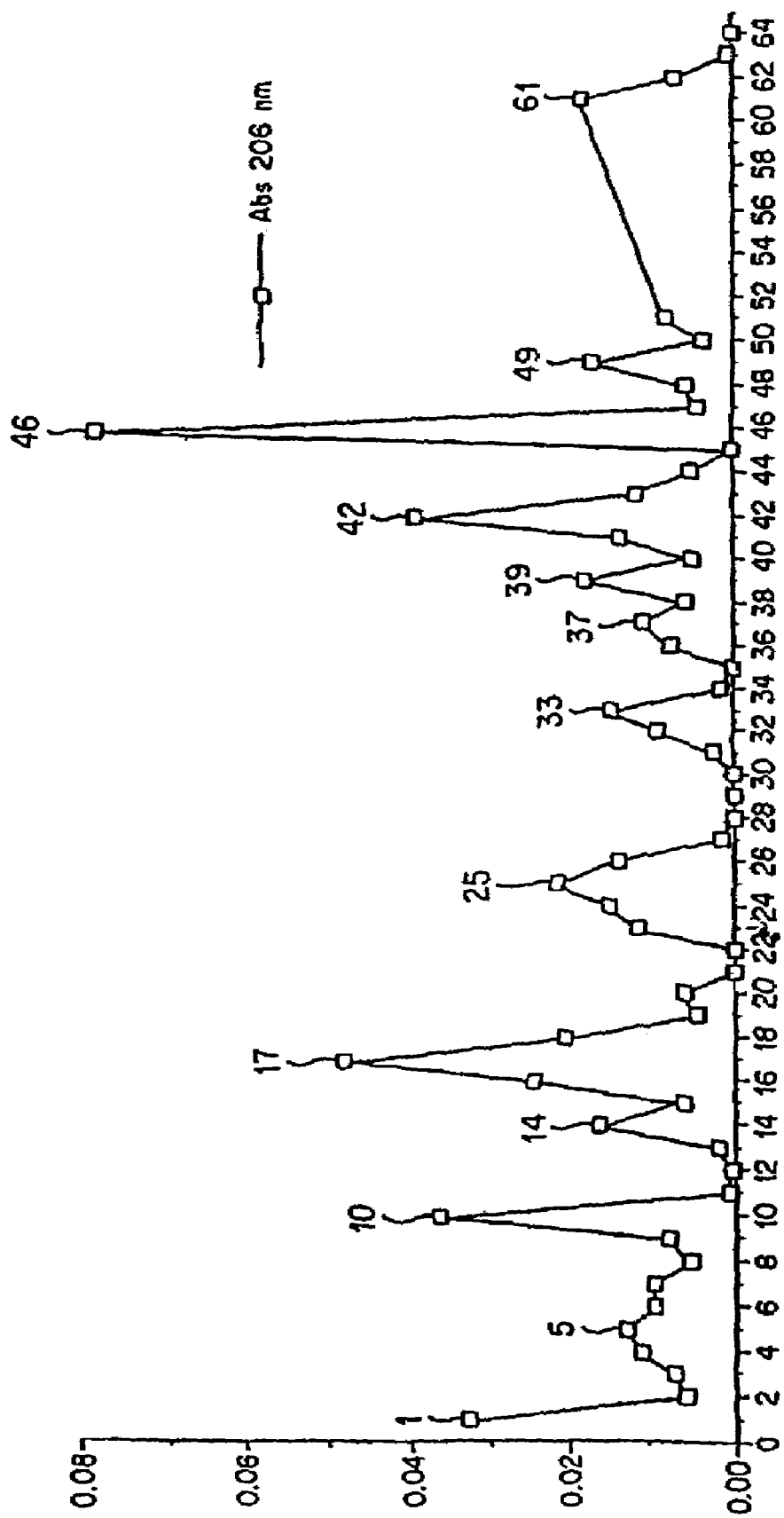

In the first set of HPLC conditions, a TSK-GEL® G-Oligo-PW column (30 cm×7.8 mm I.D.) equipped with a Guardcolumn Oligo (4 cm×6 mm I.D.) was used. The conditions ("HPLC I") are provided in Table II, below. A representative chromatogram for the HPLC I separation of Fragmin and ECM+MM5 Heparanase is illustrated in FIGS. 18A and 18B, respectively.

TABLE II

| HPLC I Chromatography Conditions | |
|---|---|
| Column: | TSK-GEL G-Oligo-PW 30 cm × 7.8 mm ID |
| Guard Column: | Guardcolumn Oligo 4 cm × 6.0 mm ID |
| Loop: | 200 µl |
| Flow: | 0.5 ml/min. |
| Solvent: | 0.2 M phosphate buffer (pH = 7.0) |
| Fraction: | 0.5 ml/tube |
| Detector Absorption Setting: | 190 nm-400 nm |

The second set of HPLC conditions ("HPLC II") are described in Table III, below, and utilized conditions similar to those described by Rice,. K. G. et al. in *Analytical Biochem.* (1985) 150:325-331. Hence, two columns connected in series were used: a Toyo Soda TSK-Gel G3000SW (7.5 mm×50 cm) column connected to a G2000SW (7.5 mm×50 cm) column. These columns, together with a 7.5 mm×10 cm guard column attached to the inlet end of the G2000 column, were obtained from Phenomenex. Further experimental details are described in Sections 6.11, 6.14 and 6.15, below.

TABLE III

HPLC II Chromatography Conditions

| | |
|---|---|
| Column: | Toyo Soda TSK-GEL G3000SW (50 cm × 7.5 mm ID) and a G2000SW (50 cm × 7.5 mm ID) in series Guard |
| Column: | Guardcolumn (10 cm × 7.5 mm ID) |
| Loop: | 20 or 100 µl |
| Flow: | 1 ml/min. |
| Solvent: | degassed 0.5 M NaCl |
| Fraction: | 0.5 ml/tube |
| Detector Absorption Setting: | 205 nm, 232 nm |

Under these conditions, smaller substances are retained longer than larger molecules.

In yet another set of HPLC conditions ("HPLC III"), the purity of selected desalted HPLC fractions was examined with the aid of a strong anion exchange (SAX) HPLC column. Such SAX HPLC-columns are known to separate similarly sized molecules according to the number of negatively charged groups which are present in the molecules. The greater the number of negatively charged groups in a substance, the longer it is retained in the column. The HPLC III conditions are outlined in Table IV, below.

TABLE IV

HPLC III Chromatography Conditions

| | |
|---|---|
| Column: | SAX-HPLC column (25 cm × 4.6 mm ID, packed with Spherisorb, 5 µm particle size) |
| Loop: | 1 ml |
| Flow: | 1.5 ml/min. |
| Solvent: | linear gradient, below |
| Fraction: | 1 ml/tube |
| Detector Absorption Setting: | 205 nm, 232 nm |
| Linear Gradient | (See, Section 6.15, below) |

It will also be apparent to one of ordinary skill in the art, after considering the disclosure presented herein, that other HPLC conditions can be contemplated and applied to the separation and purification of the active substances of the present invention. In particular, reverse-phase conditions can also be utilized to good advantage. See, for example, Rice, K. G. et al., supra.

Again, without wishing to be limited by theory, it is suspected that the activity of TNF-α is augmented by either increasing the intracellular production of active TNF-α, increasing the amount of active TNF-α secreted by the host's immune effector cells, or enhancing the activity of the cytokine through the action of an agonist.

It also follows that the biological activity of TNF-α may be inhibited by converse processes, including not only competition offered by the active inhibitory substance for the receptors of TNF-α (e.g., the inhibitory substance acting as or inducing the production of another substance that acts as an antagonist of TNF-α) but also the formation of a complex of TNF-α and the inhibitory substance which is less active than free TNF-α. Alternatively, it follows that a "souped-up" complex between TNF-α and the augmentative substance may be responsible for the observed increase in the activity of TNF-α.

4.5. Determination of Activity

The active substances of the present invention, both those able to inhibit TNF-α activity and those able to augment TNF-α activity, have been isolated and purified from mixtures containing them. In some cases, these active substances have been purified to substantial homogeneity by the powerful HPLC techniques described herein.

As a further indication of the purity of these active substances, the specific regulatory activities of the various substances were determined.

Initially, however, a carbazole assay, performed in a manner similar to that disclosed by Carney, S. L. in *Proteoplycan Analysis A Practical Approach*, Chaplin, M. F. and Kennedy, J. F. (Eds.) IRL Press, Oxford, Washington, D.C. (1986) p. 129, was utilized to determine the amount of oligosaccharide material present (e.g., amount of sugar present) in a given test sample. Picogram (pg) quantities of sugar can be quantified in this manner. The assay is performed as described in Section 5, below.

Next, the apparent activity associated with that quantity of substance is determined by one of the biological assays that are described in great detail in Section 5, below, to provide a dose/response profile. These bioassays may either be carried out in vitro or under in vivo conditions.

Figure 9:
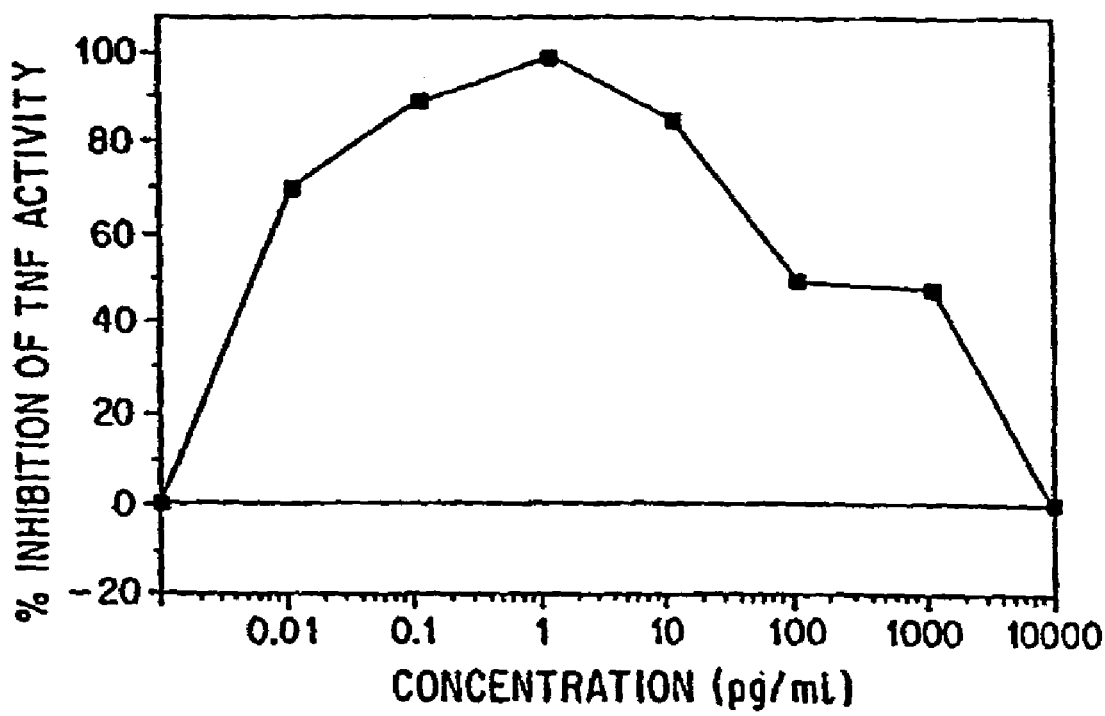
FIG. 9 illustrates the "bell-shaped" dose to response curve exhibited by active Fragmin.

It has, thus, been found that the observed inhibition or augmentation of TNF-α activity, expressed as a percentage of the activity of TNF-α observed in the absence of the substances of the present invention, depends on the concentration or dose of such substance present in the test sample. The apparent activity profile that results is approximately bell-shaped as illustrated in FIGS. 9 and 16. The maximum value of percent inhibition or augmentation observed for each substance is designated $Inh_{max}$ or $Aug_{max}$, as the case may be.

As described further, below, the bioassay used to establish the "ideal" unit dose (i.e., the one It that corresponds to $Inh_{max}$ or $Aug_{max}$) can be based on the in vitro or in vivo inhibition or augmentation of the activity of TNF-α or DTH assay in mice. Alternatively, an in vitro assay based in human cells (described further, below) may also be used. The specific regulatory activity or "R" value is, as defined herein, the ratio of the $Inh_{max}$ or $Aug_{max}$ and the "ideal" dose that gave rise to that maximum percent inhibition or augmentation. For the in vitro assays, the "R" values are typically expressed in units of $\%\times(pg/ml)^{-1}$.

As stated above, the specific regulatory activity can also be established under in vivo conditions by monitoring the inhibition of experimental DTH reaction in mice or humans. It was found that the ability of a particular dose of an inhibitory composition to inhibit secretion of active TNF-α is positively correlated with its ability to inhibit the delayed type hypersensitivity (DTH) reaction, although the same composition may be more potent under one assay versus another (i.e., between in vitro and in vivo bioassays). Inhibitory or augmenting activity in this in vivo cell-mediated inflammatory reaction is of great importance because the DTH reaction is an expression of the processes involved in autoimmune diseases, graft rejection, some types of blood vessel inflammation and allergy. Thus, activity in this test is indicative of utility in these types of diseases and possibly others, as described further below.

Moreover, the new quantity, the specific regulatory activity, which is defined as the ratio between the $Inh_{max}$ or $Aug_{max}$ value and the amount or concentration of substance (the "ideal" dose) which gave rise to that maximum percent value, can serve to distinguish the novel active substances of the present invention from those substances that may have been known, but unrecognized in the art as possessing the cytokine regulatory activity disclosed herein. This specific ratio is referred to herein as the "R" value, for short. Hence, the novel substances or compositions of the present invention can be described in terms of a minimum "R" value, which can be calculated from the apparent activity versus dose profile, and which "R" value will exceed the "R" value that can be associated, by reference to the teachings of the present disclosure, with known compositions.

4.6. Types of Disorders That May Benefit From the Present Invention

The disorders that can be prevented or treated according to the invention are all disorders linked to pathological processes-involving induction of active TNF-α secretion, including atherosclerosis and vasculitis and pathological processes related thereto; autoimmune diseases, e.g., rheumatoid arthritis, diabetes type I (insulin-dependent diabetes mellitus or IDDM), multiple sclerosis, lupus erythematosus, Graves disease; allergy; graft rejection; acute and chronic inflammatory diseases, e.g. uveitis, bowel inflammation; anorexia nervosa; hemorrhagic shock caused by septicemia, and HIV infection in AIDS. In AIDS, the active substances will suppress replication of HIV thereby preventing the development of AIDS-related complex (ARC). Other disorders that may benefit from a treatment designed to regulate cytokine activity include, but are not limited to, psoriasis, pemphigus, asthma, renal diseases, liver diseases, bone marrow failure, vitiligo, alopecia, and myositis.

Further, augmentation of active TNF-α is useful in the treatment of tumors, bacterial infections and viral infections. Parenteral, oral or topical administration of the substances of the present invention which augment the production of active TNF-α in a pharmaceutically acceptable carrier may also help combat skin cancer, such as basal cell cancer, squamous cell cancer, or melanoma.

In the clinical application of the active substances of the present invention, it should be kept in mind that the successful treatment of certain types of disease consists, in large part, in the restoration of homeostasis. To the endocrinologist, this implies the judicious administration or antagonism of specific hormones. For example, an insulin-dependent diabetic may be effectively treated by insulin replacement therapy; a patient with Graves' disease may be helped by pharmacological measures that inhibit thyroxine release. Only rarely can disease be alleviated by administration of hormones that were never deficient to begin with.

The use of cytokines, such as TNF-α, as antineoplastic agents provides one such instance. The rationale for administration of immunomodulatory agents to cancer patients may be quite slender. Many cytokines, like TNF-α, exhibit toxicities that prove dose-limiting long before a therapeutic goal is achieved. In such an event, the augmentation of the activity of endogenously produced TNF-α may provide an approach that is both novel and, eventually, prove more effective than any previously contemplated therapeutic regimen.

Clearly, our understanding of the role for TNF-α is still evolving and, doubtless, new and useful uses of the hormone and the substances able to regulate its activity will be uncovered. While it goes without saying that all uses of the claimed compositions and pharmaceutical preparations are within the scope of the present invention, those uses that either alleviate the symptoms of disease, prevent the onset of disease, or provide a cure for the disease are especially contemplated.

4.7. Topical Applications of the Oligosaccharide Substances of the Present Invention The substances of the present invention also find use in topically administered compositions, such as those preparations for the treatment of edema or inflammation. Indeed, above and beyond a purely therapeutic application, the substances of the present invention may also find utility in supplementing the protective action of cosmetic compositions, such as sunscreen or suntan lotions. Few, if any, sunscreen preparations are fully effective in blocking out all the harmful wavelengths (e.g., 290-320 nm) present in the ultraviolet region of the electromagnetic spectrum. Hence, overexposure to the sun often gives rise to an acute condition known as solar erythema and prolonged, repeated exposure can, of course, lead to leathery looking skin or, worse, skin cancer.

Thus, the incorporation of the active substances of the present invention in cosmetic preparations is specifically contemplated both for the purpose of preserving and protecting the skin, as well as alleviating a medical condition, such as solar erythema. In sunscreen or suntan preparations, it would be advantageous to include an effective amount of the oligosaccharides of the present invention along with conventional sunscreen agents. Generally, an amount of active substance would be present to provide a dose of about 1 μg to about 100 mg per kilogram of subject, preferably from about 0.01 mg to about 10 mg per kilogram of subject, and most preferably about 0.1 mg to about 1 mg per kilogram of subject.

The cosmetic compositions, may contain conventional ingredients known to those of ordinary skill in the art, such as those described in *Kirk-Othmer, Encyclopedia of Chemical Technology, Third Edition* (1979), Vol. 7; pp. 143-176. In sunscreen preparations, the addition of the active substances of the present invention increases the minimum erythemal dose (MED) and, consequently, the sun protection factor (SPF). Specific ingredients, including typical sunscreens, are listed in *Kirk-Othmer*, supra, at pp. 153-154. In addition, topical preparations and cosmetic formulations may be prepared as described in U.S. Pat. Nos. 4,199,576, 4,136, 165, and 4,248,861, the complete disclosures of which are incorporated by reference herein. It would, of course, be apparent to those of ordinary skill in the art of cosmetology that the resulting compositions can be in many forms, including, but not limited to, solutions, lotions, cremes, pastes, emulsions, sprays, or aerosols.

4.8. Exemplary Dosage Regimens

It was thus established according to the invention that the lowest dose of LMWH per kg causing inhibition of TNF-α, production or inhibition of DTH reactivity by at least 50% is considered to constitute 12 mouse inhibitory units per kg (12 u/kg). Because of the differences in surface area and metabolism between mice and humans, humans should be treated with a lower dose of LMWH, and 12 u/kg in mice is established to correspond to 1 u/kg in humans. For example, the dose of Fragmin® batch 38609 effective in inhibiting both TNF-α secretion and DTH reactivity is 5 μg per mouse administered weekly. Since each mouse weighs about 25 g, the dose of Fragmin® 38609 equivalent to 12 u/kg is 200 μg/kg of mouse. The dose of 1 u/kg suitable for humans is therefore 200 μg/kg÷12=16.67 μg/kg. A human weighing about 70 kg would then be treated by a dose of about 1.2 mg given in a single dose subcutaneously once every 7 days. Since individual humans vary biologically, the optimal dose may be different from about 1.2 mg and will lie generally below 5 mg, particularly within the range of 0.3 to 3 mg.

Hence a rough guide for conversion of the mice dosage regimen to human dosage is the following:

Dose Human/kg=Dose Mouse/kg÷10 or 12

The dose of LMWH that should be effective in rats can be derived from the fact that the dose of LMWH per kg of rats is one-half the dose per kg of mice, i.e. 6 u/kg. For example, if 12 u of Fragmin® batch 38609 is 200 μg/kg, then the 6 u dose suitable for rats should be 100 µg/kg or 20 µg per 200 g rat, administered once a week.

For most of the oligosaccharide substances of the present invention, which have been isolated from LMWH, degraded heparin and degraded ECM, the following is a way to predict the effective dose of these oligosaccharide substances for treatment of humans from the in vivo DTH bioassay.

Figure 12A:
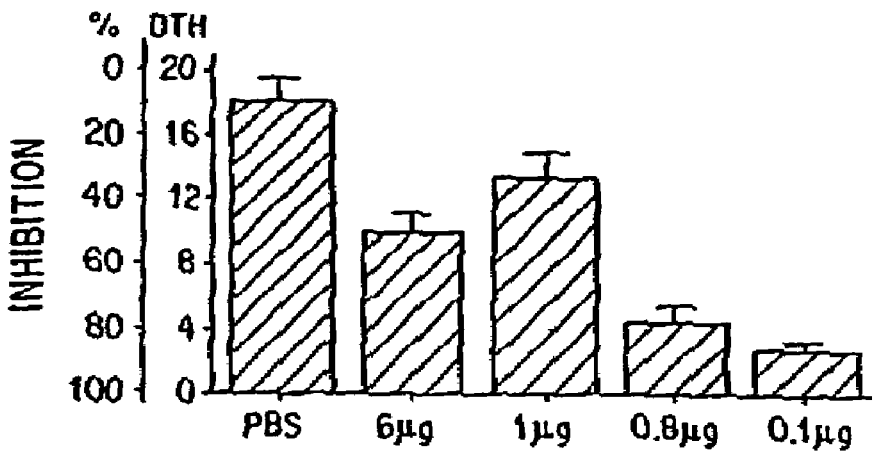
Figure 12B:
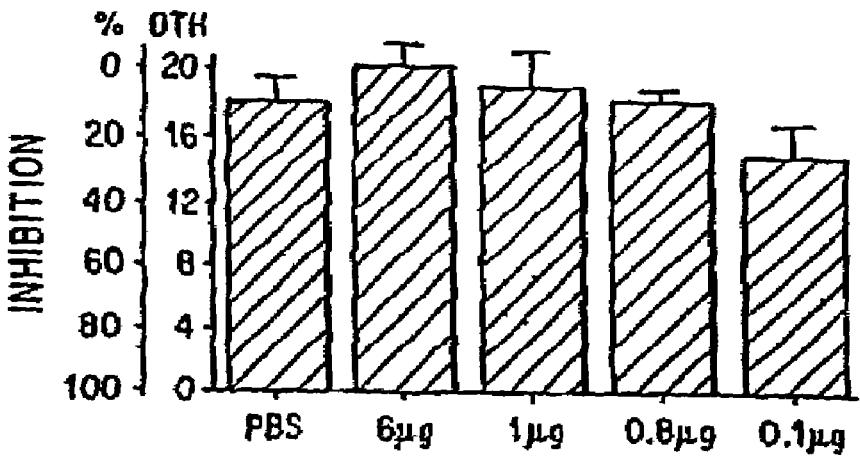

FIG. 12A shows that an isolated fraction (F15) in vivo inhibits the DTH in mice at a range of 0.1-5.0 µg/mouse/ week. Since our mice weigh 25 gm, the in vivo dose is approximately (0.1÷0.025 kg) 4-200 µg/kg mouse/week (the equivalent of 0.01-10 pg/ml in vitro).

To correct for the surface area difference between mice and humans, we have to divide the mouse dose/kg by 12:

4-200 µg/kg mouse→0.33-16.67 µg/kg human.

Thus, a 70 kg human should receive up to about 1.2 mg (about 1,200 µg). To be certain that we could cover the difference between people, we might increase this dose to about 5 mg, an amount that is well below any doses of heparinoids used for their effects on coagulation or thrombosis. Hence, the dose for a 70 kg human, will be about 5 mg or less, preferably about 3 mg or less, more preferably about 1.5 mg or less, and most preferably about 1 mg or less.

In fact for the highly purified materials of the present invention, including those that have been obtained from HPLC chromatography, the preferred dosages may be even less. For example, the disaccharides, described in greater detail below, have been found to exhibit inhibitory activity, when administered by injection, at about 0.1 µg to about 0.5 µg per kilogram mouse. Hence, the dosage for humans are estimated to be about 0.01 µg to about 0.05 µg per kilogram man or about 0.7 µg to about 3.5 µg for a 70 kilogram man for the purified disaccharides. A general range of dosage for a 70 kg man, then, may be about 0.1 µg to about 100 µg, preferably about 1 µg to about 10 µg for the disaccharides. The dosages may be somewhat higher for the known disaccharide "markers," discussed further below.

The doses recited above may be given a number of times a day or at daily, weekly or even greater intervals depending on the responsiveness of the individual. For the LMWHs, however, the dosage interval is preferably weekly, as stated previously.

The invention will now be illustrated by the following non-limiting examples.

5. Experiments Using LMWH (Fragmin) Only 5.1. Bioassay of Inhibition of Active TNF-α Secretion Using House Spleen Cells Supernatants of spleen cells cultured in the presence or absence of LMWH, or spleen cells obtained from mice treated or untreated with LMWH in vivo are analyzed for their ability to secrete active TNF-α. The TNF-α bioassay is based on the cytotoxic effect of TNF-α on cycloheximide (CHI)-sensitized cells and its quantitation by the neutral red uptake assay as described by Wallach D., *J. Immunol.* (1984) 132:2464-2469. Briefly, the killing of CHI-sensitized HeLa cells by TNF-α present in the supernatants of the cells is measured, the concentration of TNF-α in the supernatants being determined by comparison to titration curves of TNF-α exogenously added. Cell viability is determined by incubation with neutral red for two hours, washing away excess dye, extracting the neutral red that was taken up by the cells with Sorenson's citrate buffer-ethanol mixture, and quantitating it calorimetrically at 570 nm with a Microelisa Autoreader.

Cells from mice treated with LMWH are obtained as follows: female mice of the BALB/c strain (25 grams, 2 months old), at least 5 mice per group, are injected subcutaneously with various doses of LMWH, usually in the range of 0.5 to 20 µg per mouse. Five days later the mice are killed by cervical dislocation, the spleens are removed and suspensions of spleen cells, depleted of red blood cells, are assayed for the production of TNF-α in response to induction by residual extracellular matrix (RECM), Concanavalin A (Con A) or lipopolysaccharide (LPS).

5.2. In Vivo Bioassay of Inhibition of Experimental DTH Reactivity

Groups of inbred BALB/c (Jackson Laboratories, Bar Harbor, Me.) or of outbred CD1 (Weizmann Institute Animal Breeding Center, Rehovot, Israel) mice are sensitized on the shaved abdominal skin with 100 µl of 2% oxazolone (OX) in acetone/olive oil (4/1, v/v) applied topically. DTH sensitivity is elicited 5 days later as follows: mice are challenged with 20 µl of 0.5% OX (10 µl administered topically to each side of the ear) in acetone/olive oil. A constant area of the ear is measured immediately before challenge and 24 and 48 h later with a Mitutoyo engineer's micrometer. The individual measuring ear swelling is blinded to the identity of the groups of mice. The increment (Δ) of ear swelling is expressed as the mean in units of $10^{-2}$ mm or $10^{-4}$ inch (+SE) depending on the micrometer that is used. Percent inhibition is calculated as follows:

$$\% \text{ Inhibition} = 1 - \left( \frac{\text{Treated} - \text{negative control}}{\text{positive control} - \text{negative control}} \right)$$

Mice are treated with LMWH again Example 5.1, injected the day before primary sensitization to OX. On the fifth day after sensitization to OX, the 10 mice are challenged to induce a DTH reaction, as described above.

The positive control is the DTH reaction elicited in immunized mice in the absence of treatment with LMWH. The negative control is the background swelling produced by the antigen in naive (non-immunized) mice.

5.3. Induction of TNF-α Secretion by T Cells and Macrophages In Vitro

Microtiter plates were prepared as follows:

fibronectin (FN) or laminin (LN) (sigma) were added to flat bottom 96-well plates (Costar) at a concentration of 1 µg/50 µl PBS per well and removed after 16 h. Remaining binding sites were blocked with BSA/PBS (10 mg/ml) which was added to the wells for 2 h and washed out.

ECM-coated wells were prepared as follows:

bovine corneal endothelial cells were cultured in flat bottom 96-well plates. The confluent layers of endothelial cells were dissolved and the ECM was left intact free of cellular debris (Gospodarowicz, D. et al., *J. Biol. Chem.* (1978) 253:3736). Disrupted or residual ECM (RECM) was prepared by gently scratching the ECM three times with a 27 G syringe needle and the exposed sites were subsequently coated with BSA/ PBS. Resting cloned rat CD4$^+$ T cells, designated K1, which recognize myelin basic protein (MBP), were propagated and maintained in culture and were added to the wells, $10^5$ cells per well with or without $3 \times 10^5$ syngeneic splenic macrophages, in 100 µl per well RPMI 1640 (Gibco) supplemented with 1% BSA and antibiotics.

The splenic macrophages were purified by removing the T and B cells using specific monoclonal antibodies (mAb). Anti-murine TNF-α mAb was obtained from Genzyme (Cambridge, Mass.), and was diluted 300-fold. A 10 µl aliquot of this diluted solution was added to each well. MBP (100 µg/ml), Con A (2.5 µg/ml), LPS (1 µg/ml), FN (5 µg/ml), and LN (5 µg/ml) were added to the wells where indicated.

The plates were incubated at 37° C. in a humidified incubator for 3 h. Subsequently, the contents of the wells (4 wells per experimental group) were collected, centrifuged, and the media were assayed for active TNF-α secretion as in the example described in Section 5.1: That is, supernatants of cultured macrophages and lymphocytes were added to cultures of HeLa cells, which are sensitive to killing by TNF-α, and death of these cells in the presence of the test media was calibrated in comparison to titration curves of exogenous added TNF-α. Cell death is examined by the release of neutral red dye from the preincubated HeLa cells. The results shown here represent data obtained from a total of six experiments that produced essentially similar results.

Table V shows that T cells and macrophages cultured together can be induced to secrete TNF-α by contact with specific antigen MBP (group 4), the mitogen Con A (group 6) or LPS (group 8). However, in the absence of antigenic or mitogenic stimulus, the secretion of TNF-α was also induced by residual extracellular matrix (RECM; group 10) or by the ECM components, fibronectin (FN; group 12) or laminin (LN group 14). Intact ECM was a weak inducer of TNF-α (group 16).

TABLE V

TNF-α secretion by T cells and macrophages is induced by specific antigen MBP, Con A, LPS, RECM, or ECM components.

| Group | TNF-α inducer | K1 cells cultured together with (yes) or without (no) macrophages | Secreted TNF-α (pg/ml) |
|---|---|---|---|
| 1 | none | no | 50 |
| 2 |  | yes | 65 |
| 3 | MBP antigen | no | 30 |
| 4 |  | yes | 950 |
| 5 | Con A | no | 120 |
| 6 |  | yes | 1300 |
| 7 | LPS | no | 50 |
| 8 |  | yes | 1500 |
| 9 | RECM | no | 30 |
| 10 |  | yes | 900 |
| 11 | FN | no | 20 |
| 12 |  | yes | 650 |
| 13 | LN | no | 50 |
| 14 |  | yes | 500 |
| 15 | ECM | no | 30 |
| 16 |  | yes | 120 |

5.4. Regulation of TNF-α Secretion by LMWHs

T cell and accessory cell cultures were prepared as described in Section 5.3. LMWH was added to the wells at the beginning of the cell culture. The levels of TNF-α were examined after 3 h of incubation.

Table VI shows that the presence of LMWH (Fragmin® batch 38609) in vitro inhibited active TNF-α secretion induced by specific antigen (MBP; group 4), mitogens (Con A and LPS; groups 6 and 8), RECM or ECM components (groups 10, 12 and 14). Since TNF-α secretion induced by RECM is likely to be involved in atherosclerosis, inhibition of TNF-α by LMWH will be beneficial in atherosclerosis.

TABLE VI

Induction of TNF-α secretion induced in vitro is inhibited by LMWH (Fragmin ® batch 38609).

| Group | TNF-α Inducer | LMWH (1 µg/ml) | Secretion of TNF-α by cultures of T cells and macrophage (pg/ml) |
|---|---|---|---|
| 1 | none | none | 65 |
| 2 |  | yes | 30 |
| 3 | MPB antigen | none | 950 |

TABLE VI-continued

Induction of TNF-α secretion induced in vitro is inhibited by LMWH (Fragmin ® batch 38609).

| Group | TNF-α Inducer | LMWH (1 µg/ml) | Secretion of TNF-α by cultures of T cells and macrophage (pg/ml) |
|---|---|---|---|
| 4 |  | yes | 60 |
| 5 | Con A | none | 1300 |
| 6 |  | yes | 80 |
| 7 | LPS | none | 1500 |
| 8 |  | yes | 80 |
| 9 | RECM | none | 900 |
| 10 |  | yes | 90 |
| 11 | FN | none | 650 |
| 12 |  | yes | 90 |
| 13 | LN | none | 500 |
| 14 |  | none | 70 |

5.5. Ex Vivo Experiments with LMWH-Treated BALB/c Mice

To examine the effect of LMWH administered to mice in vivo on the secretion of TNF-α by spleen cells in vitro, the following experiment was conducted. BALB/c mice, 5 per group, were treated with various doses of LMWH (Fragmin batch 38609) diluted in saline, injected subcutaneously. After one week, the animals were killed and their spleen cells, devoid of red blood cells, were examined for their ability to secrete TNF-α in response to control wells without RECM (A) or to wells coated with RECM (B). Measuring the levels of TNF-α secretion was done as described in Section 5.1. Table VII shows the results which indicate that an injection of 5 µg of LMWH given once, 7 days earlier, inhibited TNF-α secretion induced by RECM. Higher or lower doses of LMWH were less effective. Thus, an optimal dose of LMWH administered in vivo a week earlier was effective.

TABLE VII

Ex vivo inhibition of T cell mediated TNF-α secretion in response to residual ECM.

| | LMWH treatment of BALB/c mice (weekly) | In vitro TNF-α secretion (pg/ml) by spleen cells cultured on: | |
|---|---|---|---|
| | | A. None | B. Residual ECM (% Inhibition) |
| 1 | None | 30 | 400 — |
| 2 | 0.5 µg | 50 | 380 (5) |
| 3 | 1 µg | 25 | 90 (78) |
| 4 | 5 µg | 25 | 60 (85) |
| 5 | 10 µg | 30 | 140 (65) |
| 6 | 20 µg | 40 | 320 (20) |

Table VIII shows that a 5 µg dose in vivo of LMWH Fragmin® batch 38609 was also effective in inhibiting TNF-α secretion induced by LPS. BALB/C (4 mice per experimental group) mice were treated with the indicated amounts of LMWH diluted in saline and injected subcutaneously. After one week, the mice were injected intraperitoneally with 10 mg LPS, killed 4 hours later and their spleen cells, devoid of red blood cells, were subsequently cultured in RECM coated wells for 3 hours in a humidified incubator. The levels of TNF-α secreted in response to the RECM was measured in the supernatants of the cultures. The results are given in Table VIII.

TABLE VIII

Treatment of mice with LMWH inhibits LPS mediated secretion of active TNF-α by macrophages.

| LMWH treatment of mice (μg) | In vitro TNF-α secretion by macrophages (pg/ml) in response to LPS | % Inhibition |
|---|---|---|
| 0 | 690 | — |
| 0.1 | 500 | 28 |
| 1 | 350 | 50 |
| 5 | 120 | 82 |
| 20 | 550 | 20 |

5.6. Experiments Using a Variety of LMWH Sources

To examine the effect of different LMWHs on the inhibition of secretion of active TNF-α and on DTH responses, mice were treated with the indicated LMWH administered subcutaneously in different concentrations. After one week, some of the mice were killed and the induction of secretion of active TNF-α in response to Con A activation in vitro was measured (Table IX). The remaining mice were examined for their ability to respond to the antigen oxazolone (Table X). The results are expressed in the Tables as percent inhibition compared to the responses of the LMWH untreated mice.

Two conclusions can be made by inspecting the results shown in Table IX and Table X:

1. Different batches of LMWH, each calibrated for by similar antithrombotic effect (Factor X assay) have different optimal doses for inhibition of secretion of active TNF-α. Moreover, there are preparations of LMWH, such as Clexane® batch 4096, which have no inhibitory effect on secretion of active TNF-α, at any of the doses tried. Therefore, it may be concluded that the antithrombotic effect of a LMWH preparation is not related to the potential of the LMWH preparation for inhibition of secretion of active TNF-α. The two different bioassays are mediated by different factors present in the preparations.

2. The ability of a particular dose of LMWH to inhibit secretion of active TNF-α is positively correlated with its ability to inhibit DTH reaction, and the dose of a LMWH preparation optimally effective in inhibiting secretion of active TNF-α is also optimally effective in inhibiting the DTH reaction.

TABLE IX

Weekly Treatment of Mice with Different LMWHs Inhibits DTH Sensitivity of Mice.

| Batch of LMWH | Dose (μg/gm mouse) | DTH Response ($10^{-2}$ mm) | Inhibition of DTH (%) | "R" value % × (μg/gm)$^{-1}$ |
|---|---|---|---|---|
| Fragmin | | | | |
| Batch 38609 | None | 25 | (+) Control | — |
| | | 2 | (−) Control | — |
| | 0.02 | 21 | 12 | — |
| | 0.04 | 23 | 10 | — |
| | 0.2 | 6 | 73 (max) | 365 |
| | 0.4 | 6 | 20 | — |
| | 2 | 0 | 0 | — |
| Batch 45389 | None | 28 | (+) Control | — |
| | | 2 | (−) Control | — |
| | 0.004 | 26 | 6 | — |
| | 0.04 | 4 | 89 (max) | 2225 |
| | 0.2 | 24 | 13 | — |
| | 0.4 | 26 | 6 | — |
| | 2 | 29 | 0 | — |
| Clexane | | | | |
| Batch 2088 | None | 22 | (+) Control | — |
| | | 2 | (−) Control | — |
| | 0.004 | 17 | 23 | — |
| | 0.04 | 3 | 87 (max) | 2175 |
| | 0.2 | 13 | 41 | — |
| | 0.4 | 23 | 0 | — |
| Batch 2066 | None | 23 | (+) Control | — |
| | | 2 | (−) Control | — |
| | 0.004 | 20 | 13 | — |
| | 0.04 | 8 | 65 | — |
| | 0.2 | 7 | 70 (max) | 350 |
| | 0.4 | 7 | 70 | — |
| Batch 4096 | None | 24 | (+) Control | — |
| | | 2 | (−) Control | — |
| | 0.04 | 27 | No effect | 0 |
| | 0.2 | 26 | No effect | 0 |
| | 0.4 | 24 | No effect | 0 |

TABLE X

Weekly Treatment of Mice with Different LMWHs Inhibits Ex Vivo Secretion of Active TNF Using Mouse Spleen Cell Bioassay.

| Batch of LMWH | Dose (μg/gm mouse) | Con A-Induced TNF secretion (pg/ml) | Inhibition (%) | "R" value % × (μg/gm)$^{-1}$ |
|---|---|---|---|---|
| Fragmin | | | | |
| Batch 38609 | None | 450 | Control | — |
| | 0.02 | 425 | 5 | — |
| | 0.04 | 400 | 12 | — |
| | 0.2 | 68 | 85 (max) | 425 |
| | 0.4 | 350 | 22 | — |
| | 2 | 435 | 8 | — |
| Batch 45389 | None | 320 | Control | — |
| | 0.004 | 280 | 13 | — |
| | 0.04 | 70 | 78 (max) | 1950 |
| | 0.2 | 260 | 18 | — |
| | 0.4 | 290 | 10 | — |
| | 2 | 310 | 4 | — |
| Clexane | | | | |
| Batch 2088 | None | 400 | Control | — |
| | 0.004 | 360 | 10 | — |
| | 0.04 | 64 | 84 (max) | 2100 |
| | 0.2 | 152 | 38 | — |
| | 0.4 | 380 | 4 | — |
| Batch 2066 | None | 350 | Control | — |
| | 0.004 | 338 | 6 | — |
| | 0.04 | 185 | 54 | — |
| | 0.2 | 192 | 57 (max) | 285 |
| | 0.4 | 186 | 55 | — |

TABLE X-continued

Weekly Treatment of Mice with Different LMWHs Inhibits Ex Vivo Secretion of Active TNF Using Mouse Spleen Cell Bioassay.

| Batch of LMWH | Dose (µg/gm mouse) | Con A-Induced TNF secretion (pg/ml) | Inhibition (%) | "R" value % × (µg/gm)$^{-1}$ |
|---|---|---|---|---|
| Batch 4O96 | None | 320 | Control | — |
| | 0.04 | 335 | No effect | 0 |
| | 0.2 | 325 | No effect | 0 |
| | 0.4 | 330 | No effect | 0 |

5.7. Treatment of Adjuvant Arthritis (AA) in Rats With Low Doses of LMWHs

Adjuvant arthritis is an experimental disease inducible in some strains of rats by immunizing them to antigens of Mycobacterium tuberculosis (Pearson, C. M., *Proc. Soc. Exp. Biol. Med.* (1956) 91:91). This experimental disease is considered to be a model of human rheumatoid arthritis (Pearson, C. M., *Arthritis Rheum.* (1964) 7:80). The arthritis appears to be caused by T lymphocytes that recognize an antigen of M. tuberculosis that is cross-reactive with structures in the joint tissues (Cohen, I. R., et.al., *Arthritis Rheum.* (1985) 28:841).

Lewis rats were immunized with M. tuberculosis (1 mg) in oil to induce adjuvant arthritis (Pearson, C. M., *Proc. Soc. Exp. Biol. Med.* (1956) 91:91). Five days later the rats were inoculated subcutaneously as indicated with the doses of LMWH and/or heparin and scored for the development of arthritis on a scale of 0-16 as described (Holoshitz, J., et al., *Science* (1983) 219:56). All the experiments were performed with Fragmin®, Batch 38609.

In order to study the dose response to Fragmin® (FIG. 1) rats immunized to induce AA were injected subcutaneously weekly, starting on the 5th day after injection with 0.5 µg (○), 1 µg (◆), 2 µg (●), 10 µg (◇), 15 µg (△) 20 µg (■); 30 µg (▲), 40 µg (×) and PBS control (□). The 20 µg dose was maximally effective in inhibiting arthritis.

Figure 2:
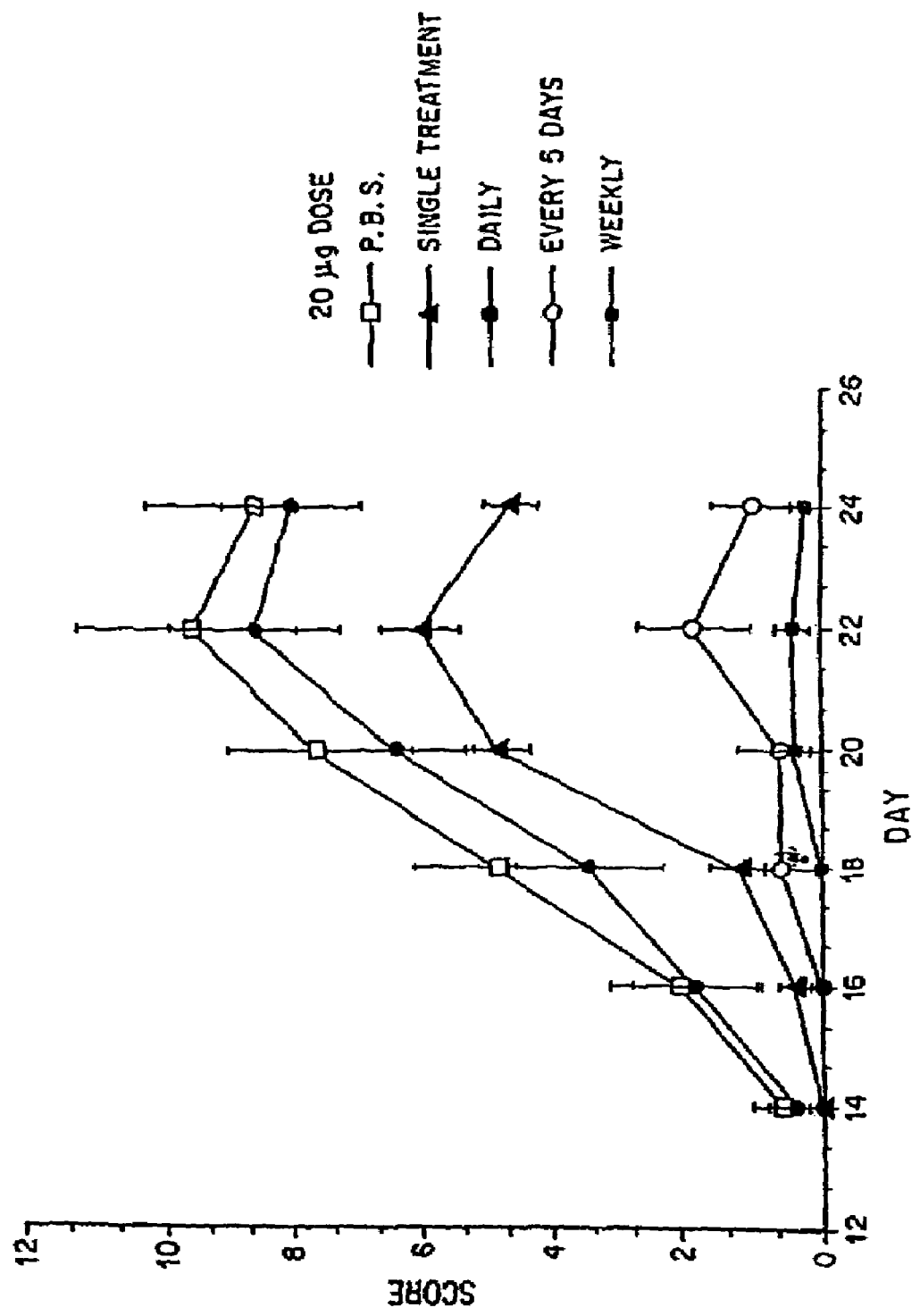
FIG. 2 illustrates the AA scores obtained from groups of rats which received a constant 20 microgram dose of Fragmin under various dosage regimens, including single treatment, daily treatment, five day intervals, and weekly.

The effect of the 20 µg dose of Fragmin® on the course of AA is shown in FIG. 2: PBS control, (□); single treatment on 5th day (▲); daily (●); every 5th day (○); weekly (■). It is shown that Fragmin administration both at 5 day intervals and at 7 day intervals inhibits arthritis.

Figure 3:
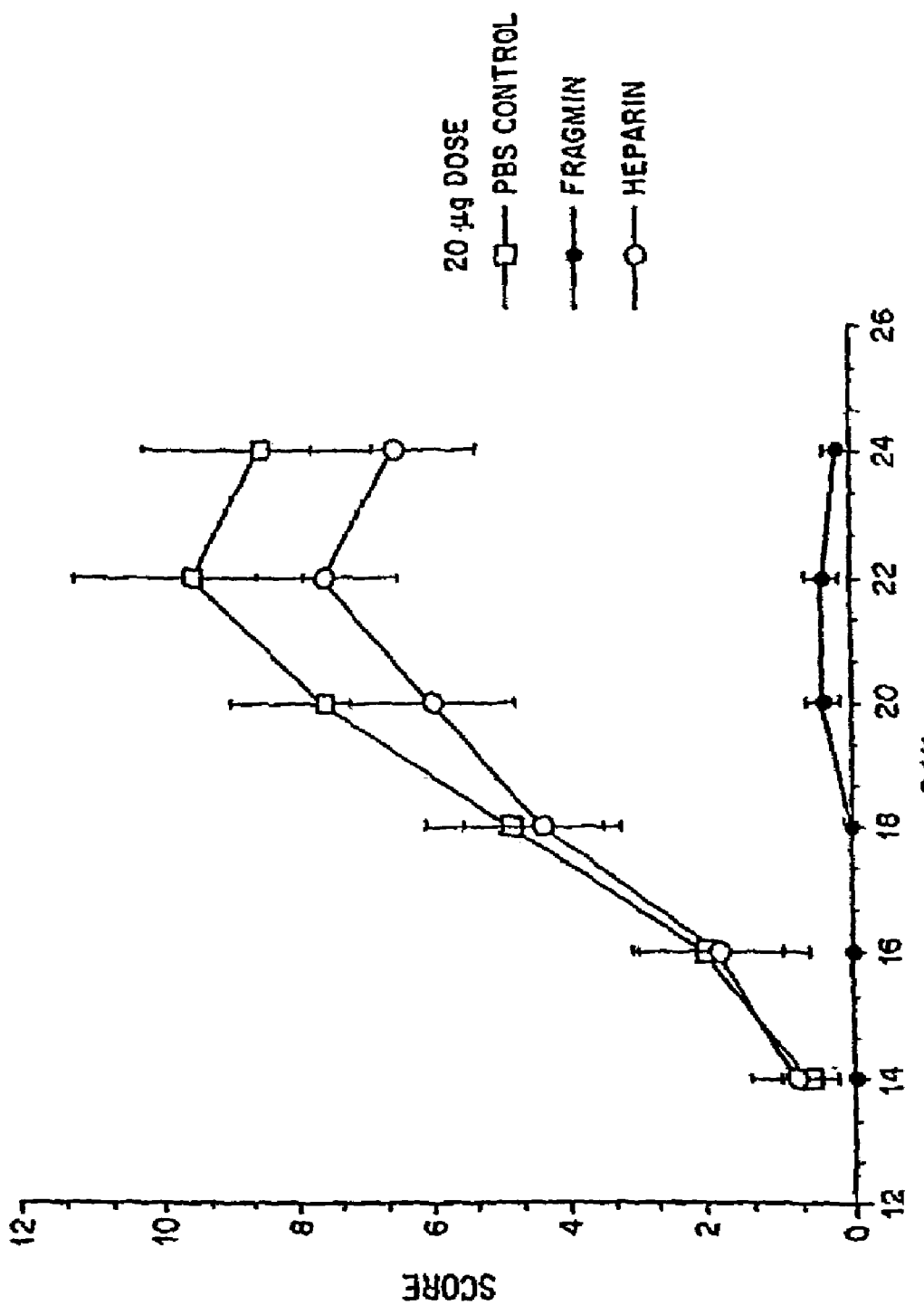
FIG. 3 compares the effectiveness of weekly administration of Fragmin versus Heparin and control (PBS).

FIG. 3 shows the effect of weekly administration of Fragmin® (batch 38609) as compared to standard heparin on AA. Lewis rats were immunized to induce AA. Beginning on day 5, the rats were inoculated subcutaneously at weekly intervals with a 20 µg dose of Fragmin® (●), heparin (○) or phosphate buffered saline (PBS) control (□). The results show a dramatic difference in potency between Fragmin® and heparin: Fragmin® completely inhibited arthritis, while heparin had no inhibitory effect.

Figure 4:
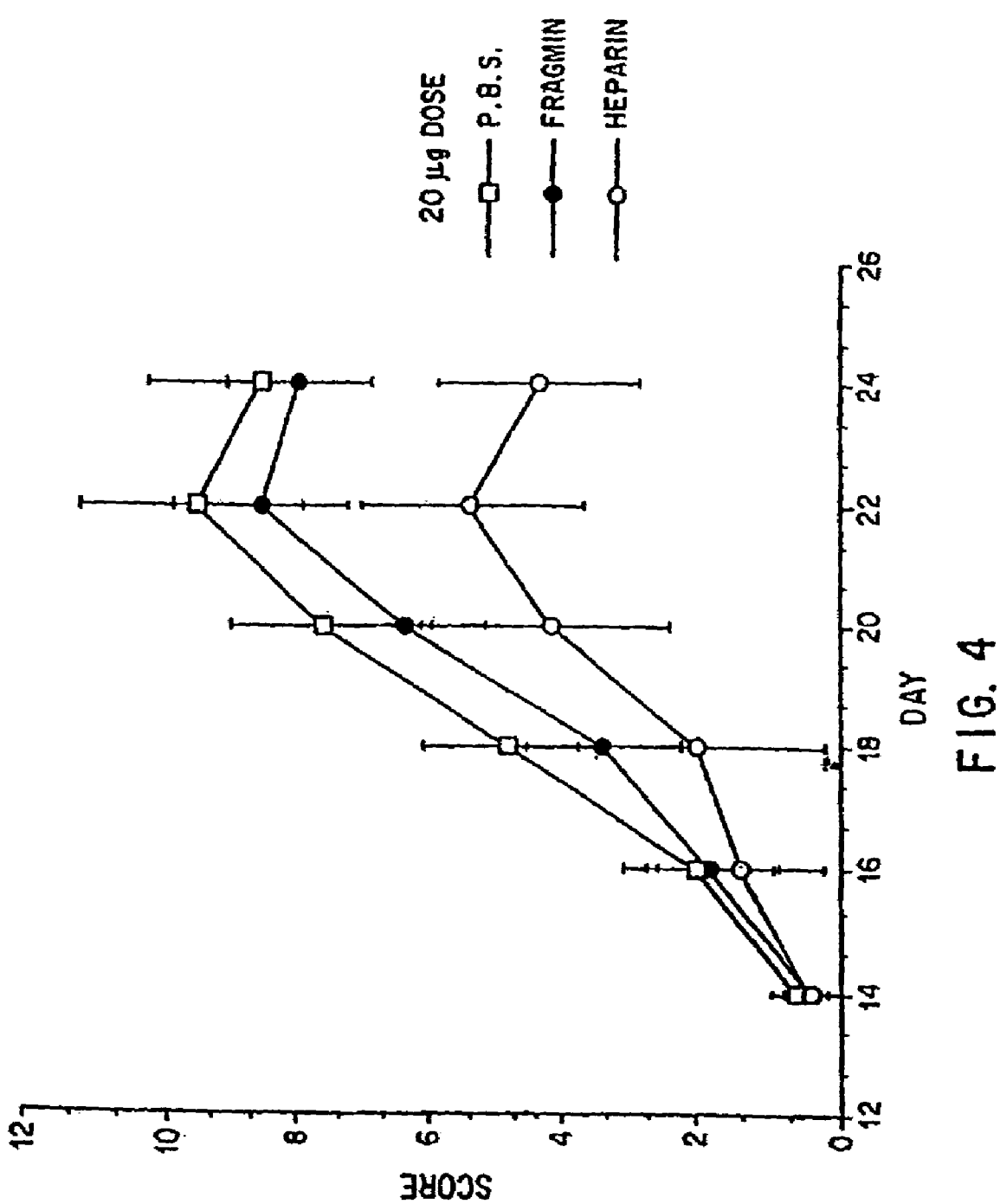
FIG. 4 illustrates the results of daily administration of Fragmin, Heparin or PBS.

No inhibitory effect on AA was found with daily administration of a 20 µg dose of LMWH, although surprisingly the inhibitory effect of heparin was stronger than that of Fragmin® in daily administration, as shown in (FIG. 4: Fragmin® (batch 38609)(●), heparin (○), PBS control (□)).

Figure 5:
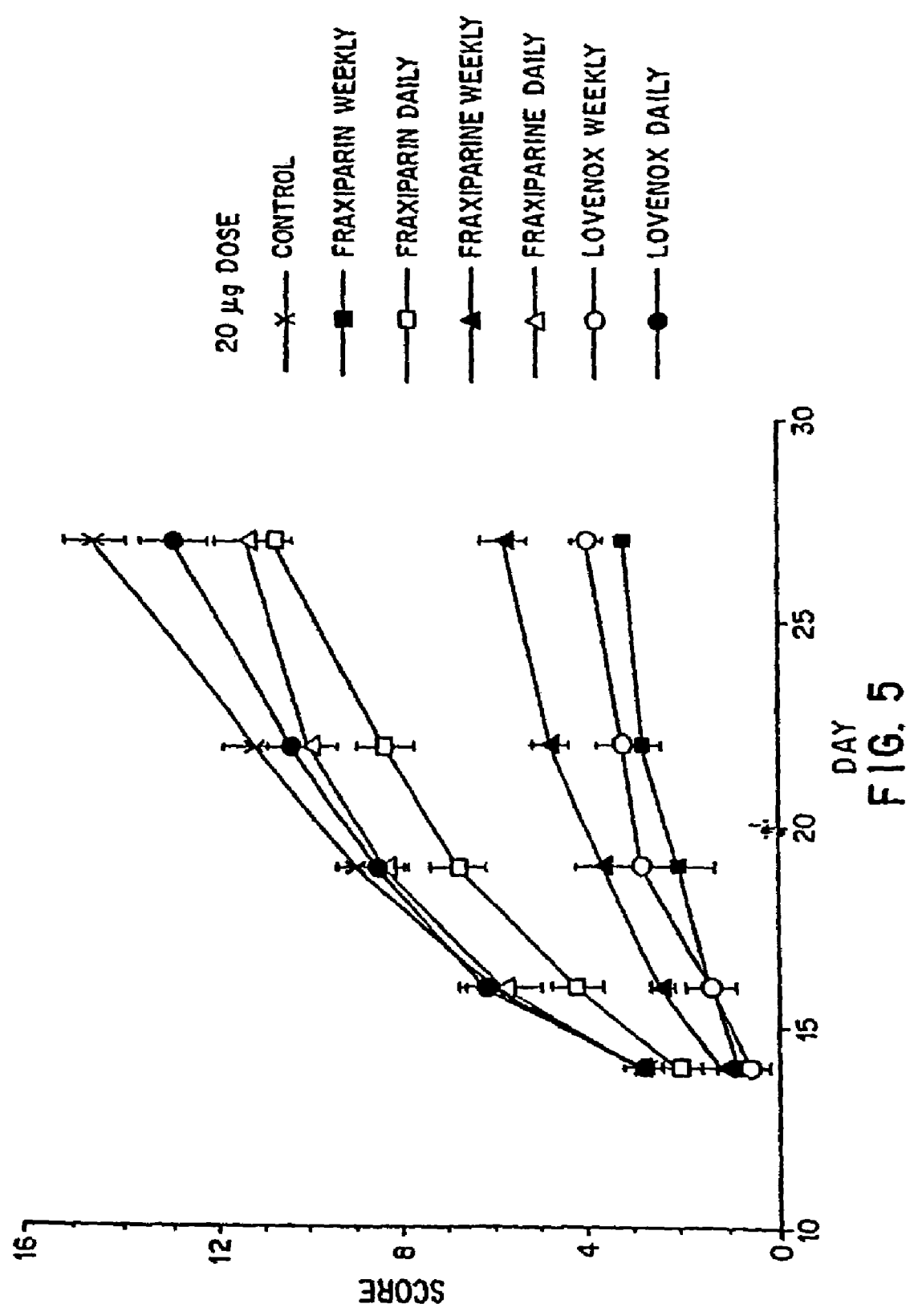

A similar inhibitory effect was observed with several other LMWHs administered to Lewis rats immunized to induce AA. FIG. 5 shows the results of the injection of a 20 µg dose of Fraxiparin® (daily (□); weekly (■)); Fraxiparine® (daily (△); weekly (▲)), Lovenox®/Clexane® (daily (●); weekly (○)), and PBS control (×). All the three LMWHs of different types and sources showed a marked inhibition of arthritis, when administered weekly, but not daily.

5.8. Treatment With LMWH Prevents Rejection of Allografts

Figure 6:
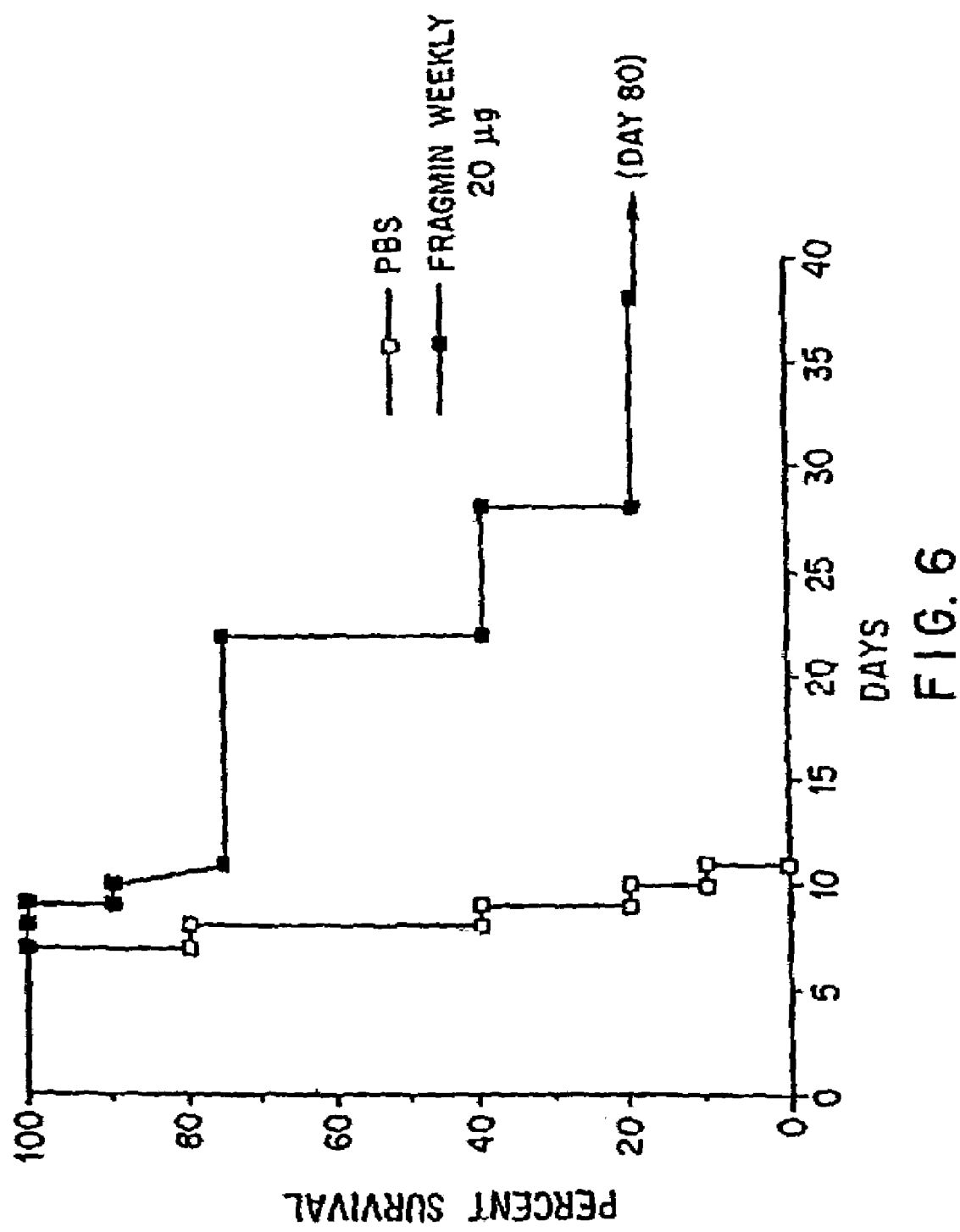
FIG. 6 plots the percentage of survival rate of rats that had undergone allogeneic heart transplants and had also received either weekly administration of Fragmin or PBS.

Wistar rats were subjected to allogeneic BN heart transplant (Ono, K. and Linsay, E. S., *J. Thorac. Cardiovasc. Surg.* (1969) 45:225-229). From the day before transplantation, the rats were injected subcutaneously at 7 day intervals with 20 µg of Fragmin® or PBS control (FIG. 6, ● and ○, respectively) and scored for survival. The day of rejection was determined as the day the transplanted heart stopped beating, assayed by palpation of the abdomen. FIG. 6 shows that the rats treated with the weekly dose of LMWH had a markedly increased survival of the heart allografts.

5.9. Biological Effect of LMWH on Insulin Dependent Diabetes Mellitus (IDDM) of NOD Mice Mice of the NOD strain spontaneously develop a form of type I insulin dependent diabetes mellitus (IDDM) that is the accepted model for human IDDM (Castano, L. and Eisenbarth, G. S., *Annu. Rev. Immunol.* (1990) 8:647-679). The disease begins at 4-5 weeks of age by the appearance of inflammation of the pancreatic islets, insulitis. The insulitis progressively damages the insulin-producing beta cells which are sensitive to damage by TNF-α. At about 4-5 months of age, a sufficient number of beta cells are destroyed so that diabetes becomes overt.

Figure 7:
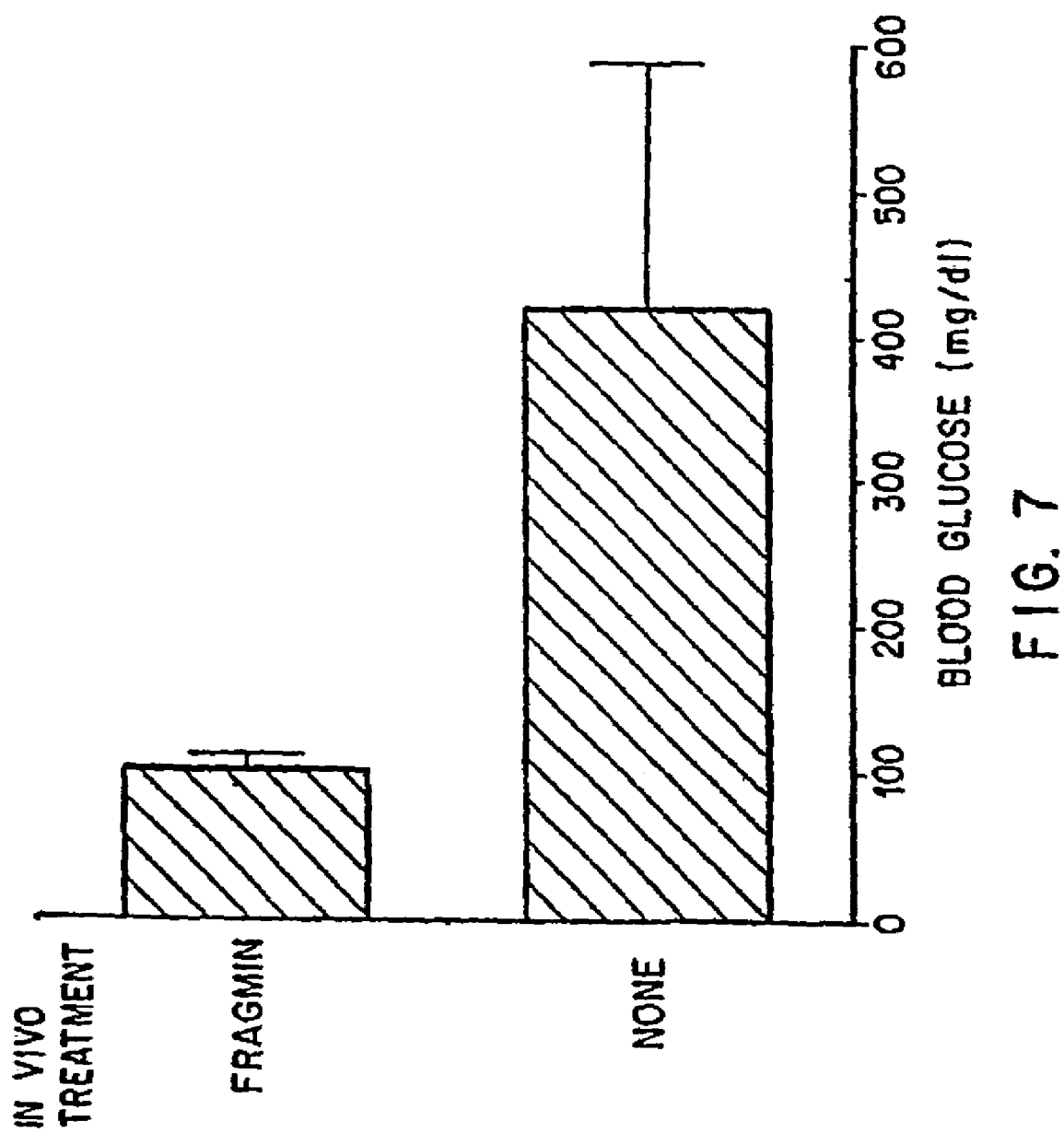
FIG. 7 presents bar graphs illustrating the blood glucose levels of two groups of NOD mice, one group receiving Fragmin and the other receiving only PBS.

To test whether treatment with LMWH could affect the IDDM process, a group of 10 female NOD mice was treated with weekly subcutaneous injections of 5 µg per mouse of Fragmin® (batch 38609), the dose determined to represent 12 mouse units per kg. A group of 10 control mice were treated with injections of saline. At the age of 5 months all the mice were bled to determine the development of IDDM using a standard procedure (Elias, D. et al., *Proc. Natl. Acad. Sci. U.S.A.* (1990) 87:1576-1580). FIG. 7 shows that the control mice ("none") had abnormal blood glucose (400 mg/dl). In contrast the mice treated with LMWH had a normal blood glucose (100 mg/dl). Thus treatment with LMWH can indeed cure the IDDM process.

5.10. LMWH Treatment of Allergy

In many allergic patients, intradermal challenge with specific antigen or anti-IgE induces an immediate wheal and flare reaction which is followed, 4-8 h later, by a period of persistent swelling and leukocyte infiltration termed the late phase cutaneous reaction. Late phase reactions (LPR)[2] were initially described in the skin (Solley, G. O. et al., *J. Clin. Invest.* (1976) 58:408-420). However, it is now clear that late consequences of IgE-dependent reactions, notably including infiltration of the reaction sites with blood-borne leukocytes, also occur in the respiratory tract and other anatomical locations (Lemanski, R. F. and Kaliner, M., in *Allergy: Principles and Practice*, Vol. 1 (1988), Middeton, Jr., E. et al. (Eds.), pp. 224-246). Indeed, it has been argued cogently that many of the clinically significant consequences of IgE-dependent reactions, in both the skin and the respiratory system, reflect the actions of the leukocytes recruited to these sites during the LPR rather than the direct effects of the mediators released at early intervals after antigen provocation (Kay, A. B. *J. Allergy Clin. Immunol.* (1991) 87:893-910).

It has recently been widely recognized that chronic allergic diseases such as asthma and atopic dermatitis are a result of an underlying inflammatory process which includes the infiltration and activation mainly of eosinophils and T cells (Kay, A. B. *J. Allergy Clin. Immunol.* (1991) 87:893-910).

Several lines of evidence support the hypothesis that the leukocyte infiltration associated with LPRs occurs as a result of mast cell degranulation. In both man and experimental animals, agents that induce cutaneous mast cell degranulation by either IgE-dependent of certain other mechanisms can also promote infiltration of the reaction sites with leukocytes (Solley, G. O. et al., *J. Clin. Invest.* (1976) 58:408-420; Lemanski, R. F. and Kaliner, M., in *Allergy: Principles and Practice*, Vol. 1 (1988), Middeton, Jr., E. et al. (Eds.), pp. 224-246; Kay, A. B. *J. Allergy Clin. Immunol.* (1991) 87:893-910). A review of the mediators that can be elaborated by activated mast cells reveals many that might contribute to leukocyte infiltration in LPRs, including lipid mediators such as $LTB_4$, $LTC_4$, $LTD_4$, $PGD_2$, and PAF (platelet activating factor), as well as several peptide or proteinaceous chemotactic factors (Holgate, S. T. et al., in *Allergy: Principles and Practice*, Vol. 1 (1988), Middleton, Jr. E. et al. (Eds.), pp. 135-178). The latter agents range in size from tetrapeptide "eosinophil chemotactic factors of anaphylaxis" to very high molecular weight "neutrophil chemotactic factors".

Even more candidate mast cell associated mediators of leukocyte infiltration recently have been identified, including cytokines similar or identical to INF-α, IL-1α, and four members of the MIP-1 gene family of small secreted peptides (Gordon, J. R. et al, *Immunol. Today* (1990) 11:458-464). Four of these cytokines (TNF-α, IL-1α, MIP-1α and MIP-1β) have been demonstrated to have the ability to promote leukocyte infiltration.

More recently, (Wershil, B. K. et al., in *J. Clin. Invest.* (1991) 87:446-453, by using mast cell deficient mice have demonstrated that the recruitment of leukocytes during IgE dependent LPR is mast cell dependent and that this inhibition was partially blocked by local administration of anti TNF-α antiserum. It is widely accepted today that the inhibition of the cellular infiltration/activation associated with IgE dependent LPR is a crucial therapeutic approach in alleviating various allergic diseases (Barnes, P. J. *N. Eng. J. Med.* (1989) 321:1517-1527).

To the surprise of the present applicants, it was found that LMWH significantly inhibited the leukocyte infiltration during IgE dependent cutaneous LPR in mice undergoing passive cutaneous anaphylaxis (PCA).

Mice received an i.d., injection (into the ears) of monoclonal IgE anti DNP Ab (~20 ng). A day later, the mice were i.v. injected with $DNP_{30-40}$-HSA in saline. Ear swelling was determined by measurement of ear thickness with a micrometer before and at various intervals after the challenge with the DNP-HSA. In all experiments, tissues from sites of PCA reactions were obtained after sacrifice by cervical dislocation and were processed for Giemsa-stained sections. LMWH was given once by s.c. injections (5 μg/mouse) on Day-2.

Results

Swelling developed rapidly at sites of PCA reactions (Δ of $35 \times 10^{-4}$ inch at 15 min.) but not at control sites (ears injected with diluent alone). Swelling of PCA sites diminished markedly between 2 and 4 hours after i.v. antigen challenge.

PCA and control sites were assessed histologically at 6-8 hours after the i.v. antigen challenge. The majority of mast cells at PCA sites exhibited extensive or moderate degranulation. By contrast <5% of mast cells at control sites exhibited marked degranulation. There was a significant neutrophil infiltration only in PCA sites at 6 hour post antigen challenge. This infiltration was markedly reduced (by 60%) in mice which had been pretreated with LMWH two days earlier. There was no effect of this drug on the magnitude of mast cell degranulation. There was no effect of the drug on the total and differential count of leukocytes in the peripheral blood of these animals. It can be concluded that LMW heparin inhibited the cellular infiltration associated with the IgE dependent late cutaneous reaction. Additionally, the applicants also anticipate that the administration of LMWH will exhibit a beneficial effect on cutaneous LPR in animals with active cutaneous anaphylaxis (specific IqE production will be induced with DNP-HSA Alum). Similar therapeutic effects on pulmonary allergic inflammation are also anticipated (Tarayre, J. P. et al. *Int. J. Immunonharmacol.* (1992) 14(5):847-855.

5.11. LMWH Treatment of Human DTH

Figure 8:
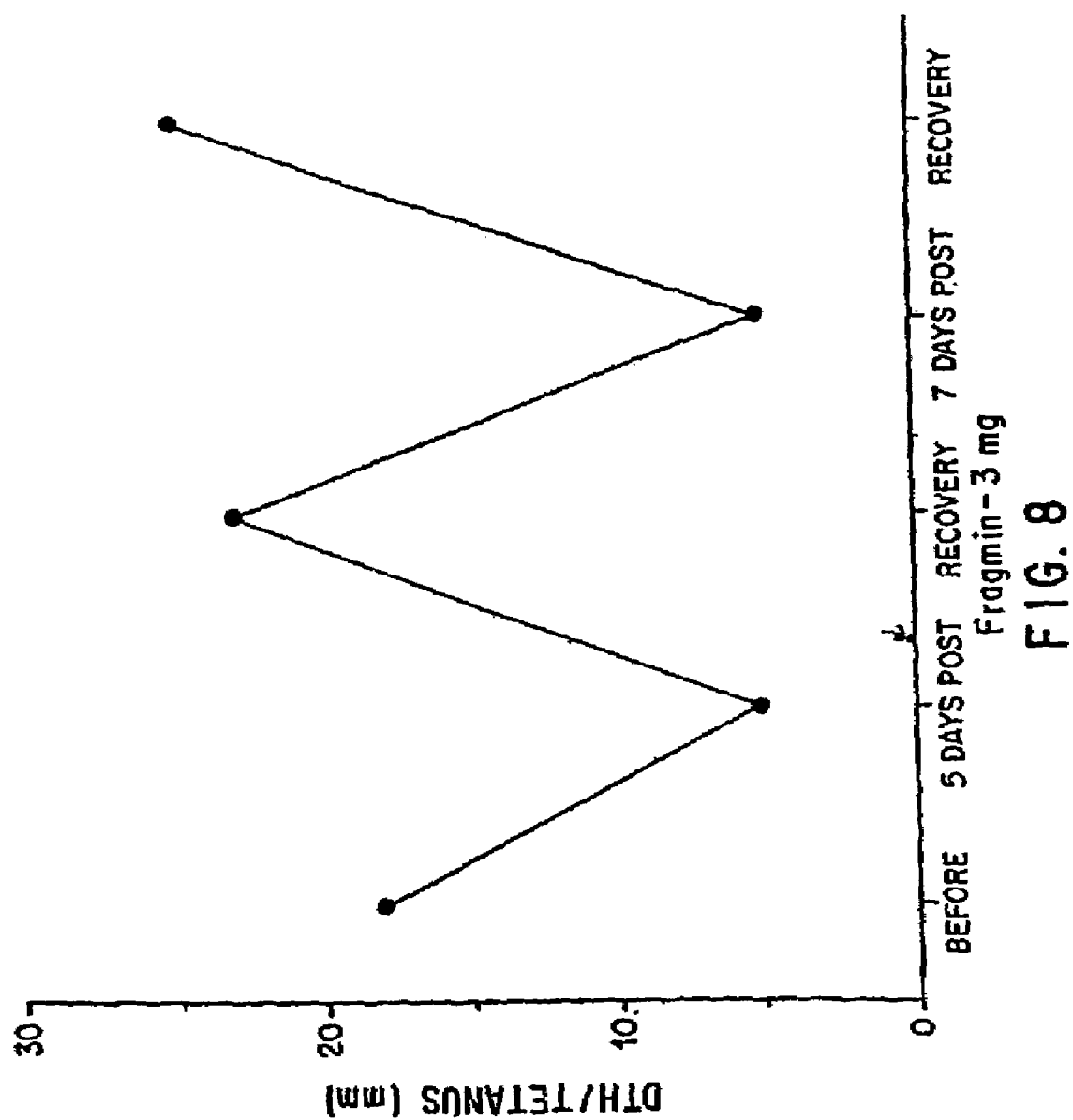
FIG. 8 illustrates the results of a DTH experiment involving a human volunteer.

FIG. 8 shows an experiment in which a 40 year old male volunteer weighing 85 kg was tested for DTH reactivity to tetanus antigen (Merieux skin test applicator). About 18 mm of induration was measured at 24 and 48 hours. The volunteer was then treated with a subcutaneous injection of Fragmin® (batch 38609) 3 mg. Five days later the volunteer was again tested for his DTH response to tetanus and the induration was inhibited to about 5 mm. The volunteer was tested again for DTH 3 weeks later ("Recovery") and the test showed positive reactivity (23 mm of induration at 24 and 48 hours). The volunteer was then treated with Fragmin® as before and the DTH reactivity was measured again 7 days later ("7 days post"). Again the DTH was inhibited to about 5 mm of induration. Recovery of DTH again was found 3 weeks later. Thus, LMWH at a dose of less than 5 mg can inhibit DTH in humans at treatment intervals of 5 and 7 days.

6. Experiments Using LMWH (Fragmin) and Other Active Substances 6.1. Stability Studies of LMWH (Fragmin) TNF-α Inhibitory Activity Fragmin batch 38609 was diluted in normal saline to a concentration of 5 μg/0.1 ml. Some of the vials were mixed with an equal amount of protamine sulfate (5 μg) and the vials were stored at room temperature (21° C.) for 0 to 72 hours (Table XI) or were stored at 4° C. for 1 to 4 months (Table XII). The Fragmin with or without protamine sulfate was then used in vivo to inhibit the DTH T cell reaction in BALB/c mice as described above. For the present experiments, the positive control DTH was $17.5 \pm 1.2 \times 10^{-2}$ mm (0% inhibition) and the fully inhibited DTH was $2.6 \pm 0.5 \times 10^{-2}$ mm. (100% inhibition).

The results of the incubation of LMWH at 20° C. are listed in the Table XI. It is evident from Table XI that LMWH loses its inhibitory activity against TNF-α-dependent, T cell mediated DTH reaction upon incubation at ambient temperature over 72 h. In contrast, Heparin and LMWH lose their anti-coagulant activity at ambient temperature only slowly.

TABLE XI

Stability of Inhibitory Activity of Fragmin (Batch 38609, 5 μg/0.1 ml), Without Protamine Sulfate, at 20° C. Against DTH-Reaction.

| No. Hours | DTH Reaction | % anti-DTH Reactivity |
|---|---|---|
| None | 17.5 ± 1.2 | Control* |
| 0 | 2.6 ± 0.5 | 100** |
| 24 | 9.6 ± 1 | 47 |
| 48 | 15.7 ± 1.6 | 13 |
| 72 | 17 ± 0.8 | 0 |

*no inhibition
**full inhibition

6.2. Loss of Anti-DTH Reactivity at Low Temperature and Stabilizing Effect of Added Protamine Table XII shows that Fragmin loses its ability to inhibit the DTH reactivity of mouse T cells in dilute solution within 4 months at 4° C. The addition of an equal concentration of protamine sulfate does not interfere with inhibition of the DTH reaction, but actually preserves this activity intact after 4 months at 4° C. Again, this result is contrary to the normal role of protamine sulfate, when added to heparin or Fragmin, in which the protamine sulfate neutralizes the anti-coagulant effects of the heparinoid substances.

TABLE XII

Loss of Anti-DTH Activity Over Time at Low Temperature. Stabilizing Effect of Added Protamine.

| Fragmin (38609) | Months at 4° C. | Protamine Sulfate | DTH ($10^{-2}$ mm) | % Anti-DTH Activity |
|---|---|---|---|---|
| none | none | none | 15 ± 1 | control* |
| yes | 1 | none | 2.8 ± 0.5 | 100** |
| yes | 1 | yes | 3 ± 0.4 | 100 |
| yes | 2 | none | 4 ± 0.8 | 82 |
| yes | 2 | yes | 2.4 ± 1 | 100 |
| yes | 3 | none | 9.6 ± 0.8 | 55 |
| yes | 3 | yes | 3 ± 0.5 | 100 |
| yes | 4 | none | 14.8 ± 1.4 | 0 |
| yes | 4 | yes | 3 ± 0.4 | 100 |
| yes | 0 | yes | 3 ± 0.5 | 100 |

*no inhibition
**full inhibition

6.3. Preparation of ECM-Coated Plates

ECM-coated wells were prepared as follows. Freshly dissected bovine eyes were obtained from a slaughter house within a few hours after slaughter. The eyes were dissected in a hood to remove the cornea. The cornea were then scratched or scraped with a scalpel to obtain the corneal endothelial cells. These cells were cultured on tissue culture plates with approximately 5 ml of media comprising DMEM supplemented with 10% fetal calf serum, 5% calf serum and antibiotics, such as 1% streptomycin or 1% neostatin, together with 1% glutamine as a stabilizer. The cells settled to the bottom of the plates after approximately 2 days of seeding, were fed with fresh media every four days, and incubated at 37° C. in 5% $CO_2$ humidified incubators. If desired, some fibroblast growth factor may also be added to the media, although the addition of FGF is not crucial. When the cells were confluent (approximately 2 weeks later), the supernatant was aspirated off, and the cells were then trypsinized with 1-2 mls of trypsin.

Eighty percent of these primary cells (the fate of the remaining 20% of the primary cells is described immediately below) were taken and divided onto 5 flat-bottomed 96-well plates. The cells were cultured in DMEM supplemented with 4% dextran T-40, 10% fetal calf serum and 5% calf serum. After about 7 days of incubation at 37° C. in a 10% $CO_2$ humidified incubator, the resulting confluent layers of endothelial cells were lysed. The lysing buffer, comprising 0.025 M $NH_4OH$ containing 0.25% Triton X in PBS, was allowed to remain over the cells for 10 minutes and then decanted. The contents of the plates were then washed three times with PBS chilled to 4° C. The preceding procedure left the ECM intact, firmly attached to the entire area of the well. The resulting ECH was also free of nuclei and cellular debris. The ECM-coated plates can be stored at 4° C. for at least three months.

The remaining 20% of the primary cells were left on a single plate and cultured in approximately 5 ml of media comprising DMEM supplemented with 10% fetal calf serum, 5% calf serum and antibiotics as described above. This secondary crop of cells was allowed to become confluent and was treated with trypsin as described above. Again, the trypsinized cells were divided, 80% being cultured in 5 plates in the growth media containing 4% Dextran T-40, and 20% being cultured in a single plate as before. It is possible to perform this 80/20 division yet one more time from this single plate.

6.4. Degradation of Sulfated Proteoglycans $^{35}(S)O_4$-labelled ECM was incubated with 5 μl of MM5 heparanase (4 u/ml) in 1 ml PBS and 100 μl 8.2 M phosphate-citrate buffer (pH 6.2) for 48 hrs. at 37° C. The medium was then collected, centrifuged at 10,000 g for 5 min. (optional) and analyzed by gel filtration on Sepharose 4B columns. Two ml fractions were eluted with PBS at a flow rate of 5 ml/hr and were counted for radioactivity using Bio-Fluor Scintillation fluid.

This $^{35}(S)O_4$-labelling experiment showed that the ECM was actually being degraded, that the resulting degradation products were successfully being released, and, furthermore, were being properly filtered through the Sepharose 4B columns. Subsequent experiments related to the degradation of sulfated proteoglycans were carried out on non-labeled ECM, with the degradation products being monitored by their absorption at 206 or 232 nm, instead.

Enzyme degradation experiments were carried out as above and, in addition, the degradation products (DECM) were purified further by loading the degraded proteoglycans that were eluted from the Sepharose columns onto HPLC columns. HPLC analysis of the Sepharose column fractions was carried out in a manner such as that described in Section 6.11 et seq. Detection of the degradation products was achieved by monitoring their absorption at 206 nm.

Additional enzyme degradation experiments were carried out with similar results using PC3 enzyme and heparanase obtained from IBEX.

6.5. Purification of Human $CD4^+$ T Cells $CD4^+$ T cells were obtained from peripheral blood mononuclear leukocytes obtained from healthy human donors as follows. The mononuclear cells were isolated on a Ficoll gradient; washed in RPMI supplemented with 10% FCS and antibiotics in petri dishes and incubated at 37° C. in a 10% $CO_2$ humidified atmosphere. After 1 h, the non adherent cells were removed and incubated on nylon-wool columns (Fenwall, Ill.) for 45-60 min at 37° C. in a 10% $CO_2$ humidified atmosphere. Non adherent cells were eluted and washed. $CD4^+$ T cells were negatively selected by exposure of the eluted cells to a mixture of the following monoclonal antibodies (mAb): anti-CD8, CD19, and CD14 conjugated to magnetic-beads (Advanced Magnetics, Cambridge, Mass.). Unbound cells were recovered and their phenotypes were examined. The resultant purified cells were predominantly (>90%) $CD3^+CD4^+$ as determined by FACScan analysis.

6.6. Bioassay of TNF-α Activity Using Human $CD4^+$ T Cells Derived from PBLs.

Two hundred fifty-thousand human $CD4^+$ T cells were preincubated with 150 μl of ECH degradation products at various concentrations for 1.5 h at 37° C., under a 7% $CO_2$ atmosphere. Then 100 μl of PHA (Wellcome Co., England, 1 μg/ml) were added for 3 h incubation, in flat-bottomed 96-well plates (Costar). Subsequently, the contents of the wells (3-6 wells per experimental group) were collected, centrifuged, and the media were assayed for TNF-α secretion as previously described in Section 5.1. Briefly, supernatants of cultured lymphocytes were added to cultures of mouse fibrosarcoma cell clones (BALB/c.CL7). BALB/c.CL7 cells are sensitive to killing by TNF-α in the presence of actinomycin D (0.75 µg/ml). Nophar, Y. et al. *J. Immunol.* (1988) 140 (10):3456-3460. The death of these cells, in the presence of the test media, was calibrated in comparison to titration curves of added exogenous TNF. Cell viability is determined by incubation with MTT tetrazolium (Sigma, Cat. No. M2128) for two hours, extracting the dye that was taken up by the cells with isopropanol-HCl mixture and quantitating it calorimetrically (at 570 nm) with a Microelisa Autoreader. TNF-α typing was done by examining the neutralizing effect of anti-murine TNF-α mAb (diluted 1/400; Genzyme, Mass.).

6.7. Degradation of Heparin

One milligram of heparin (Sigma) in 1 ml of PBS and 100 µl 25 M phosphate-citrate buffer (pH 6.2) was incubated with 20 µl MM5 (5 u/ml) for 48 hrs. at 37° C. The products of the reaction were then analyzed by gel filtration on Sepharose 4B columns. Two ml fractions were eluted with PBS at a flow rate of 5 ml/hr. To further characterize the degradation products, the peaks eluted from the Sepharose column were subjected to HPLC separation using Toyo Soda-Gel G3000SW and G2000SW HPLC columns, as described in Section 6.11 et seq.

Figure 29A:
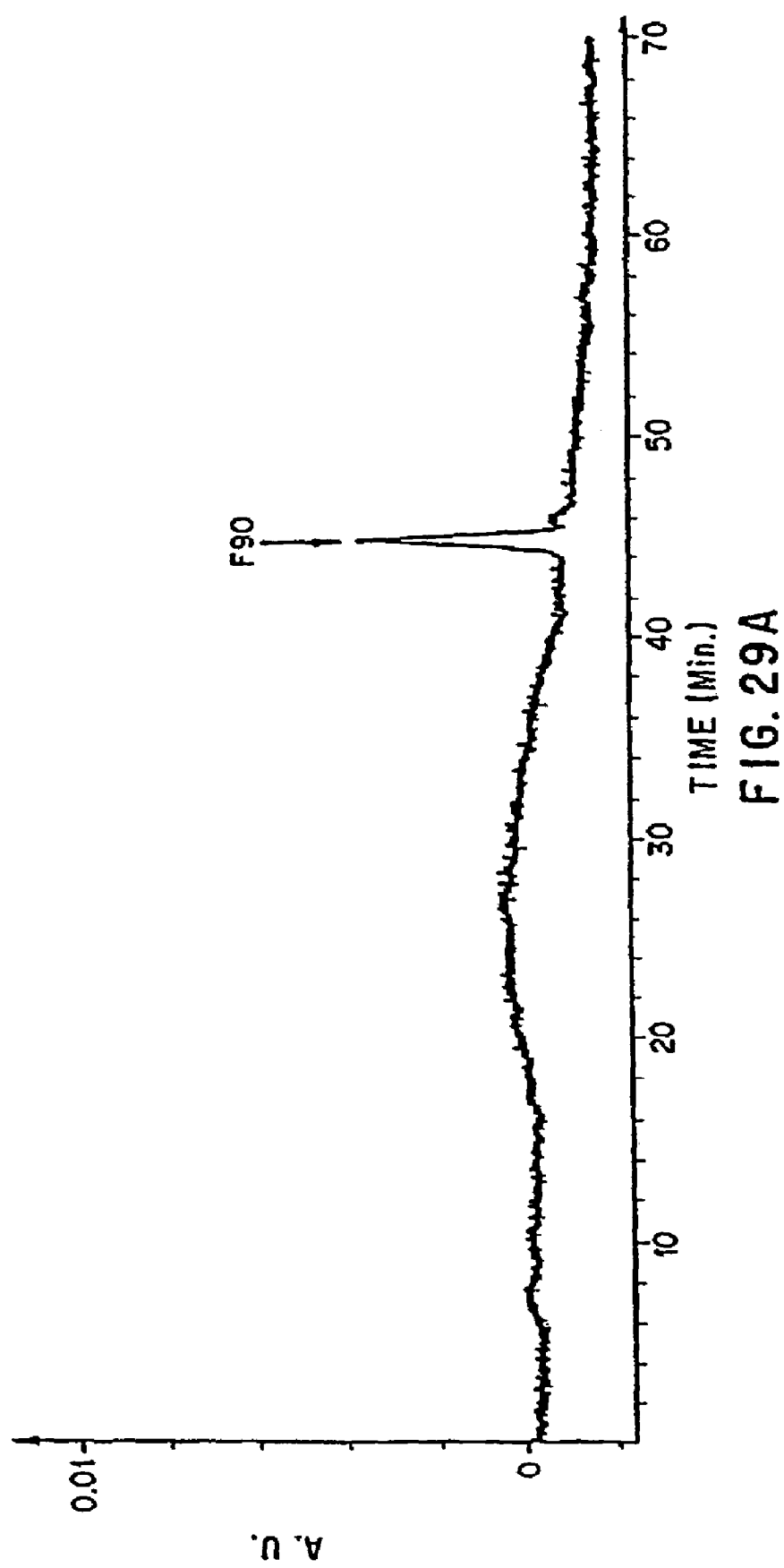
FIG. 29 illustrates fraction F90 obtained from the HPLC separation of Fragmin.
Figure 29B:
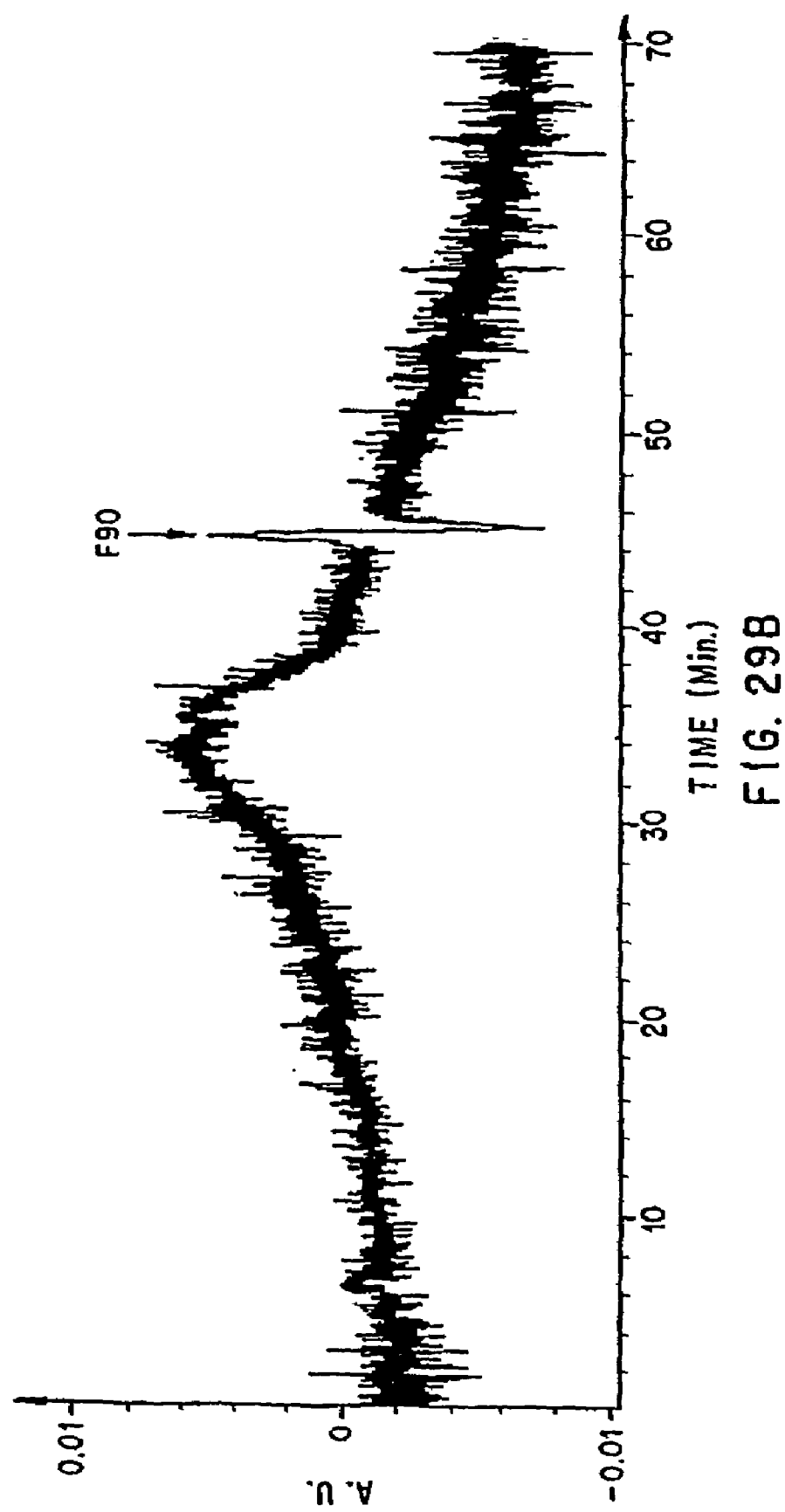

Additional experiments were carried out using 20 µl of PC3. The PC3 enzymatic reaction was carried out with 1 mg of heparin under the same conditions as described above for the MM5 except that the reaction was incubated for 24 hrs instead of 48 hrs. The products were then analyzed by gel filtration on Sepharose 4B columns (FIG. 29). The in vitro bioassay results are shown in Table XIX below.

6.8. Elicitation of DTH Response in Mice and Examining Inhibitory Effects

BALB/c mice (at least 5 mice per group) were sensitized on the shaved abdomen with 3% 4-ethoxymethylene-2-phenyl oxazolone (OX; BDH-Chemicals, GB) in acetone/olive oil applied topically. DTH sensitivity was elicited 5 days later as follows. Mice were challenged with 0.5% OX in acetone/olive oil. The ear was measured immediately before challenge and 24 h later with Mitutoyo engineer's micrometer (Japan). The individual measuring the swelling of the ear was blinded to the identity of the groups of mice. To interfere with DTH response, the low molecular weight immuno-regulatory fractions, diluted in PBS, were administrated subcutaneously into the back of the treated mice at the indicated time schedules and concentrations. Treated mice were inspected during and after (>2 months) the treatment and no major side-effects were observed clinically.

6.9. Separation of LMWH (Fragmin) on Size-Exclusion Gel Chromatography Column (Sepharose 4B)

Fragmin (Batch 38609) and inactive Fragmin were fractionated by gel filtration on Sepharose 4B (Pharmacia) columns. Fractions of 0.5 ml were eluted with PBS at a flow rate of 5 ml/hr, and monitored for absorbance at 206 nm. (No absorbance was detected at 280 nm). A plot of the fraction number versus absorption at 206 nm appears on FIG. 11. The results of the bioassays for selected fractions are presented in Tables XIII and XIV, below.

TABLE XIII

Effect, of Whole Fragmin, Sepharose 4B Fractions of Fragmin, and an HPLC Fraction of a Sepharose 4B Fraction on the Secretion of Active TNF Using Human PBL Bioassay.

| Test Material | conc (pg/ml) | Bioassay of TNF Activity (%) | "R" value % × (pg/ml)$^{-1}$ |
|---|---|---|---|
| Active Frag/whole | 1 | Inh$_{max}$ (90%) | 90 |
| Inactivated Frag/whole | a | No effect | 0 |
| Inactivated Frag/Seph. 4B-F15 | 5 | Inh$_{max}$ (50%) | 50 |
| Inactivated Frag/Seph. 4B-F10 | a | No effect | 0 |
| Inactivated Frag/Seph. 4B-F8 | 1000 | Aug$_{max}$ (60%) | 0.06 |
| Inactivated Frag/Seph. 4B-F2 | 1000 | Aug$_{max}$ (30%) | 0.03 |
| Frag/HPLC-F90 | b | No effect | 0 | a At a conc range of 1 µg/ml-0.001 pg/ml.
b At a conc range of 1 µg/ml-0.01 pg/ml.

TABLE XIV

Effect of Whole Fragmin and Sepharose 4B Fractions of Fragmin on DTH Sensitivity of Mice.

| Test Material | Dose (µg/gm mouse) | Inhibition of DTH (>50%) | "R" value % × (µg/gm)$^{-1}$ |
|---|---|---|---|
| Active Frag/whole | 0.2 | 50 | 250 |
| Inactivated Frag/whole | 0.2-0.004 | No effect | 0 |
| Inactivated Frag/Seph. 4B-F15 | 0.004 | 50 | 12,500 |
| Inactivated Frag/Seph. 4B-F10 | 0.2-0.004 | No effect | 0 |

6.10. Additional Experiments Involving the Fractionation of Fragmin and Heparanase-Degraded ECM Fragmin and heparanase-degraded ECM were fractionated by gel filtration on Sepharose 4B columns. Fractions of 0.2 ml were eluted with PBS at a flow rate of 5 ml/hr, and monitored for absorbance at 206 nm. (No absorbance was detected at 280 nm). A plot of the fraction number versus absorption at 206 n.m. appears on FIG. 14. The results of the bioassays for selected fractions are presented in Table XV below.

TABLE XV

Effect of Sepharose 4B Fractions of Fragmin and DECM on the Secretion of Active TNF Using Human PBL Bioassay.

| Test Fraction | conc (pg/ml) | Bioassay of TNF Activity (%) | "R" value % × (pg/ml)$^{-1}$ |
|---|---|---|---|
| Frag/Seph. 4B-F39 | 100 | Inh$_{max}$ (60%) | 0.6 |
| DEHC/Seph. 4B-F39 | 10,000 | Inh$_{max}$ (85%) | 0.0085 |
| Frag/Seph. 4B-F42 | a | No effect | 0 |
| DECM/Seph. 4B-F42 | a | No effect | 0 |
| Frag/Seph. 4B-F32 | 10 | Aug$_{max}$ (55%) | 5.5 |
| DECM/Seph. 4B-F46 | 10 | Aug$_{max}$ (20%) | 2 | a At a conc range of 1 µg/ml-0.001 pg/ml.

6.11. Separation of Active Substances From Fragmin Using High Performance Liquid Chromatography Two experiments were performed utilizing two sets of high performance liquid chromatography conditions. The initial type of column used was a 30 cm×7.8 mm I.D. TSK-Gel® G-Oligo-PW column with a 4 cm×6 mm I.D. guard column. The column was eluted with 0.2 M phosphate buffer, pH 7.0, at a flow of 0.5 ml/min. The fractions collected were each 0.5 mls in volume.

The second type of HPLC used was Toyo Soda TSK-Gel G3000SW (7.5 mm×50 cm) and G2000SW (7.5 mm×50 cm) columns (in series) with a 7.5 mm×10 cm guard column from Phenomenex. The column was eluted at 1 ml/min. with carefully degassed 0.5 M NaCl. Fractions were collected at 0.5 ml per fraction. The detector was set at 232 nm with 0.02 AUFS and retention times measured to ±0.1 sec. The void and total volumes were measured by blue dextran and sodium azide. The collections were also subjected to detection at 206 nm under the same conditions as the 232 nm setting.

A plot of the Fragmin HPLC fraction number versus absorption at 206 nm appears on FIG. 18A. The results of the bioassays for selected fractions are presented in Table XVI, below. It is evident from the results presented that certain substances are able to inhibit the activity of TNF-α while others are able to augment its activity.

TABLE XVI

Effect of Whole and HPLC Fractions of Fragmin on the Secretion of Active TNF Using Human PBL Bioassay.

| Fragmin Fraction | conc (pg/ml) | Bioassay of TNF Activity (%) | "R" value % × (pg/ml)$^{-1}$ |
| --- | --- | --- | --- |
| Whole[a] | 10 | Inh$_{max}$ (40%) | 4 |
| HPLC-F1 | 100 | Aug$_{max}$ (60%) | 0.6 |
| HPLC-F3 | 10 | Inh$_{max}$ (70%) | 7 |
| HPLC-F16 | 10 | Inh$_{max}$ (100%) | 10 |
| HPLC-F22 | 10 | Inh$_{max}$ (100%) | 10 |
| HPLC-F26 | 100 | Inh$_{max}$ (50%) | 0.5 |
| HPLC-F30 | 100 | Inh$_{max}$ (70%) | 0.7 |
| HPLC-F47 | 100 | Inh$_{max}$ (55%) | 0.55 |

[a]This whole Fragmin sample had been aged at 4° C. for 90 days.

6.12. Separation of Active Substances From ECM Using High Performance Liquid Chromatography Separation of active substances from ECM by high performance liquid chromatography was carried out as discussed in Section 6.11.

A plot of the ECM HPLC fraction number versus absorption at 206 nm appears on FIG. 18B. The results of the bioassays for selected fractions are presented in Table XVII, below. It is evident from the results presented that certain substances isolated from heparanase-mediated degradation of ECM are able to inhibit the activity of TNF-α while others are able to augment its activity. The results also show that certain fractions obtained from the HPLC separation exhibit no effect on the activity of TNF.

TABLE XVII

Effect of DECM HPLC Fractions on the Secretion of Active TNF Using Human PBL Bioassay.

| DECM Fraction | conc (pg/ml) | Bioassay of TNF Activity (%) | "R" value % × (pg/ml)$^{-1}$ |
| --- | --- | --- | --- |
| HPLC-F1 | a | No Effect | 0 |
| HPLC-F5 | a | No Effect | 0 |
| HPLC-F10 | 10 | Inh$_{max}$ (60%) | 6 |
| HPLC-F14 | 10 | Inh$_{max}$ (70%) | 7 |
| HPLC-F17 | a | No Effect | 0 |
| HPLC-F25 | 1000 | Aug$_{max}$ (40%) | 0.04 |
| HPLC-F33 | 100 | Aug$_{max}$ (40%) | 0.4 |
| HPLc-F37 | 10 | Aug$_{max}$ (100%) | 10 |
| HPLC-F39 | 100,000 | Inh$_{max}$ (60%) | 0.0006 |
| HPLC-F42 | a | No Effect | 0 |
| HPLC-F46 | 1000 | Aug$_{max}$ (30%) | 0.03 |
| HPLc-F49 | 1000 | Aug$_{max}$ (30%) | 0.03 |
| HPLC-F61 | a | No Effect | 0 | a At a conc range of 1 μg/ml-0.001 pg/ml.

6.13. Carbazole Quantitative Sugar Assay

Briefly, 1500 μl of borate sulphuric acid reagent is cooled on an ice bath. The test solution (250 μl containing 20 μg of uronic acid/ml) is then carefully layered onto the surface of the boric acid reagent and allowed to diffuse for 10 minutes. The solutions are then thoroughly mixed, put in a boiling bath for 10 minutes, and then cooled in an ice bath. Chilled carbazole (50 μl) is then added to the mixture, vortexed, and put in a boiling bath for 15 minutes. The solution is then cooled and the absorbance is read at 525 nm. The results are compared with calibrated solutions.

6.14. Isolation of a Disaccharide from ECM Degradation Products

A disaccharide substance was isolated by HPLC from bovine corneal endothelial ECM that had been subjected to mammalian heparanase (MM5).

Figure 19:
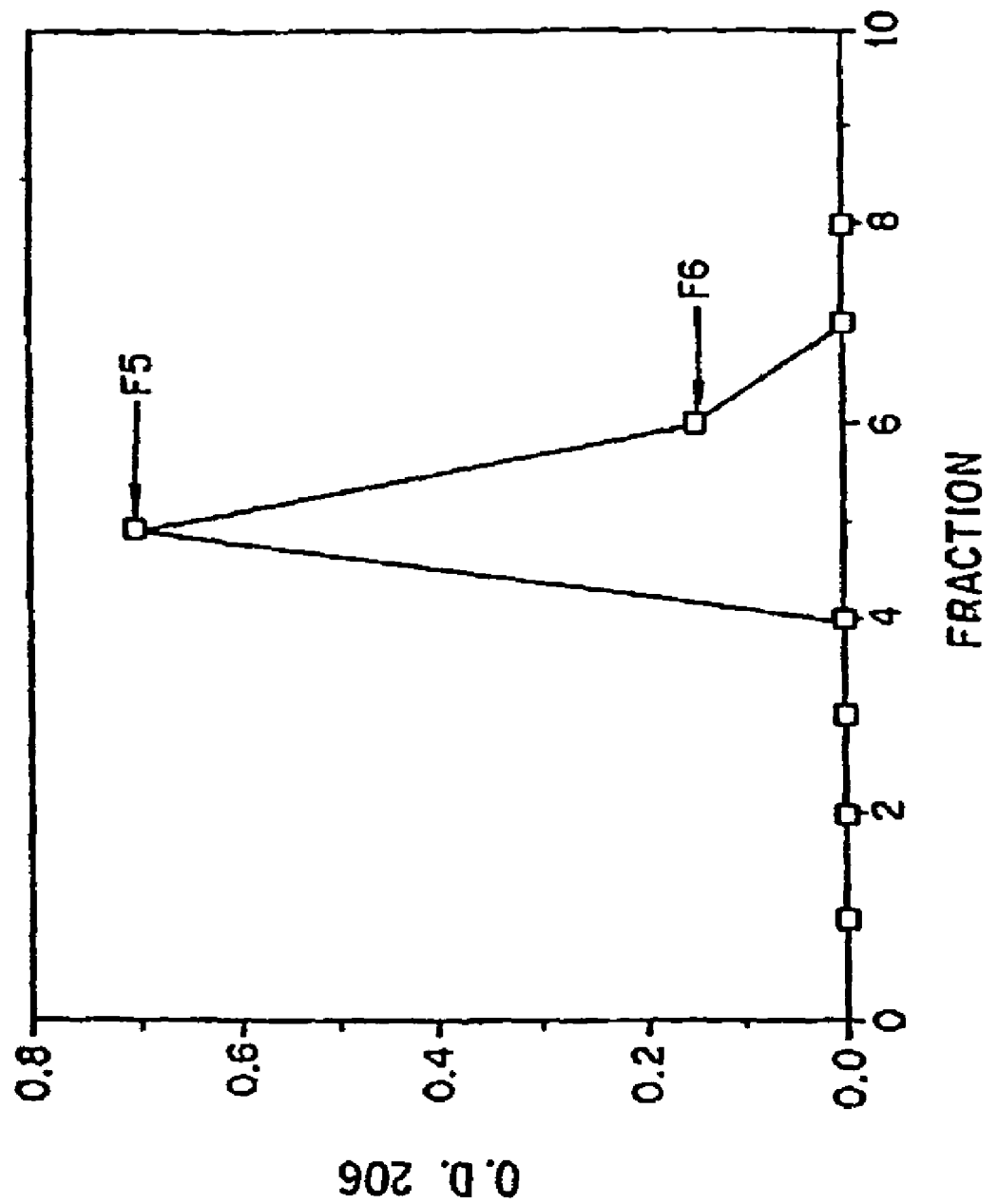
FIG. 19 illustrates the absorption at 206 nanometers of two fractions, F5 and F8, obtained from the Sepharose 4B column separation of heparanase-degraded ECM.
Figure 20B:
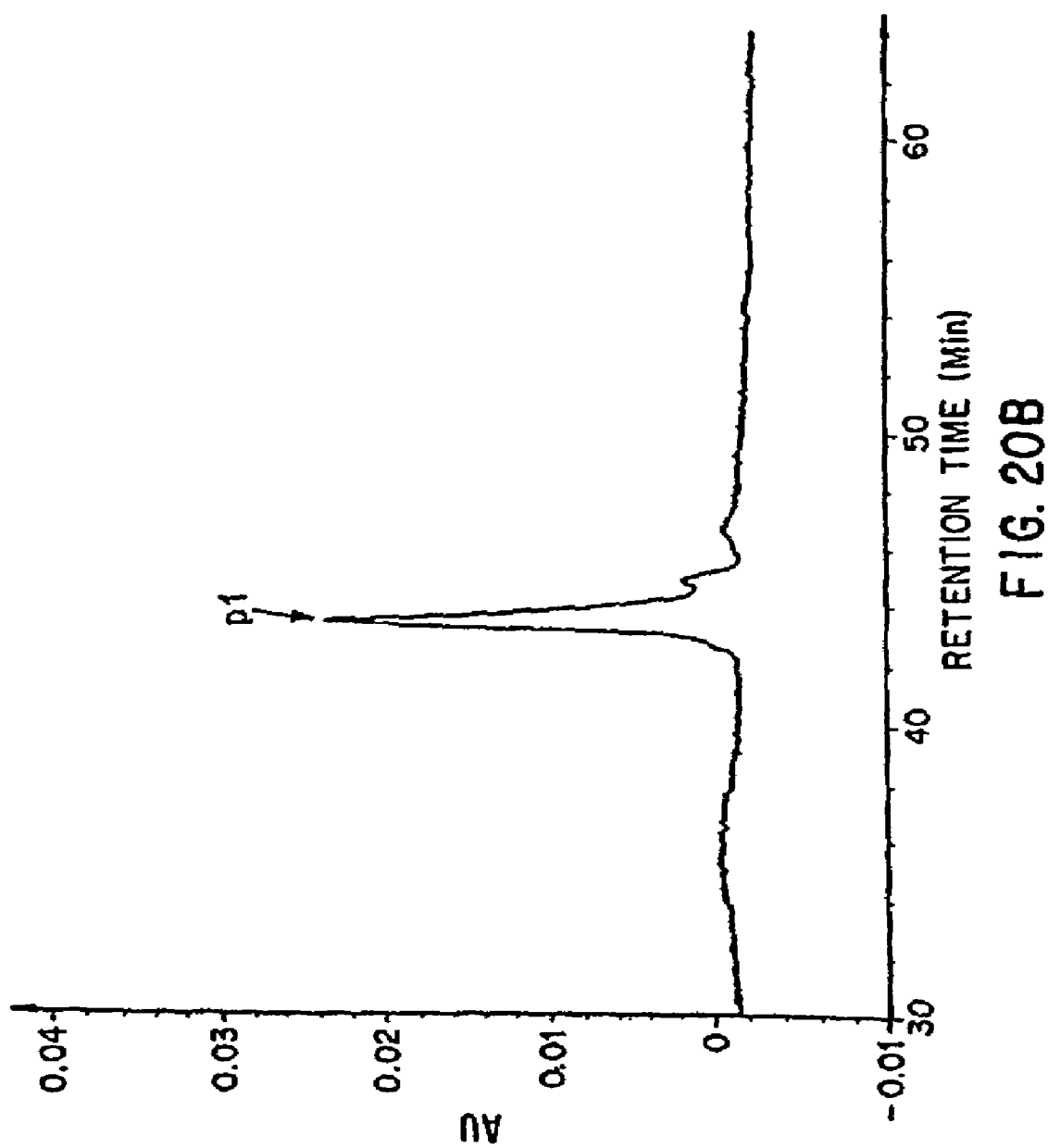

More Specifically:

An ECM-coated plate was incubated with 20 μl of mammalian heparanase (0.5 mg/ml) in 1 ml PBS buffer (that was preadjusted to pH 6.2 by citric acid), for 48 hours at 37° C. The medium was then collected and applied on a Sepharose-4B column (35 cm×0.7 cm I.D.). The mobile phase was PBS buffer at a flow rate of 5 ml/hr. Fractions of 2.2 ml were collected and monitored at 206 nm (FIG. 19). A sample (100 ul) from Sepharose 4B fraction no. 5 (8.8-11 ml elution volume) were injected into an HPLC column (Toyo Soda TSK-Gel G3000SW (7.5 mm×50 cm) and G2000SW (7.5 mm×50 cm), in series with 7.5 mm×10 cm guard from Phenomenex). The mobile phase was 0.5 M NaCl at a flow rate of 1 ml/min. One ml fractions were collected and monitored at 206 and 232 nm (FIGS. 20A and 20B). Peak no 1. (P1) was freeze dried in a 25 ml flask. The sample contains ca. 20 μg of oligosaccharide (determined by carbazole assay) in 60 mg NaCl.

The sample has an elution profile that is similar to a disaccharide standard or molecular weight "marker" obtained commercially from the depolymerization of heparin (Sigma).

Figure 21A:
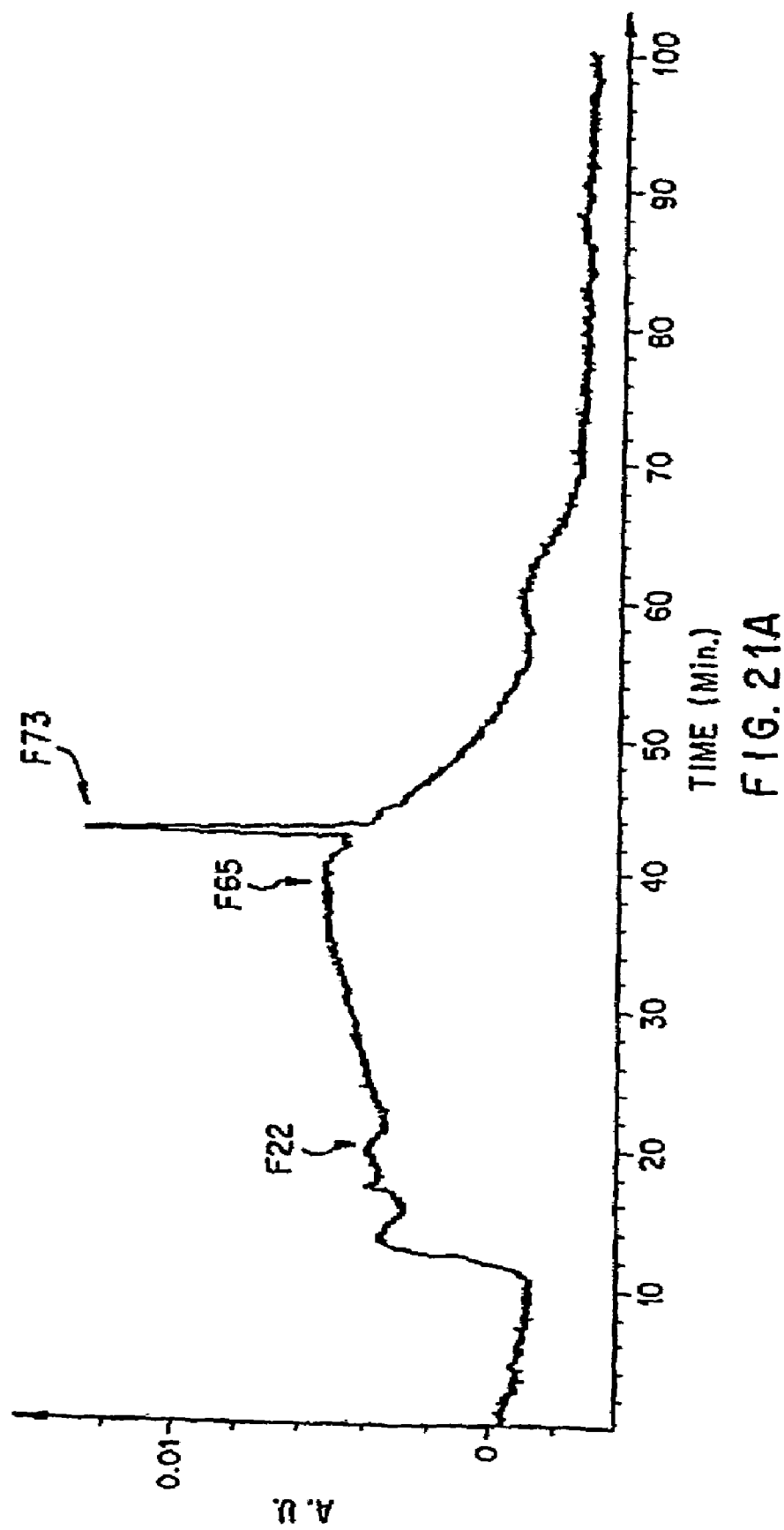
FIGS. 21A and 21B illustrate the uv absorption of additional HPLC fractions obtained from fraction F5.
Figure 21B:
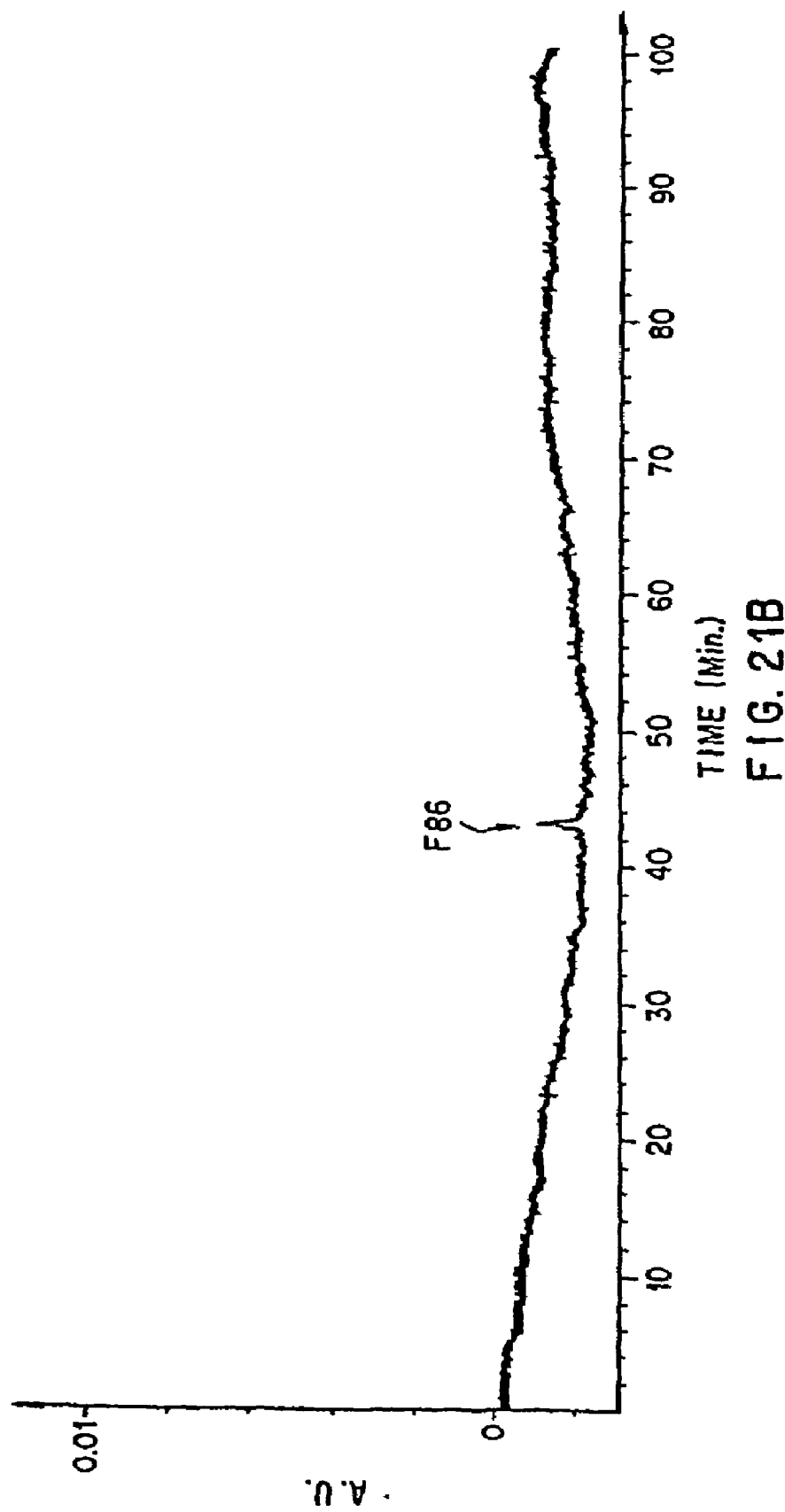

The Inh$_{max}$ value of the substance, based on similarly obtained samples (See, for example peak F73, in FIG. 21A (elution time of about 44 minutes) and entry F5/HPLC-F73 in Table XVIII, below), was estimated at 87% in an in vitro TNF-α inhibition assay using human PBLs, at a concentration of about 10 pg/ml. The bioassay was conducted as previously described, above. This sample may be purified further using a SAX-HPLC column, as described below.

Figure 22:
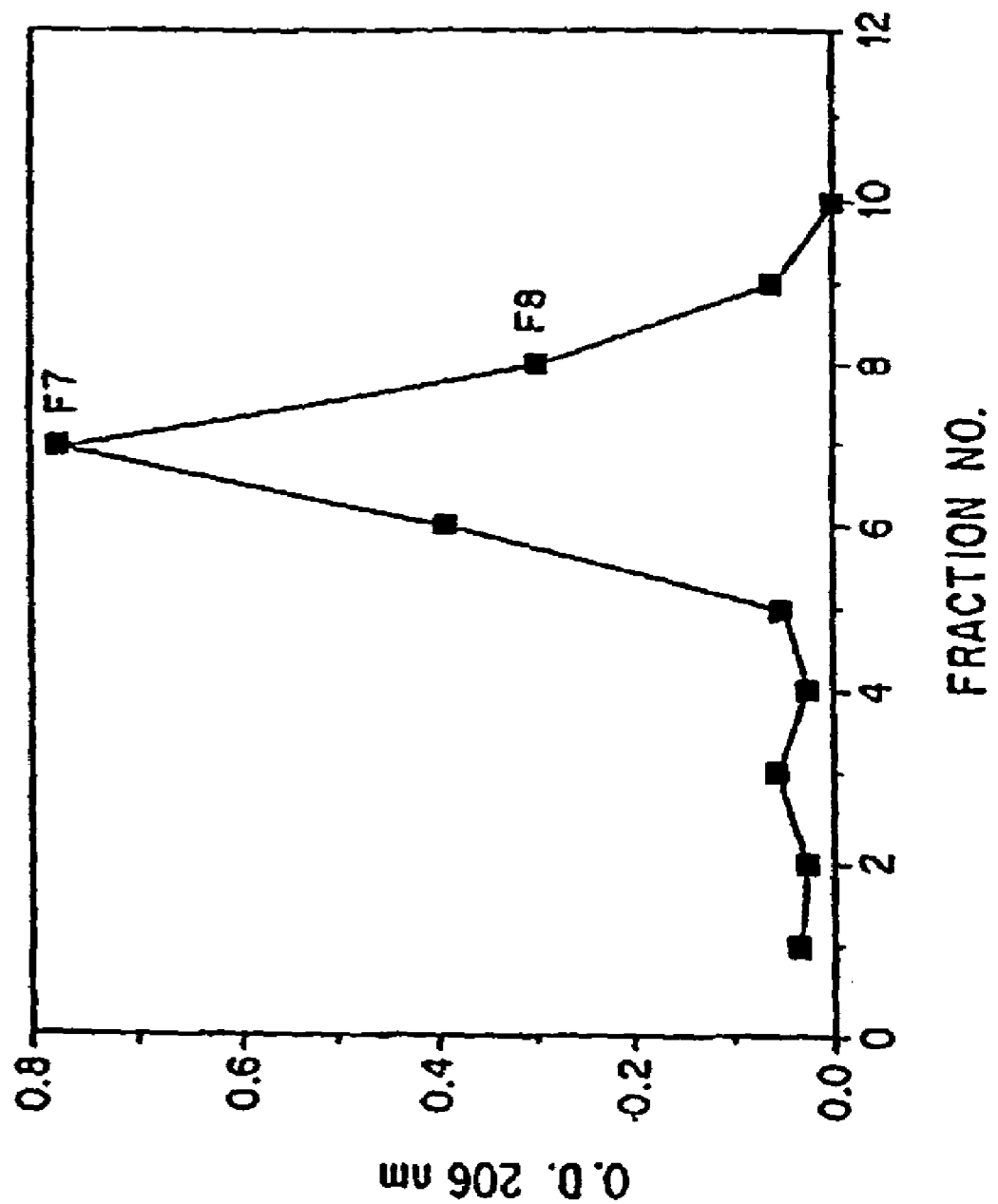
FIG. 22 illustrates the uv absorption of fractions F7 and F9 obtained from the Sepharose 4B column separation of heparanase-degraded ECM.
Figure 23:
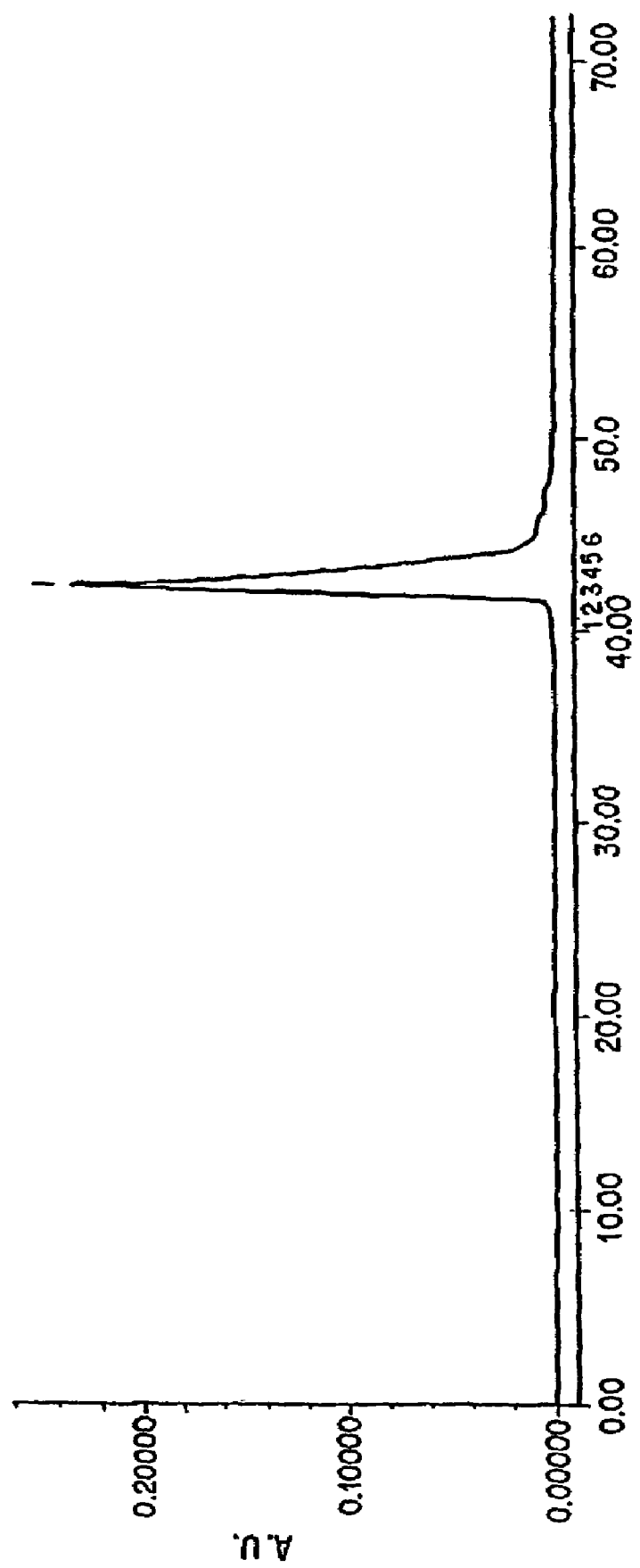
FIG. 23 illustrates the substantially pure peak obtained from the SAX-HPLC chromatography of combined fractions F7 and F8.

6.15. Isolation of a Disaccharide from ECM Degradation Products Including SAX-HPLC Chromatography An ECM-coated plate was incubated with 20 µl of mammalian heparanase (0.5 mg/ml) in 1 ml PBS buffer (which had been preadjusted to pH 6.2 by citric acid) for 48 hours at 37° C. The medium was then collected and applied on a Sepharose-4B column (0.7×35 cm). The mobile phase was PBS buffer at a flow rate of 5 ml/hr. Fractions of 1.6 ml were collected and monitored at 206 nm. (FIG. 22). Fractions nos. 7-8 were combined and freeze-dried; the powder was resuspended in 1/10 of the initial volume. Samples (100 µl) were injected into an HPLC column (Toyo Soda TSWK-Gel G3000SW 7.5 mm×50 cm and G2000SW 7.5 mm×50 cm, in series with 7.5 mm×10 cm guard from Phenomenex), as before. The mobile phase was 0.5 M NaCl at a flow rate of 1 ml/min. One ml fractions were collected and monitored at 206 and 232 nm (FIG. 23). The peak labeled "1" was collected from ten identical runs. The substantially homogeneous fractions were combined and freeze dried.

The material was resuspended in 2 ml double deionized water and desalted on a Sephadex G-10 column (26×150 mm) eluted at 1.6 ml/min with double deionized (DD) water. One ml fractions were collected and monitored at 232 nm and for conductivity (to determine NaCl content). Desalted fractions were combined, freeze dried and resuspended in 1 ml DD $H_2O$. A 1 ml sample, prepared by combining 100 µl of the resuspended solution and 900 µl of 0.2 M NaCl at pH 3.5, was injected into an analytical SAX-HPLC column (4.6×250 mm, packed with Spherisorb, 5-µm particle size). The flow rate was 1.5 ml/min and an NaCl linear gradient program was employed as follows:

| Time/Buffer (min) | A (%) | B (%) | C (%) |
|---|---|---|---|
| 0 | 100 | 0 | 0 |
| 2 | 100 | 0 | O |
| 35 | 38 | 62 | 0 |
| 40 | 38 | 62 | 0 |
| 45 | 0 | 100 | 0 |
| 47 | 0 | 100 | 0 |
| 50 | 0 | 0 | 100 |
| 55 | 0 | 0 | 100 |
| 58 | 100 | 0 | 0 |
| 60 | 100 | 0 | 0 |

A = 0.2 M NaCl, pH 3.5
B = 1.5 M NaCl, pH 3.5
C = $H_2O$

The column eluent was monitored at 232 nm (FIG. 24) and peak A23/4 was collected and tested for TNF inhibition. The $Inh_{max}$ for this SAX-HPLC fraction was found to be 60% at a concentration of 0.1 pg/ml, giving an "R" value of 600%×(pg/ml)$^{-1}$.

Figure 25B:
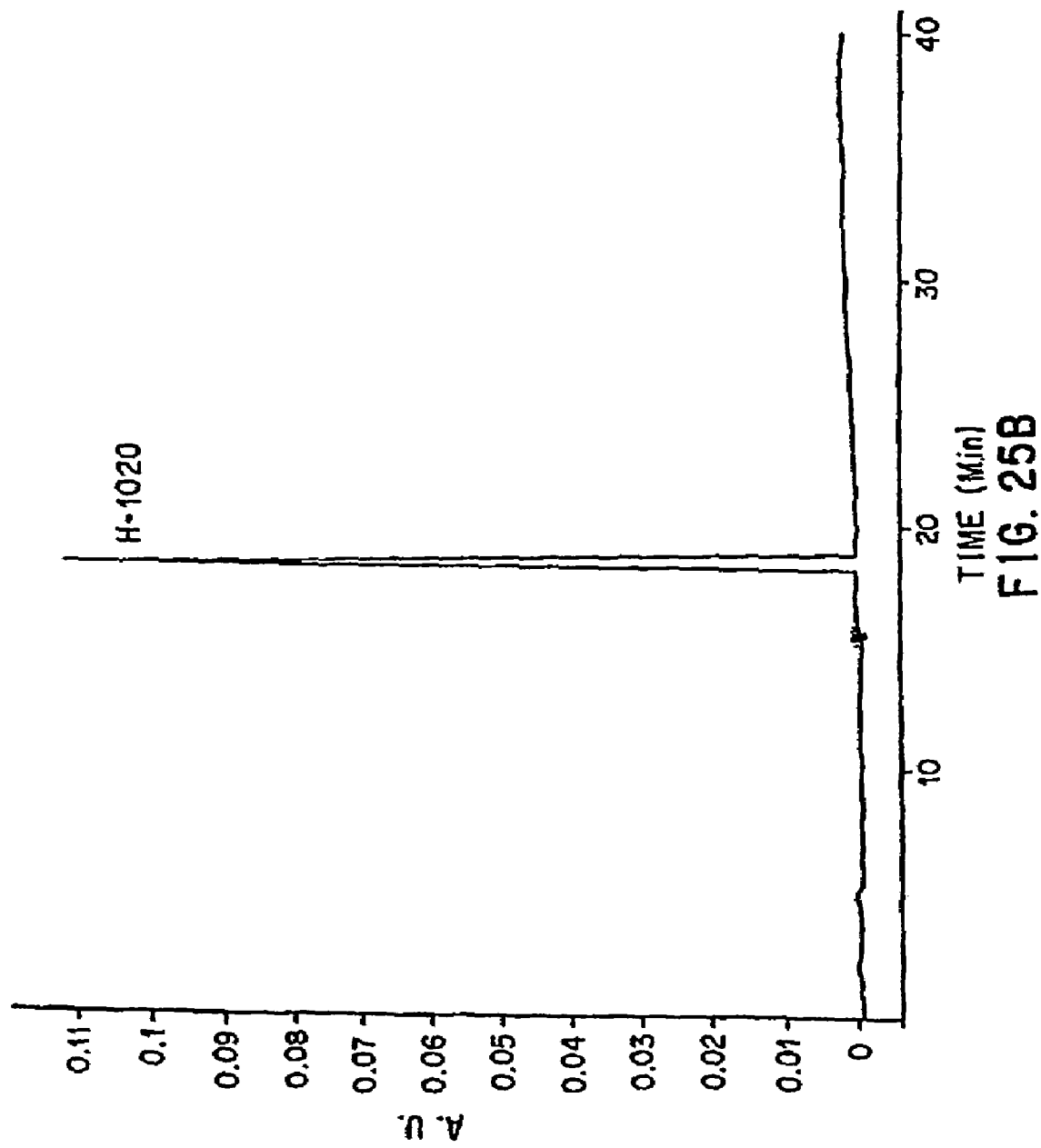
Figure 25C:
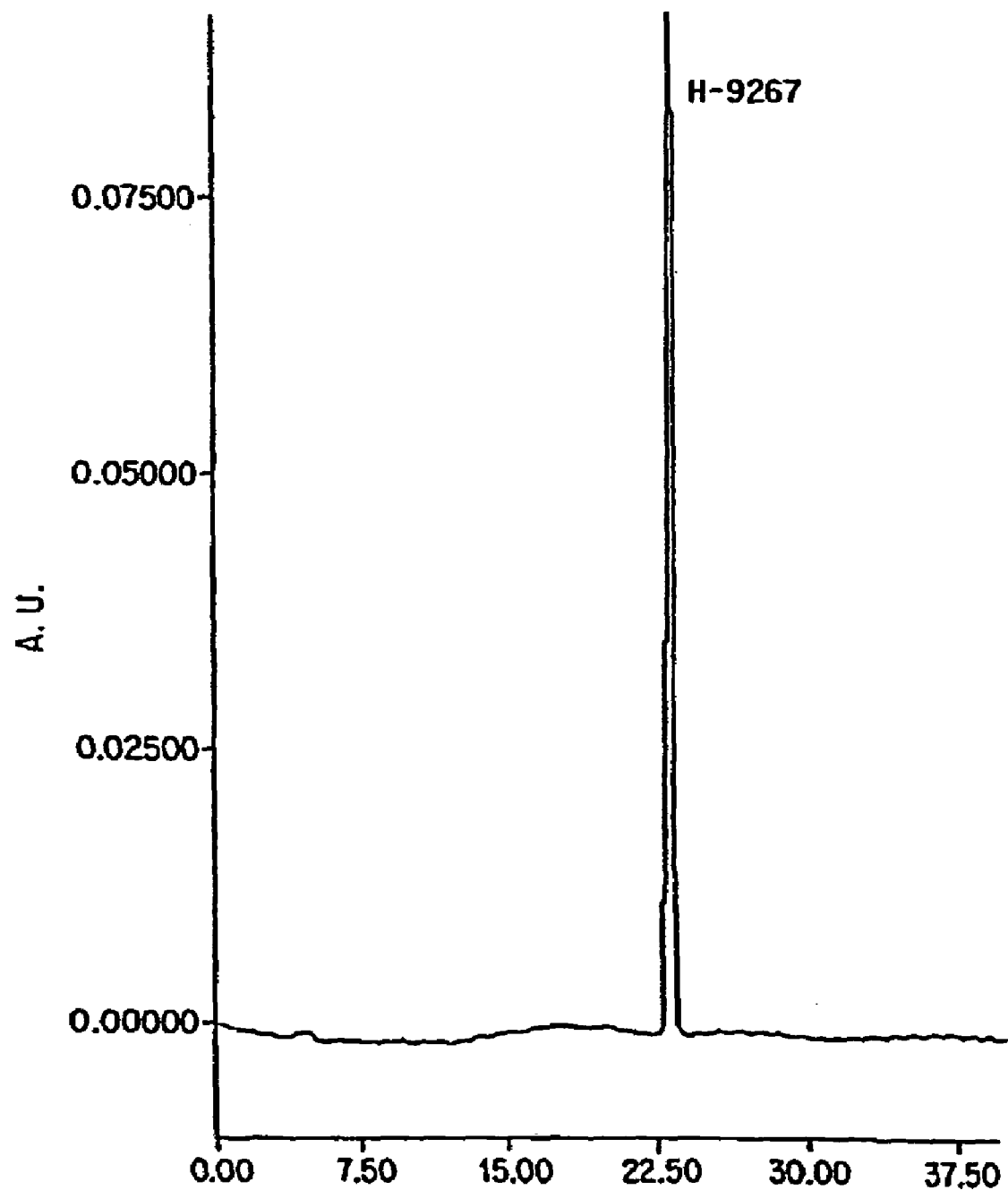

Heparin disaccharide standards with different levels of sulfation were injected into the SAX-HPLC column under identical conditions. The elution profiles of these standards are presented in FIGS. 25A-C. As can be seen from these Figures, the disaccharide standards gave different retention times, with an unsulfated disaccharide (Sigma Product No. H-0895) eluting fastest (FIG. 25A), a disulfated disaccharide (Sigma Product No. H-1020) eluting at less than 20 minutes (FIG. 25B), and a trisulfated disaccharide (Sigma Product No. 9267) eluting last (FIG. 25C). The trisulfated disaccharide standard H-9267 provided a retention time that was very similar to that obtained for peak A23/4 (i.e., 23.07 min. vs and 23.10 min., respectively).

6.16. Results of In Vitro Human PBL Bioassays for Various Substances

The results of in vitro bioassays using human PBLs for various active substances and starting "mixtures" are presented in Table XVIII for the products obtained from the degradation of ECM, including a peak "P1" from FIG. 20. Whereas, P1 provided an "R" value of 10%×(pg/ml)$^{-1}$, the starting DECM "soup" gave an "R" value of 0.000053%× (pg/ml)$^{-1}$.

TABLE XVIII

Effect of ECM + MM5 Heparanase (DECM "Soup"), Sepharose 4B Fractions of "Soup", and HPLC Fractions of Sepharose 4B Fractions on the Secretion of Active TNF Using Human PBL Bioassay.

| Test Material | conc (pg/ml) | Bioassay of TNF Activity (%) | "R" value % × (pg/ml)$^{-1}$ |
|---|---|---|---|
| DECM "Soup" | 1 × 10$^6$ | $Inh_{max}$ (53%) | 5.3 × 10$^{-5}$ |
| Seph. 4B-F5 | 100 | $Inh_{max}$ (50%) | 0.5 |
| Seph. 4B-F6 | 100 | $Inh_{max}$ (60%) | 0.6 |
| Seph. 4B-F7, 8 | 100 | $Inh_{max}$ (81%) | 0.8 |
| F5/HPLC-F73 | 10 | $Inh_{max}$ (87%) | 8.7 |
| F5/HPLC-F65 | 10 | $Inh_{max}$ (78%) | 7.8 |
| F5/HPLC-F22 | 10 | $Inh_{max}$ (33%) | 3.3 |
| F6/HPLC-F86 | 10 | $Inh_{max}$ (43%) | 4.3 |
| P1 | 10 | $Inh_{max}$ (100%) | 10.0 |

6.17. Isolation of Oligosaccharides from Heparin Degradation Products

Figure 26:
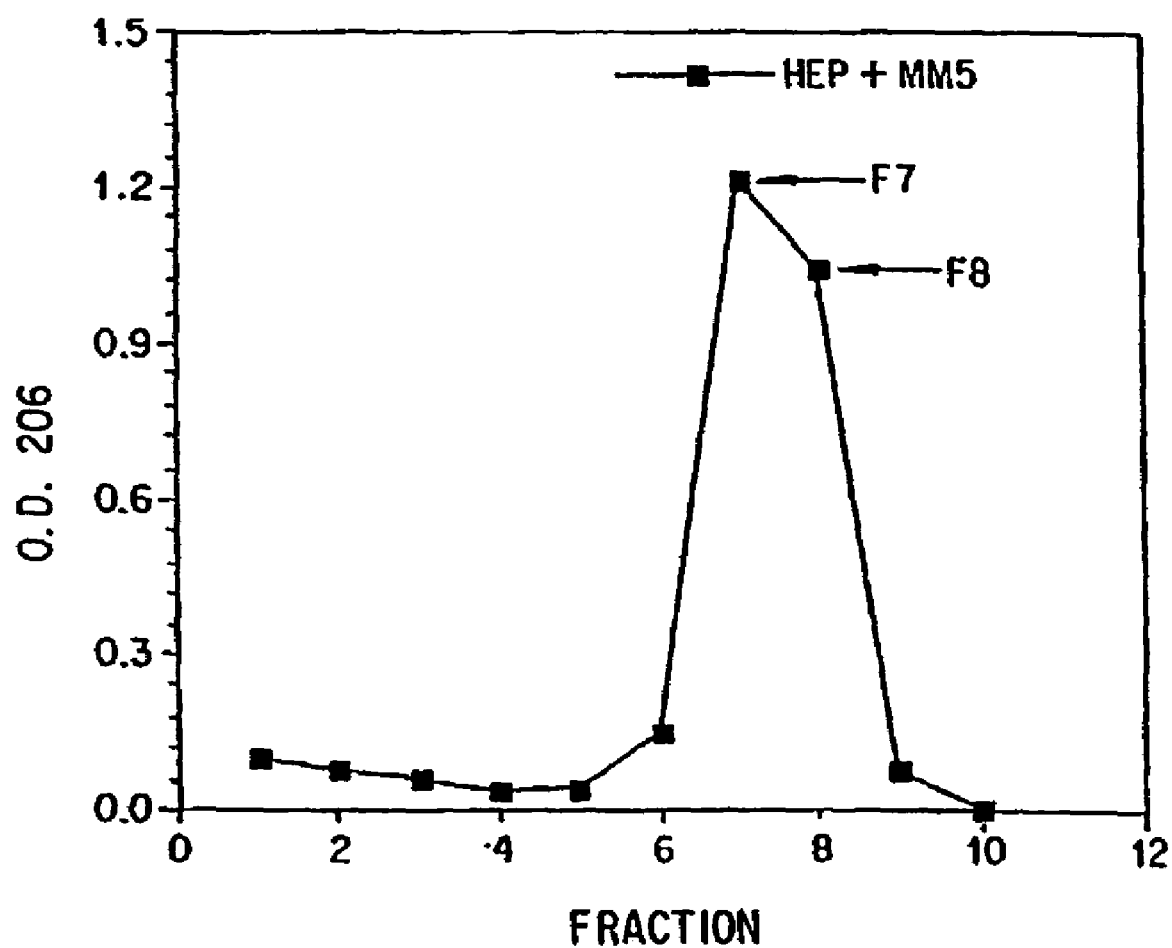
FIG. 26 illustrates the Sepharose 4B column separation of a mixture obtained from the heparanase (MM 5) treatment of Heparin, yielding fractions F7 and F8.
Figure 27:
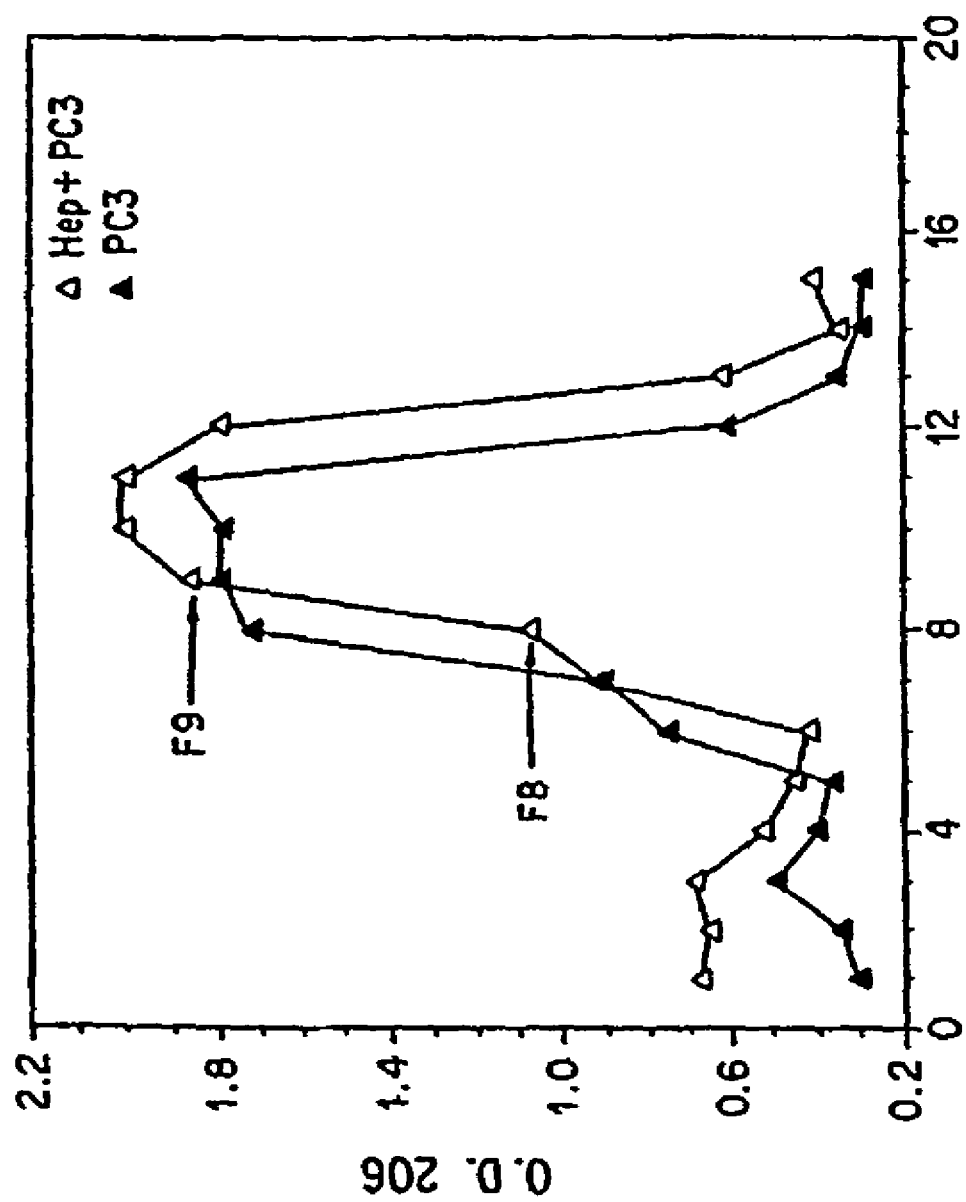
FIG. 27 illustrates the absorption at 206 nanometers of various fractions obtained from the sepharose 4B chromatography of PC3 heparanase alone and Heparin+PC3.
Figure 28A:
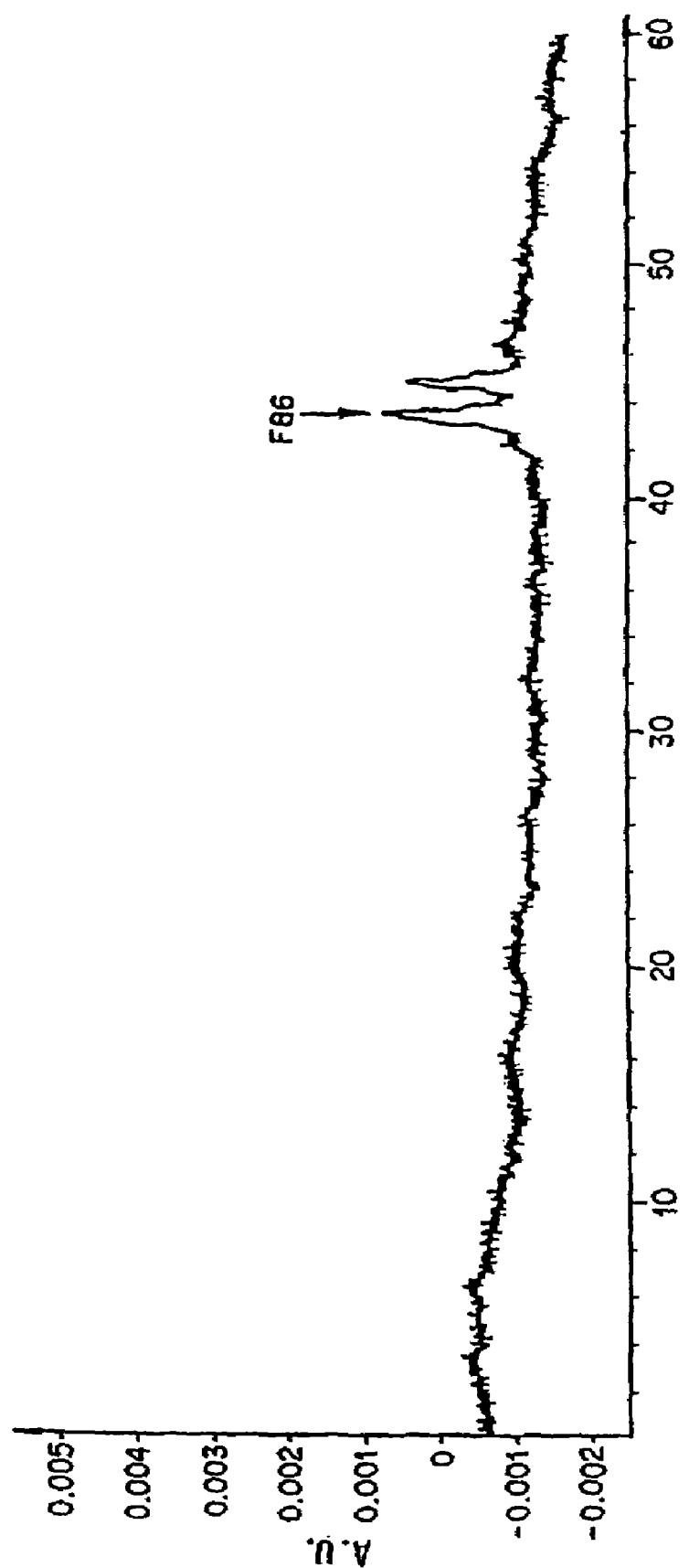
FIGS. 28A and 28B illustrate additional fractions obtained from the HPLC separation of fraction F7 from FIG. 26.
Figure 28B:
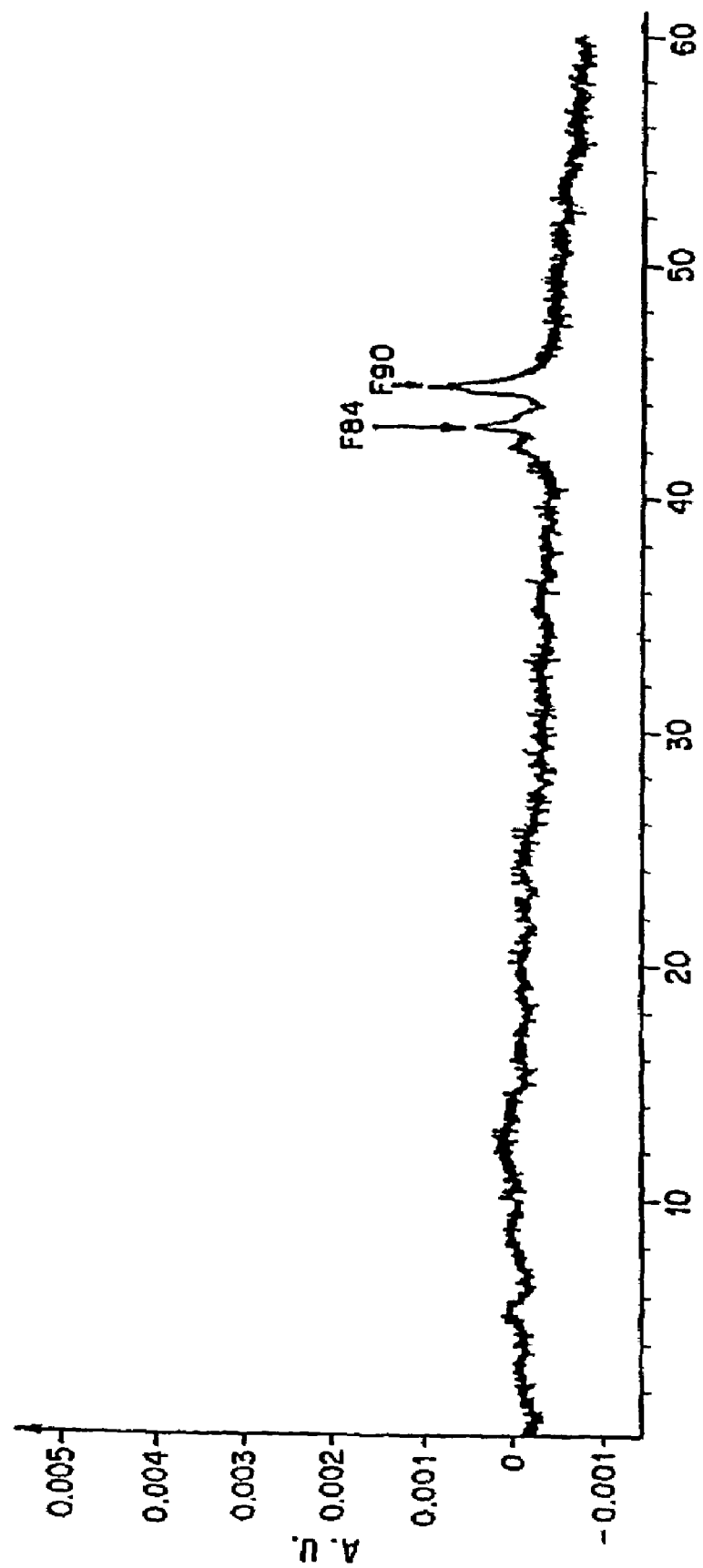

In a manner similar to that described, above, for the degradation of ECM, intact heparin was treated with heparanase enzymes obtained from various sources, designated herein as MM5 and PC3 See, Shoseyov, O. et al., *Biochem. Biophys RES. COMM.* (1990) 169:667-672, for the preparation of PC3 enzyme). Some of the starting degradation mixtures were separated on Sepharose 4B (see, FIG. 26 for Heparin+MM5 Sepharose 4B fractions F7 and F8, and FIG. 27 for Sepharose 4B chromatography of Heparin+PC3 and PC3 alone). Still other fractions were further separated by the HPLC II methods described above (See, FIGS. 28A and 28B for fractions F7/HPLC-F86, -F84, and -F90). "Intact" heparin and Fragmin were also subjected to direct HPLC II conditions and selected fractions were likewise isolated (HPLC-F90 from Fragmin is presented in FIG. 29). The results of in vitro bioassays using human PBLs for various active substances and starting "mixtures" are presented in Table XIX, including the products obtained from the degradation of heparin.

TABLE XIX

Effect of Intact Heparin, Heparin + MM5 or PC3 "Soups", and Selected Sepharose 4B and HPLC Fractions of Same on the Secretion of Active TNF Using Human PBL Bioassay.

| Test Material | conc (pg/ml) | Bioassay of TNF Activity (%) | "R" value % × (pg/ml)$^{-1}$ |
|---|---|---|---|
| Intact Heparin | a | No effect | 0 |
| Hep/HPLC-F90 | a | No effect | 0 |
| Additional Heparin Fractions | | | |
| F7/HPLC-F86 | 0.1 | $Inh_{max}$ (26%) | 260 |
| F8/HPLC-F84 | a | No effect | 0 |
| F8/HPLC-F90 | a | No effect | 0 |
| Hep/PC3 "Soup" | 0.1-10 × 10$^6$ | No effect | 0 |
| Seph. 4B-F9 | 100 | $Inh_{max}$ (50%) | 0.5 |
| Seph. 4B-F8 | 100 | $Inh_{max}$ (40%) | 0.4 |
| PC3 only | a | No effect | 0 |
| Seph. 4B-F8 | a | No effect | 0 |
| Seph. 4B-F9 | a | No effect | 0 | a At a conc range of 1 µg/ml-0.01 pg/ml

6.18. Results of In Vivo DTH Reactivity of Mice Treated with Various Substances A variety of substances were tested under in vivo bioassay conditions and found to inhibit the experimental DTH sensitivity of mice to different extents depending on their state of purification. The mice were treated with an active substance, as described in Sections 5.1 and 5.2, above. Generally, the substances that have been purified to substantial homogeneity by high pressure liquid chromatography provide "R" values in the tens of thousands. The results for one group of experiments are presented in Table XX.

TABLE XX

Weekly Treatment of Mice with Various Substances and Their Effect on the DTH Sensitivity of Mice.

| Test Material | Dose (μg/gm mouse) | DTH Response ($10^{-2}$ mm) | Inhibition of DTH (%) | "R" value % × $(\mu g/g)^{-1}$ |
|---|---|---|---|---|
| None (−) Control | — | 17.2 ± 22 2 | 0 | — |
| 0.5 M NaCl | — | 16.5 ± 1.5 | 5 | — |
| Intact Heparin Fragmin | a | — | No effect | 0 |
| Batch 38609 DECM | 0.2 | 3 ± 1 | 85 | 425 |
| MM5 "Soup" | a | — | No effect | — |
| Seph. 4B-F6 | 0.032 | 16.5 ± 5 | 5 | — |
|  | 0.016 | 16 ± 2 | 10 | — |
|  | 0.0032 | 14 ± 2 | 20 | — |
|  | 0.0006 | 7.1 ± 1 | 65 (max) | 110,000 |
| F6/HPLC-F9 | 0.032 | 11 ± 2 | 40 | — |
|  | 0.01 | 17 ± 2 | 0 | — |
|  | 0.002 | 6 ± 0.5 | 70 | — |
|  | 0.0006 | 6 ± 1.2 | 70 (max) | 120,000 |
| F6/HPLC-F11 | 0.02 | 17 ± 3 | 0 | — |
|  | 0.01 | 13 ± 1 | 25 | — |
|  | 0.001 | 9.5 ± 2.5 | 55 | — |
|  | 0.0006 | 2.8 ± 0.5 | 90 (max) | 150,000 |
| F6/HPLC-F12 | 0.02 | 18 ± 2 | 0 | — |
|  | 0.01 | 15 ± 2 | 15 | — |
|  | 0.001 | 8.2 ± 1.5 | 60 | — |
|  | 0.0006 | 4 ± 1 | 80 (max) | 130,000 | a At a dosage range of 0.04-0.0004 μg/gm mouse.

As noted in Table XX, intact heparin and the starting ECM+MM5 "soup" exhibited no in vivo effect. In the latter case, no effect is obtained most likely because of the counterbalancing effects of inhibitory and augmentative components. A fresh sample of Fragmin (Batch 38609) exhibited a modest "R" value, comparable to that obtained in earlier experiments (See, first entry, Table IX). A Sepharose 4B fraction manifested a slightly lower "R" value than the corresponding fractions obtained under HPLC II conditions.

The results from another set of experiments, listed in Table XXI, confirmed the absence of any effect from the starting ECM+MM5 "soup". Notably, an HPLC II fraction, no. F5/HPLC-L22, showing very high specific regulatory activity when injected subcutaneously into mice ("R" value=454,545%×$(\mu g/gm)^{-1}$), also demonstrated oral activity albeit at a higher dose ("R") value+5,000%×$(\mu g/gm)^{-1}$). It is also apparent from Table XXI that active substances isolated from the ECM have greater in vivo specific regulatory activity than those obtained from Fragmin. Hence, the apparent desulfation reduces the specific inhibitory activity of the active substances of the present invention. In fact, under in vitro bioassay conditions, augmentative "R" values are obtained from such "desulfated" disaccharides.

Further experiments have also demonstrated that galactosamine, a monosaccharide or simple sugar having no sulfate groups, is capable of acting as an antagonist of the inhibitory activity of the sufated oligosaccharides of the present invention. Thus, it is also possible that the desulfated oligosaccharides act as direct augmentative components or as antagonists of the specific inhibitory activity of the carboxylated and/or sulfated oligosaccharides. The observations of the present investigators are also consistent with a mechanism by which certain substances (e.g., a trisulfated disaccharide) behave as agonists of an as yet unidentified natural inhibitor of active TNF-α secretion.

TABLE XXI

In Vivo DTH Reactivity Data for Mice Treated Subcutaneously With Various Substances

| Test Material | Dose (μg/gm mouse) | DTH Response ($10^{-2}$mm) | $Inh_{max}$ (%) | "R" value % × $(\mu g/gm)^{-1}$ |
|---|---|---|---|---|
| ECM + MM5 "Soup" | a | 20.4 ± 0.7 | No effect | 0 |
| F5/HPLC-L22 | 0.008[b] | 13.2 ± 1.3 | 40 ± 12% | 5,000 |
| F5/HPLC-L22 FRAGMIN | 0.000132 | 9.7 ± 1.3 | 60 ± 17% | 454, 545 |
| FR/HPLC-2 | 0.00048 | 8.5 ± 1.3 | 70 ± 20% | 145, 833 | a At 4 dose range of 6.04-0.0004 μg/gm mouse.
[b]Administered orally.
Positive control group had DTH response of 20.0 ± 1.1 and the negative control group had a DTH response of 2.0 ± 1.0.

6.19. Comparative In Vivo Activity of SAX-HPLC Fractions Versus Known Disaccharide Markers Two disaccharide markers were tested under in vivo conditions to determine their ability inhibit the relative DTH reactivity of mice. As shown in Table XXII, the two markers (H-1020 and H-9267) exhibited moderate activity having "R" values between 140,000-160,000%×$(\mu g/gm)^{-1}$ when injected subcutaneously into mice. The marker, H-1020, was also tested orally and found to have modest activity ("R" value=531%×$(\mu g/gm)^{-1}$). The H-1020 marker is an O,N-di-sulfate, whereas the H-9267 marker is an O,O,N-tri-sulfate. Their structures are depicted, below.

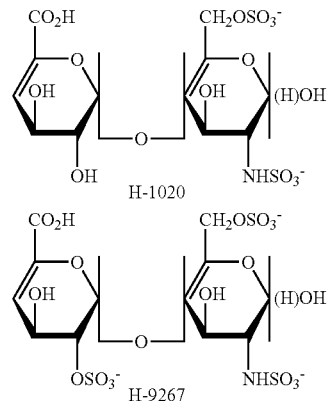

Figure 30:
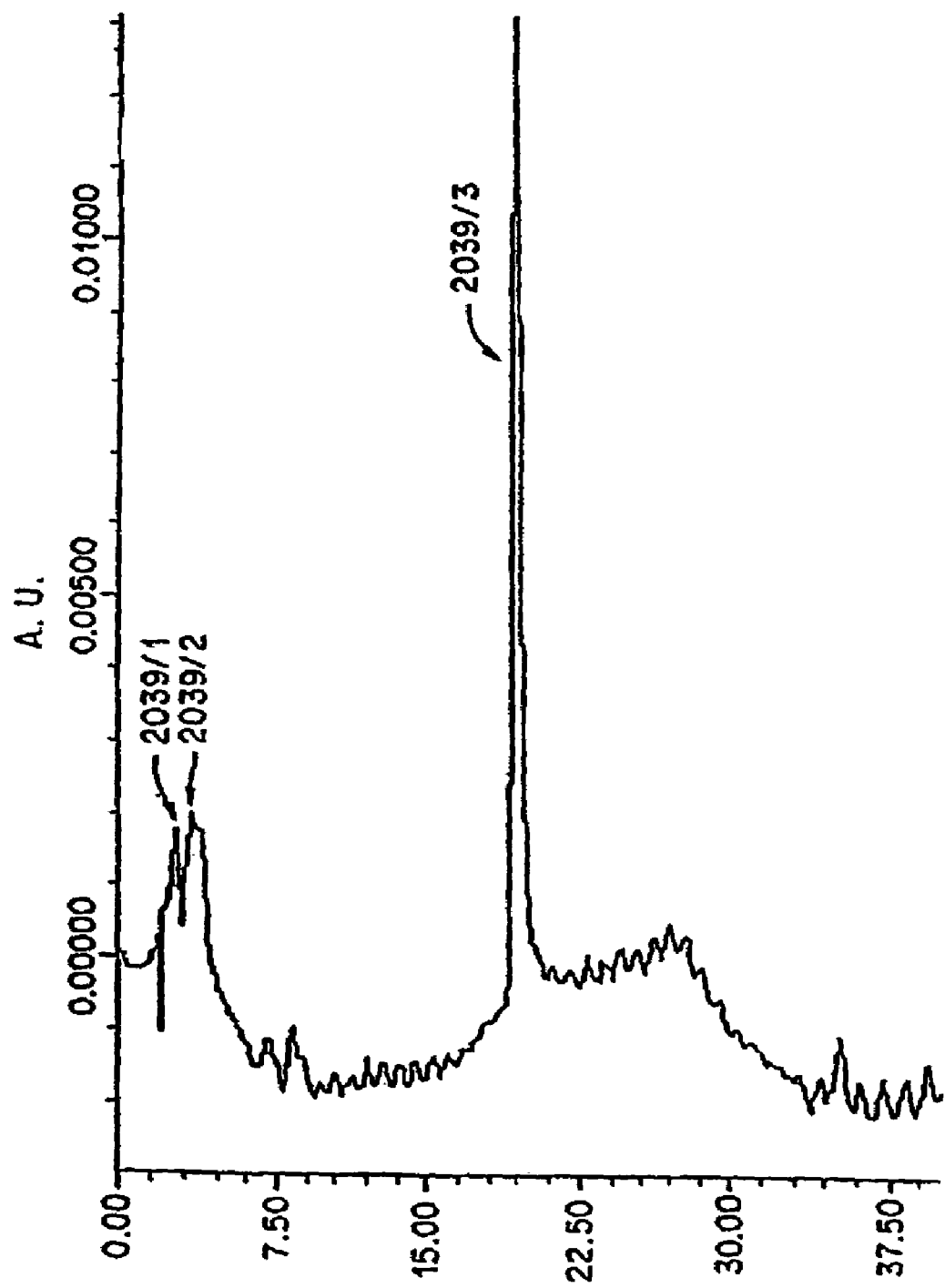
FIG. 30, on the other hand, illustrates the chromatogram that is obtained from a SAX-HPLC separation of an aged sample of A23/4.
Figure 31:
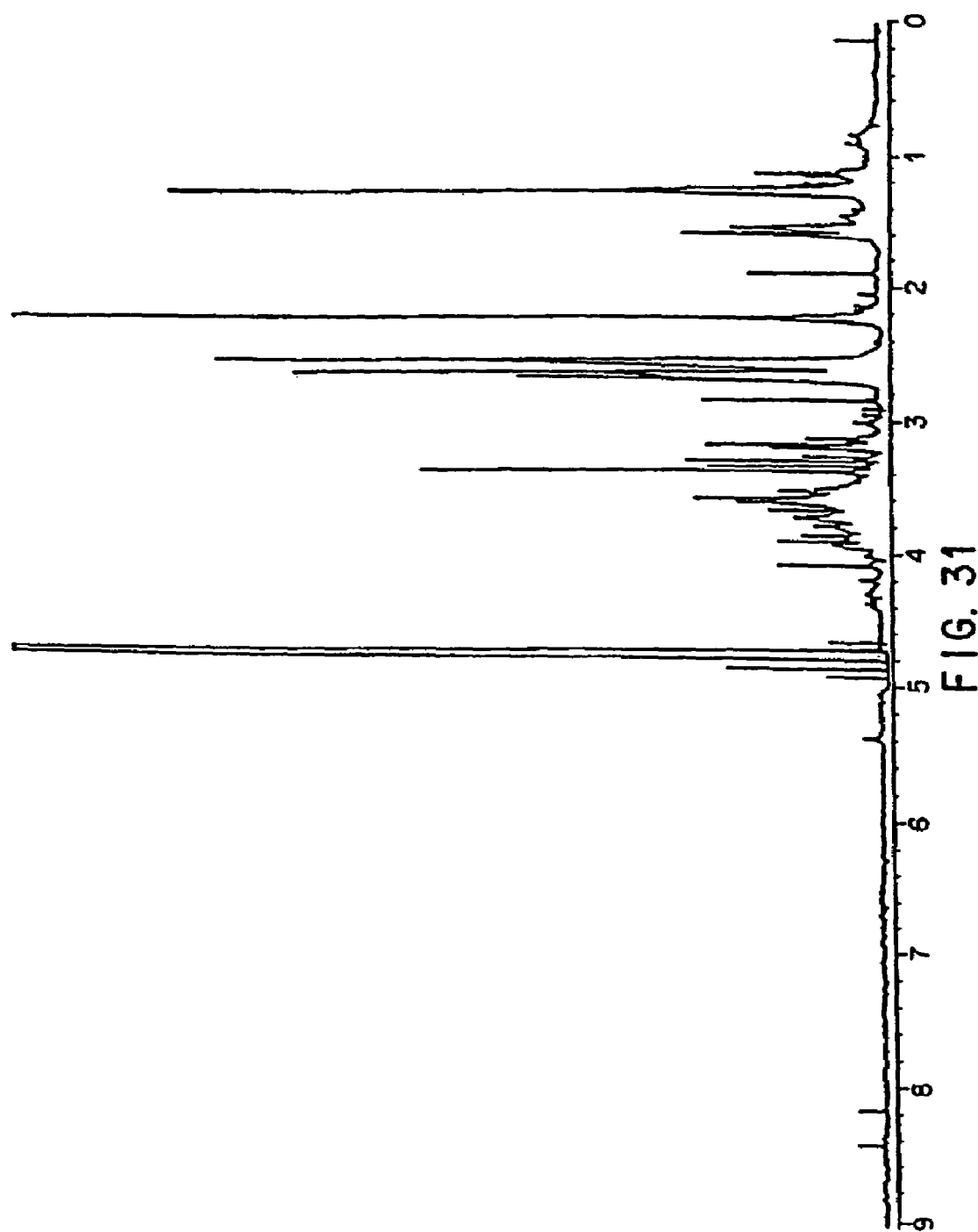
FIG. 31 illustrates the proton NMR spectrum of a 20 microgram sample of an ECM-derived disaccharide obtained from HPLC chromatography, as shown in FIG. 23.

As presented in Table XXII, the SAX-HPLC fraction L22/SAX-A23/4 (FIG. 24) provided further improvement over the already high specific regulatory activity of F5/HPLC-L22, giving an "R" value of 630,303%×(μg/gm)$^{-1}$ compared with an "R" value of 454,545%×(μg/gm)$^{-1}$ for F5/HPLC-L22 (Table XXI). It was discovered, however, that this disaccharide substance, with a retention time through the SAX-HPLC column which is almost identical to the retention time of H-9267, loses its sulfate groups at pH ~3.5 over a few days at room temperature. Thus, reanalysis of an aged sample through a SAX-HPLC column revealed that the original peak at 23.10 min. had given way to three major peaks, designated 2039/1, 2039/2, and 2039/3 in FIG. 30, all having retention times shorter than A23/4. Peak 2039/3, having a retention time similar to the H-1020 marker, is likely to have lost an N-sulfate group. Peaks 2039/1 and 2039/2 likely correspond to monosulfated or fully desulfated disaccharides. (Their retention times are comparable to a disaccharide marker, H-0895, an N-acetylglycosaminoglycan having no sulfate groups.)

These "desulfated" substances were each collected and tested under the in vivo DTH bioassay conditions and found, surprisingly, to have only moderate or no inhibitory activity. (See, Table XXII). Indeed, under the in vitro human PBL assay, all three peaks manifested augmentation of active TNF-α secretion. These in vitro results are given, immediately below:

| SAX-HPLC Peak | conc (pg/ml) | Aug$_{max}$ (%) | "R" value % × (μg/ml)$^{-1}$ |
|---|---|---|---|
| 20391/1 | 1 | 5 | 5 |
| 2039/2 | 1 | 35 | 35 |
| 2039/3 | 1 | 42 | 42 |

TABLE XXII

Additional In Vivo Results Using a Variety of Disaccharides Administered Subcutaneously

| Test Material | Dose (μg/gm mouse) | DTH Response (10$^{-2}$ mm) | Inh$_{max}$ (%) | "R" Value % × (μg/gm)$^{-1}$ |
|---|---|---|---|---|
| PBS (Pos. Control) | — | 18.6 ± 0.7 | — | — |
| Naive (Keg. Control) | — | 1.4 ± 0.2 | — | — |
| SAX-HPLC Fractions | | | | |
| A23/4 | 0.000132 | 3 ± 1 | 83 | 630,303 |
| 2039/3 | 0.0005 | 3.1 ± 1.1 | 83 | 166,000 |
| 2039/1 | 0.000132 | 18.5 ± 1.1 | No effect | 0 |
| "Markers" | | | | |
| H-1020 | 0.0005 | 4.7 ± 0.7 | 73 | 146,000 |
| H-1020 | 0.128$^a$ | 5.9 ± 0.9 | 68 | 531 |
| H-9267 | 0.0005 | 3.5 ± 1 | 80 | 160,000 |

$^a$Administered orally.

6.19.1. Further Results of the Ability of Selected Disaccharides to Regulate the In Vivo Production of Active TNF-α

Additional experiments were performed in which selected disaccharide molecules, commercially available from Sigma Chemical Co. and identified herein by their respective Sigma Catalog Nos., were tested for their the ability to inhibit or augment the experimental DTH reaction in mice and, thus, offer an indication of their ability to regulate the production by these mammals of active TNF-α.

In particular, CD1 mice (available from the Weizmann Institute Animal Breeding Center, Rehovot, Israel), 4-12 mice per group were treated as described in Section 5.2 or 6.8.

The results of the various experiments are summarized in Table XXIIIA, below. As can be seen, four of the eleven disaccharides tested exhibited an inhibitory effect on the swelling of the ears of the mice in response to the administered oxazolone. The inhibition of the T cell-mediated inflammatory response is thus seen as an indication that the disaccharides exhibiting a non-zero "R" value can down regulate the production of active TNF-α. From the results listed in the Table, the "R" values range from a relatively modest 65,000%×(μg/gm)$^{-1}$ to over about 1,500,000%×(μg/gm)$^{-1}$. It should be pointed out that a high "R" value is not necessarily the most desirable characteristic of the active compounds of interest. In particular, the dose "window" within which a particular compound exhibits physiological effects should be as broad as possible so that there is less likelihood that the dose administered will fall outside the effective dose range. As indicated in the footnotes of Table XXIIIA. the molecule H-9392 appears to have the broadest dose window, 0.000132-0.004 μg/gm, of the compounds tested.

Equally evident from the results is the surprising ability of one of the eleven disaccharides tested to augment the swelling caused by the experimental DTH T cell reaction. Compound H-0895, which has no sulfate groups, displays a tremendous effect on the degree of swelling at the very low dose of about 1.2 picograms disaccharide per gram mouse. The resulting "R" value of about 76,700,000%×(μg/gm)$^{-1}$ is presently unrivaled.

TABLE XXIIIA

Additional In Vivo Results Using a Variety of Disaccharide Markers Administered Subcutaneously.

| Test material | Dose (μg/gm) | DTH (10$^{-2}$ mm) | Inh$_{max}$ (%) | "R" value % × (μg/gm)$^{-1}$ |
|---|---|---|---|---|
| H-9392$^a$ | 0.0012 | 4.2 ± 0.7 (17.8 ± 0.9) | 78 | 6.5 × 10$^4$ |
| H-1020$^b$ | 0.0004 | 6.7 ± 1.1 (19.6 ± 1.2) | 66 | 1.65 × 10$^5$ |
| H-9267$^c$ | 0.0004 | 7.2 ± 1 (19.6 ± 1.2) | 64 | 1.60 × 10$^5$ |
| H-9517$^d$ | 0.00004 | 7.6 ± 1 (20.4 ± 0.7) | 62 | 1.55 × 10$^6$ |
| H-0895$^e$ | 0.0000012 | 37.3 ± 0.7 (18.9 ± 0.7) | +92 | 7.67 × 1.0$^7$ |
| H-9017$^f$ | N.E. | | | 0 |
| H-8642$^g$ | N.E. | | | 0 |
| H-9142$^h$ | N.E. | | | 0 |
| H-8767$^i$ | N.E. | | | 0 |

TABLE XXIIIA-continued

Additional In Vivo Results Using a Variety of Disaccharide Markers Administered Subcutaneously.

| Test material | Dose (µg/gm) | DTH ($10^{-2}$ mm) | Inh$_{max}$ (%) | "R" value % × (µg/gm)$^{-1}$ |
|---|---|---|---|---|
| H-8892[j] | N.E. | | | 0 |
| H-1145[k] | N.E. | | | 0 |

[a]H-9392 is 2-O-Sulfate-4-deoxy-4-en-iduronic acid-(α-1,4)-2-deoxy-2-N-sulfateglucosamine. The PBS (positive control) value for this data set is presented in parenthesis. The swelling of naive (unimmunized) mice was 2.0 ± 0.5 mm. This value was used for all the above calculations. The effective dose range for inhibition ≧50% of control was 0.000132-0.004 µg/gm.
[b]H-1020 is 4-deoxy-4-en-iduronic acid-(α-1,4)-2-deoxy-2- N-sulfate-6-O-sulfateglucosamine. The effective dose range for inhibition ≧50% of control was 0.00004-0.0004 µg/gm. The "R" value presented in this Table compares favorably with the early "R" value reported previously in Table XXIII, above. These results indicate a remarkable reproducibility of the in vivo test method in different groups of CD1 strain mice.
[c]H-9267 is 2-O-sulfate-4-deoxy-4-en-iduronic acid-(α-1,4)-2-deoxy-2-N-sulfate-6-O-sulfateglucosamine. The effective dose range for inhibition ≧50% of control was narrow.
[d]H-9517 is 2-O-sulfate-4-deoxy-4-en-iduronic acid-(α-1,4)-2-deoxy-2-N-acetyl-6-O-sulfateglucosamine. The effective dose range for inhibition ≧50% of control was 0.00004-0.00012 µg/gm.
[e]H-0895 is 4-deoxy-4-en-iduronic acid-(α-1, 4)-2-deoxy-2- N-acetylglucosamine. This result indicates an augmentation of the DTH reaction. The effective dose range for augmentation ≧50% of control was 0.000001-0.00004 µg/gm.
[f]H-9017 is 4-Deoxy-4-en-iduronic acid-(α-1,4)-2-deoxy-6- O-sulfateglucosamine. "N.E." indicates that no effect was observed at the tested dosage range of 0.000004-4 µg/gm mouse.
[g]H-8642 is 4-deoxy-4-en-iduronic acid-(α-1,4)-2-deoxy-2-N-acetyl-6-O-sulfateglucosamine.
[h]H-9142 is 2-O-sulfate-4-deoxy-4-en-iduronic acid-(α-1,4)-2-deoxyglucosamine.
[i]H-8767 is 2-O-sulfate-4-deoxy-4-en-iduronic acid-(α-1,4)-2-deoxy-2-N-acetylglucosamine.
[j]H-8892 is 2-O-sulfate-4-deoxy-4-en-iduronic acid-(α-1,4)-2-deoxy-6-O-sulfateglucosamine.
[k]H-1145 is 4-deoxy-4-en-iduronic acid-(α-1,4)-2-deoxy-2-N-sulfateglucosamine.

The structures of four inhibitory disaccharide compounds, H-9392, H-9517, H-1020 and H-9267, are presented bellow.

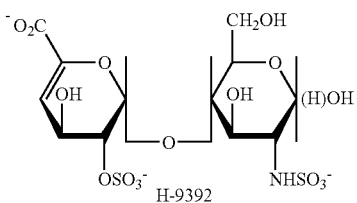

Of the eleven disaccharides tested six failed to exhibit any consistent effects and, thus, may be classified as "neutral." The structures of these neutral compounds are presented below.

Of the eleven, one disaccharide augmented the effects of the experimental DTH reaction. This compound, H-0895, has the structure presented below.

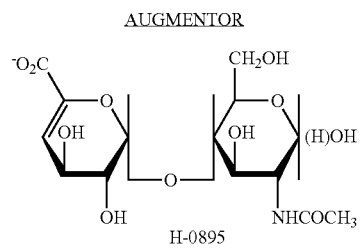

AUGMENTOR
H-0895

It is thus possible to propose a generic formula that embodies the structural characteristics of the inhibitory compounds. This generic formula (H-GENUS) is shown below:

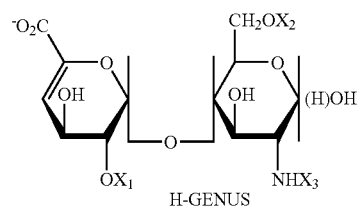

H-GENUS in which, $X_1$ is H or $SO^{3-}$; $X_2$ is H or $SO^{3-}$; and $X_3$ is $SO^{3-}$ or $COCH_3$, provided that if $X_3$ is $SO^{3-}$, then at least one of $X_1$ or $X_2$ is $SO^{3-}$ and if $X_3$ is $COCH_3$, then both $X_1$ and $X_2$ are $SO^{3-}$. In terms of a compound having a fairly broad window of effective dosages, $X_1$ is preferably $SO^{3-}$, $X_2$ is preferably H, and $X_3$ is preferably $SO^{3-}$ (i.e., H-9392 has the broadest window of effective inhibitory dosages).

One may also observe from the results presented above that, in terms of inhibition, the preferred substituent at the glycosamine nitrogen is sulfate. With a sulfate at the 2-N position of glucosamine ($X_3$), inhibitory activity is observed with the presence of just one other sulfate either at the 2-position of the iduronic acid residue or the 6-position of the glycosamine. The presence of two additional sulfates at both hydroxyl positions would also work, but the absence of any additional sulfate (as in H-1145) produces a "neutral" compound.

By contrast, the introduction of an acetyl group at the 2-N position of glucosamine requires the presence of two additional sulfates, one each for 2-position of the iduronic acid ($X_1$) and the 6-position of the glucosamine ($X_2$) The absence of any substituent at the 2-N position of glucosamine, giving rise to a positively charged ammonium group, effectively cancels any inhibitory effect, as evidenced by the fact that all of the test compounds, H-9017, H-8892, and H-9142, were "neutral." The presence of one or two sulfate groups at the 2-position of the iduronic acid or the 6-position of the glucosamine had no apparent effect.

Finally, the presence of an acetyl group at $X_3$ combined with the absence of sulfate groups at $X_1$ and $X_2$ give rise to an augmenting regulatory activity (H-0895).

One should note the strong correlation between the negative charges present in the disaccharide and its ability to inhibit the production of TNF-α. The presence of the positively charged ammonium substituent gives rise to "neutral-ity," whereas the charge-neutral compound H-0895 augments the production of active TNF-α.

TABLE XXIIIB

Empirical Rules Gleaned From the Results of In Vivo DTH Studies Involving Commercially Available Disaccharides.

| Identity Of $X_n$ in H-GENUS | | | Observed |
|---|---|---|---|
| $X_3$ | $X_2$ | $X_1$ | Activity |
| $SO^3$ | $SO^3$ | $SO^3$ | Inhibition |
| $SO^3$ | $SO^3$ | H | Inhibition |
| $SO^3$ | H | $SO^3$ | Inhibition |
| $SO^3$ | H | H | Neutral |
| $COCH_3$ | $SO^3$ | $SO^3$ | Inhibition |
| $COCH_3$ | $SO^3$ | H | Neutral |
| $COCH_3$ | H | $SO^3$ | Neutral |
| $COCH_3$ | H | H | Augmentor |
| $H^{2+}$ | $SO^3$ | $SO^3$ | Neutral |
| $H^{2+}$ | $SO^3$ | H | Neutral |
| $H^{2+}$ | H | $SO^3$ | Neutral |

6.19.2. Results of the Ability of Selected Monosaccharides to Regulate the In Vivo Production of Active TNF-α.

Additional experiments were performed in which selected monosaccharides, commercially available from Sigma, were tested for their ability to regulate the in Vivo production of active TNF-α. Using substantially the same procedure described in the preceding Section, CD1 mice, 6 to a group, were inoculated and treated with a variety of control and test substances to determine the effect, if any, of the subcutaneously injected substances on the experimental DTH reaction of the test animals. The results of these experiments are presented in the Table below.

TABLE XXIIIC

Additional In Vivo Results Using a Variety of Monosaccharides Administered Subcutaneously

| Test material $(\mu g/gm)^{-1}$ | Dose $(\mu g/gm)$ | DTH $(10^{-2}$ mm) | $Inh_{max}$ (%) | "R" value % x |
|---|---|---|---|---|
| GlcN[a] | 0.000012 | 5 ± 0.7 (19.7 ± 1.2) | 75 | 6.25 × 10⁶ |
| | 0.4 | 2.3 ± 0.9 (19.7 ± 1.2) | 88 | 2.2 × 10² |
| GlcN-2S[b] | N.E. | | | 0 |
| GlcN-3S[c] | N.E. | | | 0 |
| GlcN-6S[d] | N.E. | | | 0 |
| GlcN-2, 3S[e] | 0.0012 | 6.3 ± 1 (19.7 ± 1.2) | 68 | 5.67 × 10⁴ |
| GlcN-2, 6S[f] | 1.2 | 7.7 ± 1 (19.7 ± 1.2) | 61 | 5.08 × 10 |
| NAc-GlcN[g] | N.E. | | | 0 |
| GalN[h] | 0.00004 | 8.9 ± 0.6 (18.9 ± 0.7) | 50 | 1.25 × 10⁶ |
| | 0.12 | 6.5 ± 0.7 (18.9 ± 0.7) | 67 | 5.58 × 10² |

[a]GlcN is glucosamine or 2-amino-2-deoxy-D-glucose. Two effective dose ranges were observed for inhibition ≧50% of control: 0.000004-0.00004 μg/gm and 0.004-4 μg/gm.

[b]GlcN-2S is D-Glucosamine-2-N-sulfate. "N.E." indicates that no effect was observed at the tested dosage range of 0.000004-4 μg/gm mouse.

[c]GlcN-3S is D-Glucosamine-3-sulfate.

[d]GlcN-6S is D-Glucosamine-6-sulfate.

[e]GlcN-2,3S is D-Glucosamine-2,3-disulfate. The effective dose range for inhibition ≧50% of control was narrow.

[f]GlcN-2,6S is D-Glucosamine-2,6-disulfate. The effective dose range for inhibition ≧50% of control was narrow.

[g]NAc-GlcN is N-Acetylglucosamine.

[h]GalN is D-Galactosamine. Two effective dose ranges were observed for inhibition ≧50% of control: 0.00004-0.00012 µg/gm and 0.04-0.4 µg/gm.

The stereochemistry of the hydroxyl at the 4-position of the monosaccharide determines whether the sugar is glucosamine (α-face) or galactosamine (β-face), as indicated, below.

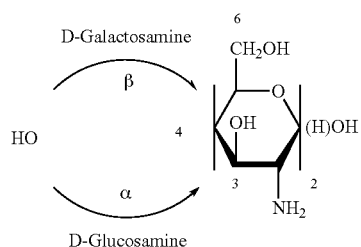

It thus appears that N-acetylation or the presence of one sulfate in the monosaccharide interferes with the ability of glucosamine to inhibit the DTH reaction in mice.

6.19.3. Treatment of Adjuvant Arthritis (AA) in Rats With Selected Monosaccharides and Disaccharides AA was induced in female Lewis rats, 6-8 weeks old, as described in Section 5.7, above. Groups of rats, 5-10 rats per group, were treated with a test substance by subcutaneous injection 1 day before induction of the experimental arthritis and subjected to repeat treatments weekly thereafter. The effects, if any, were scored as described in Section 5.7.

Figure 38:
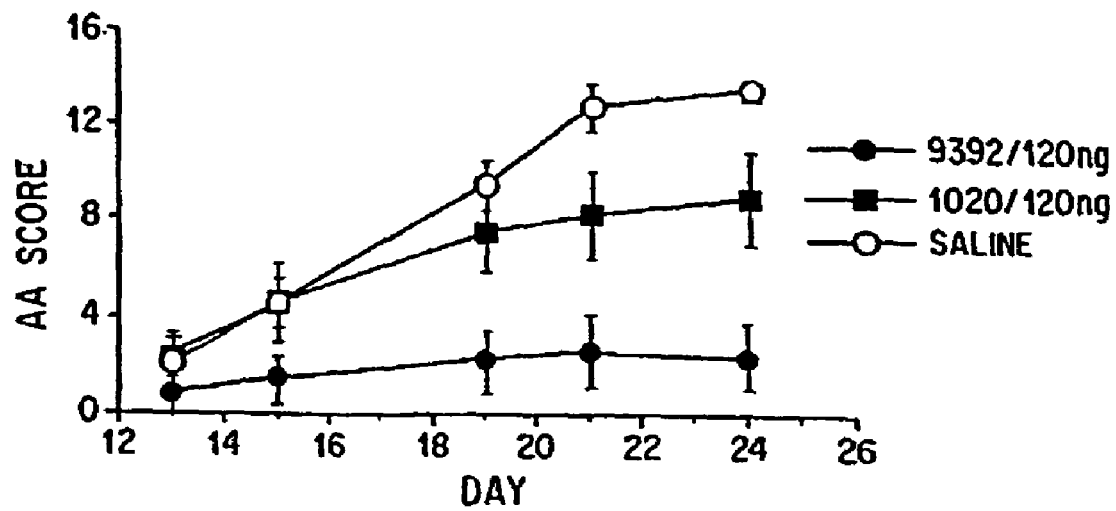
FIG. 38 illustrates the results of experiments comparing the effectiveness of disaccharide 9392 and 1020 to improve the AA scores of female Lewis rats suffering from experimentally induced adjuvant arthritis.
Figure 38A:
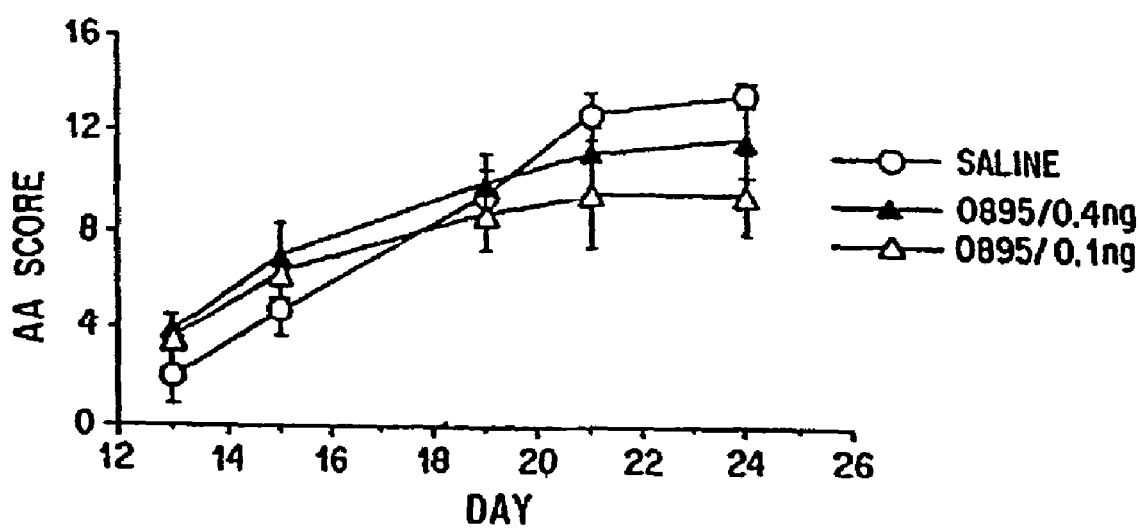
FIG. 38A illustrates the effect of disaccharide 0895 on the AA scores of rats suffering from experimentally induced AA relative to control (PBS).

Of the three disaccharides tested, H-9392 showed the most pronounced effect in lowering the AA score relative to control groups of rats which received only saline (0.1 ml). As illustrated in FIG. 38, H-9392, administered at 120 ng/rat or 0.6 ng/gm rat, suppressed the destructive inflammation of AA almost completely (up to about 90%) 24 days after induction and H-1020 inhibited the development of AA by about 30% relative to control at day 24. In contrast, the augmentor, H-0895, showed an increased level of AA development within about 2 weeks of induction at 2 dosage levels: 0.1 and 0.4 ng/rat. This effect, however, faded rapidly after that until, at day 24, the AA score was not substantially different from control levels (See, FIG. 38A.)

Figure 38B:
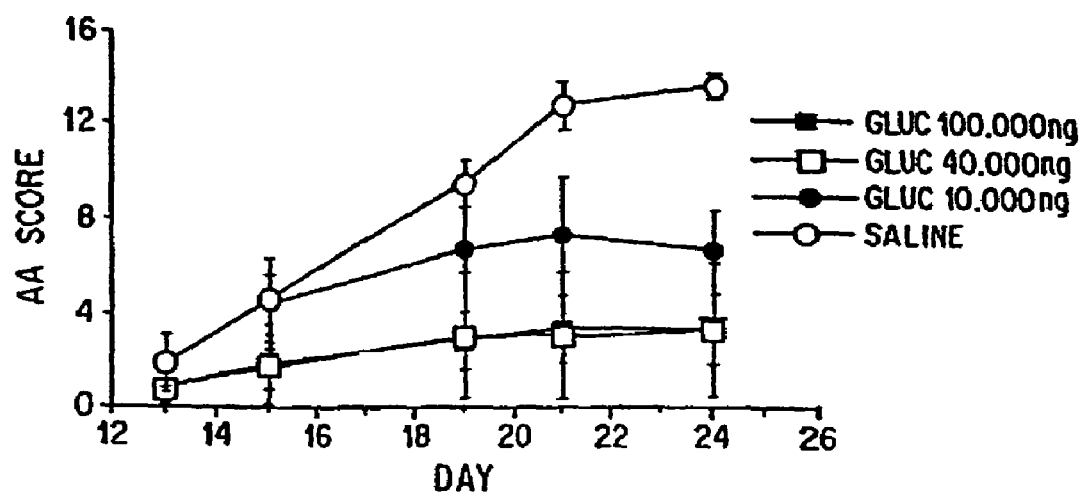
FIG. 38B illustrates the effects of glucosamine treatment in the improvement of the AA score of Lewis rats under various dosages of glucosamine.
Figure 38C:
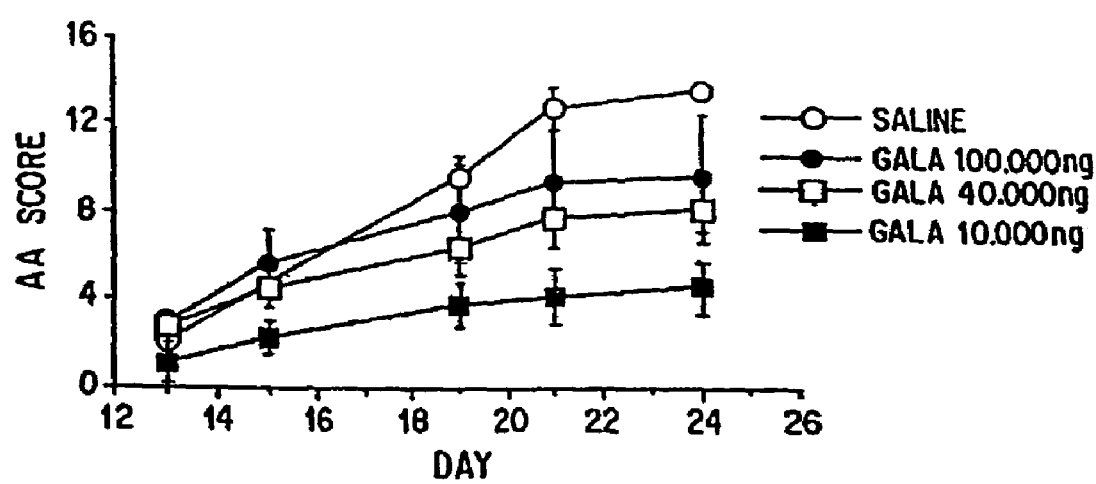
FIG. 38C, similarly, shows the effect of galactosamine at different dosages on the AA score of Lewis rats.

On the other hand, certain monosaccharides were also found to exhibit in vivo einhibitory effects in this rat model. As shown in FIG. 38B, glucosamine treatment at three dosage levels inhibits the development of AA by about 60-80% of control levels. Galactosamine also exhibits inhibitory effects but to a much lesser degree than that shown by glucosamine. (See, FIG. 38C.)

Figure 38D:
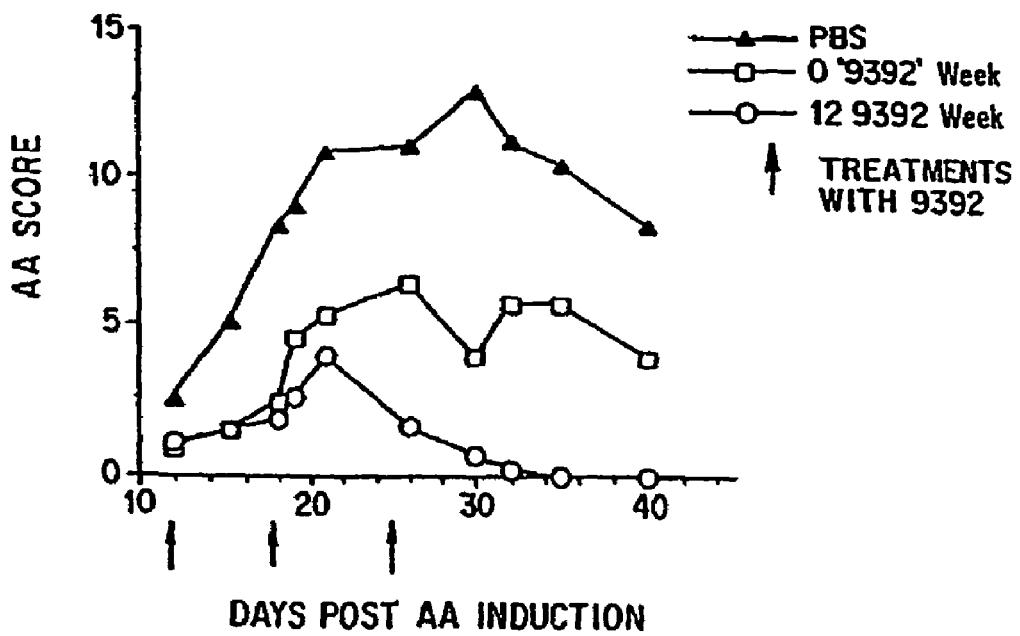
FIGS. 38D and 38E illustrate the results of further experiments carried out with disaccharide 9392 in which the disaccharide is administered either weekly or daily beginning at day zero (i.e., start of induction of AA) or at day 12 (i.e., when the rat is already suffering from AA).
Figure 38E:
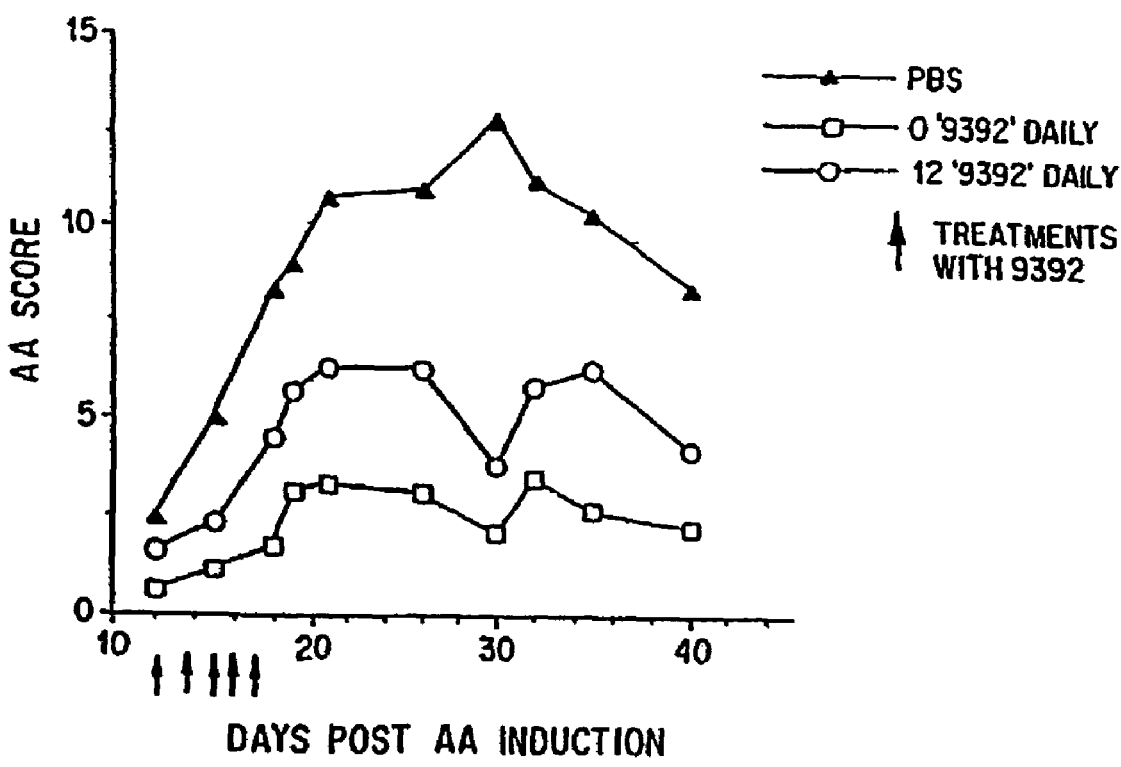

Most interestingly, further experiments carried out with H-9392, in which the disaccharide was administered either weekly or daily beginning at day 0 (start of induction of AA) or at day 12 (the rat is already suffering from AA), showed positive suppression of the severity of AA in all cases. The results of these experiments are presented in FIGS. 38D (weekly) and 38E (daily). As indicated in FIG. 38D, weekly administration of H-9392 beginning at day 12, that is, even after the rat is already afflicted with AA, is at least as effective as weekly treatment at the start of induction (day 0) relative to control. FIG. 38E shows that while daily treatment of afflicted rats was not as effective as daily treatment beginning at the start of induction, the daily treatment of rats with established arthritis was still highly effective at lowering the score of the AA relative to the control group.

These results show dramatically that the substances of the present invention are effective not only not only in preventing the development of severe arthritis but are also effective in treating established arthritis. Furthermore, the present work also demonstrates that while the LMWHs described previously show inhibitory characteristics only when administered weekly, the disaccharides of the present invention are able to manifest useful inhibitory activity when administered weekly or daily.

As a further illustration of the superiority of the compounds of the present invention in the treatment of experimentally induced AA, a separate, comparative set of experiments was carried out in which groups of Lewis rats (5 rats per group) were treated by subcutaneous injection with either dexamethasone phosphate (purchased from Sigma, a known antiinflammatory agent) or the disaccharide 9392. Treatments were begun 12 days after induction of the adjuvant arthritis (AA) disease and consisted of two treatment regimens: the first involving daily injection of the known antiinflammatory agent; the second involving weekly injection of the known antiinflammatory agent or the disaccharide. In all cases, 100 µg of the known antiinflammatory agent in 0.1 ml of phosphate buffer solution was administered to each rat, while 120 ng of the disaccharide, also in 0.1 ml of phosphate buffer solution, was administered per rat. As a control, a group of rats was injected with 0.1 ml of phosphate buffer solution only. For the daily dose regimen of known antiinflammatory agents, treatments were ended after day 17 post-induction and for the weekly dosage regimen of known antiinflammatory agent or is disaccharide, the treatments were ended after day 26 post-induction.

Figure 38F:
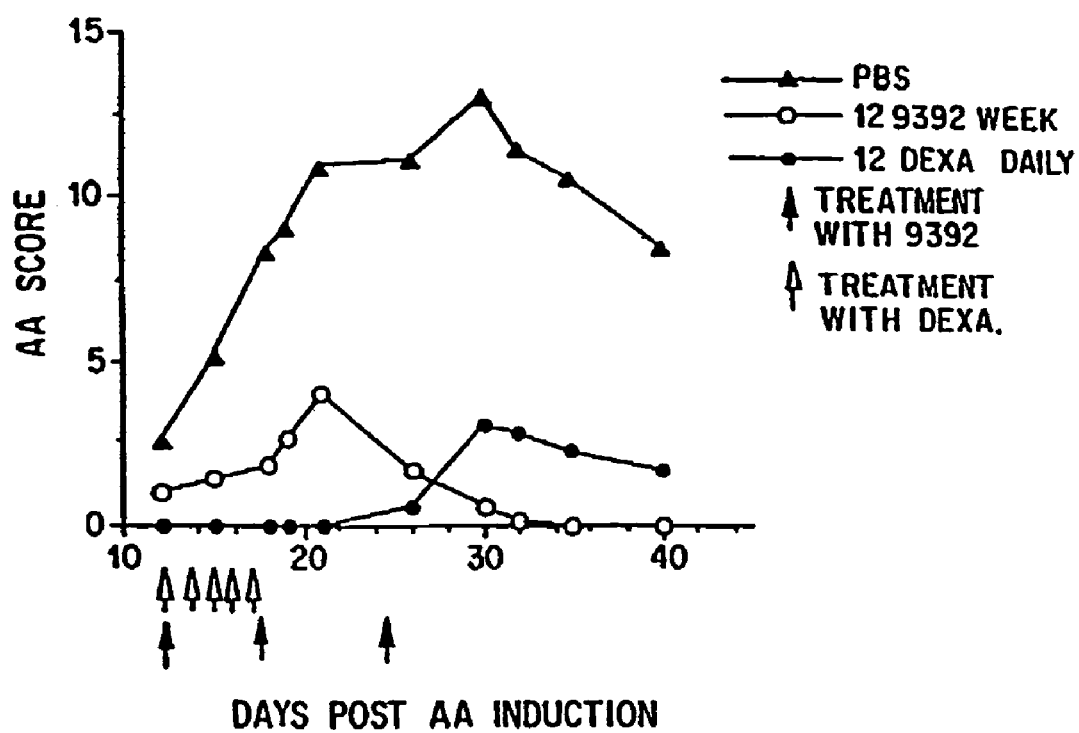
FIGS. 38F and 38G illustrate the results of a separate comparative set of experiments that were carried out on groups of Lewis rats to determine the effectiveness of disaccharide 9392 administered weekly compared with the effectiveness of a known anti-inflammatory agent, dexamethasone phosphate, on the suppression of experimentally induced adjuvant arthritis.
Figure 38G:
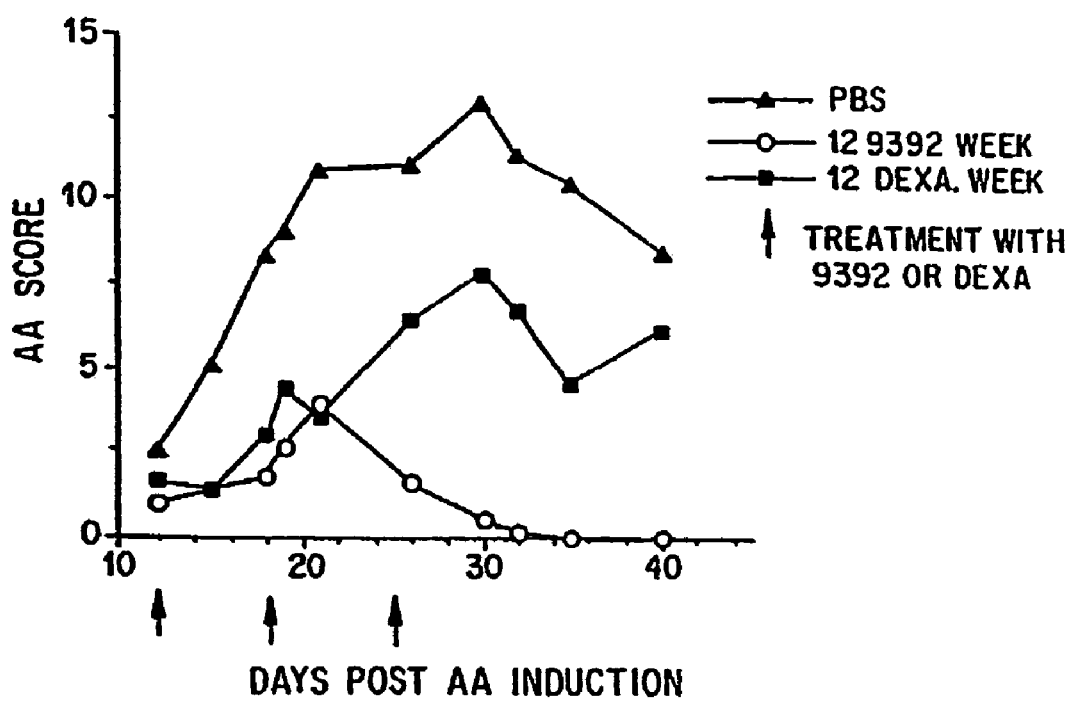

The results of the above experiments are illustrated in FIGS. 38F and 38G. Upon examination of FIG. 38F, one sees that the weekly administration of the disacchariide 9392 compares well with the daily administration of dexamethasone phosphate during about the first week of treatment. Note, however, that after treatment has ended (after day 26), the group of rats that received daily dexamethasone phosphate suffered a relapse while the disaccharide group continued to improve. At 30 days post-induction of AA, the disaccharide group fared better than the dexamethasone phosphate group.

What is more, comparing the effectiveness of weekly dexamethasone phosphate vs. weekly disaccharide 9392, as illustrated in FIG. 38G, one sees that at 30 days post-induction of the AA, weekly administration of dexamethasone phosphate resulted in only a moderate reduction in the severity of the AA score. In contrast, the weekly administration of disaccharide 9392 at 30 days post-induction of the AA gave rise to an almost complete suppression of the experimentally-induced adjuvant arthritis. Again, of particular note, after weekly treatment was ended for the dexamethasone phosphate, the rat suffered a relapse of the adjuvant arthritis. As noted previously, the rats treated with the disaccharide 9392, however, continued to improve even after administration of the disaccharide had ceased.

Thus, the weekly administration of the disaccharide 9392 is manifestly superior over the daily or weekly administration of dexamethasone phosphate over the long term. Whereas the rats treated with dexamethasone phosphate, either daily or weekly, suffered a relapse of the disease after treatment was ended, the rats treated with the disaccharide continued to exhibit improved AA scores, reflecting a continued post-treatment inhibition of the disease.

6.19.4. Results of Experiments Relating to the Lipopolysaccharide (LPS)-Induced Inflammation of the Rat Cornea.

LPS-induced inflammation of the cornea is TNF dependent, as shown by the work of Vanderhagen, C. and co-workers in the Netherlands, "Kinetics of Intraocular TNF and IL-6 in Endotoxin-Induced Uveitis in the Rat," submitted for publication. Using a 30-gauge needle, LPS (5 ng) was injected into the cornea of Lewis rats. After one day, separate groups of rats, 2 to a group (or 4 eyes to a group) were then injected subcutaneously with phosphate-buffered saline (0.05 ml) or H-1020 (at a dose of either 50 ng/rat or 200 ng/rat). The effects, if any, were scored as follows:

| | |
|---|---|
| edema | 0-3 points |
| neovascularization | 0-3 points |
| redness | 1/0 points |
| swelling | 1/0 points |
| hemorrhage | 1/0 points |
| miosis | 1/0 points |
| synaechi | 1/0 points (iris adherent to lens or cornea) |
| hypopyon | 1/0 points (pus or blood in anterior chamber) |
| hazy cornea | 1/0 points | in which the sum of the points is used as the total score.

Figure 39:
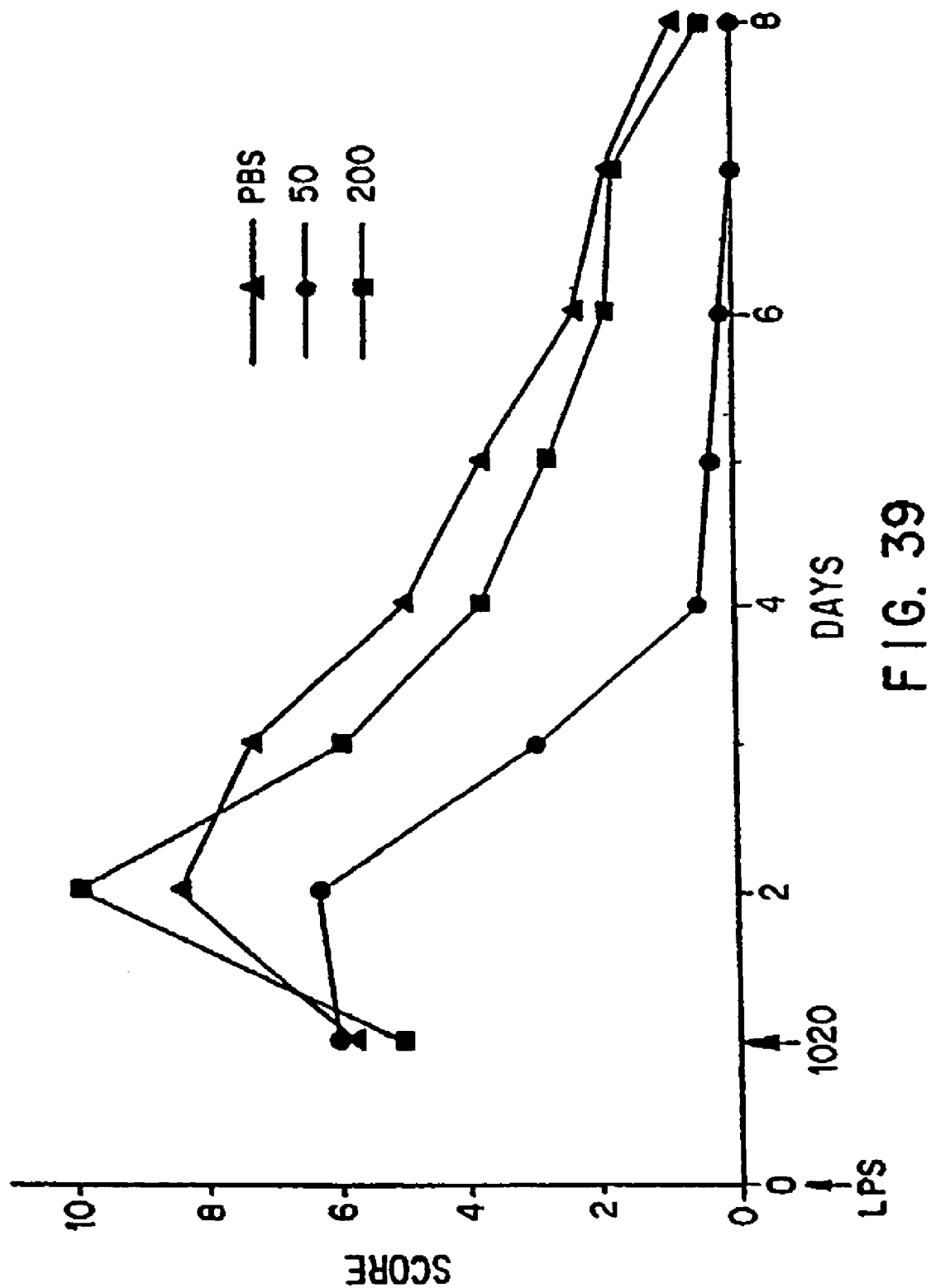
FIG. 39 illustrates the effectiveness of subcutaneously injected disaccharide 1020 against liposaccharide (LPS) induced inflammation of rat corneas.
Figure 39A:
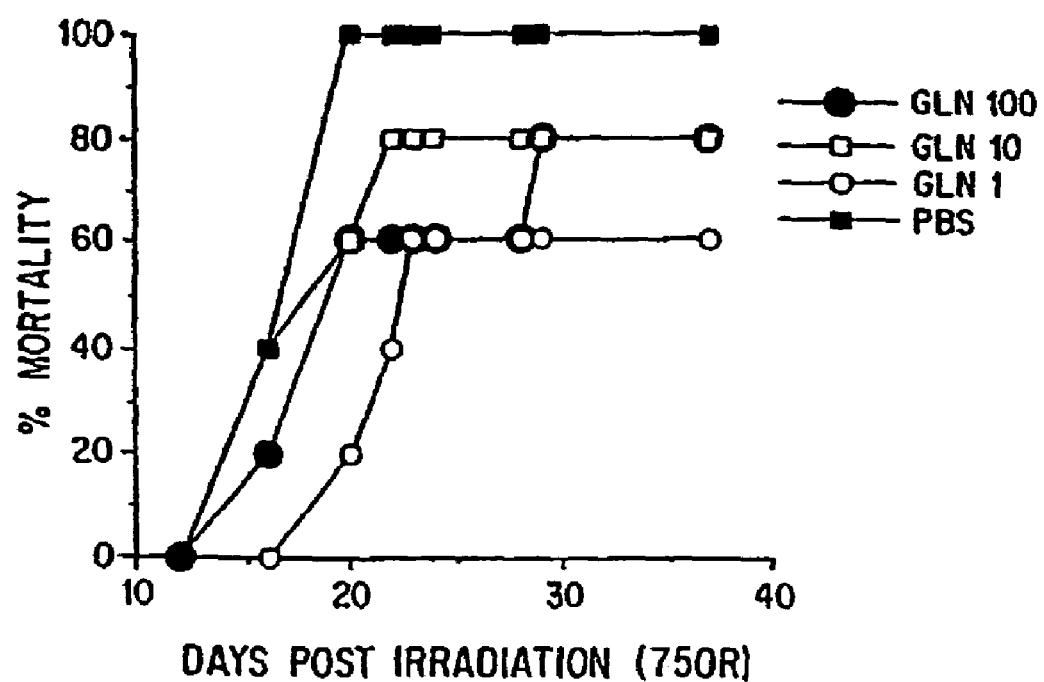
FIG. 39A presents the results of experiments relating to the radioprotective effects of glucosamine at various dosages relative to control (PBS).
Figure 39B:
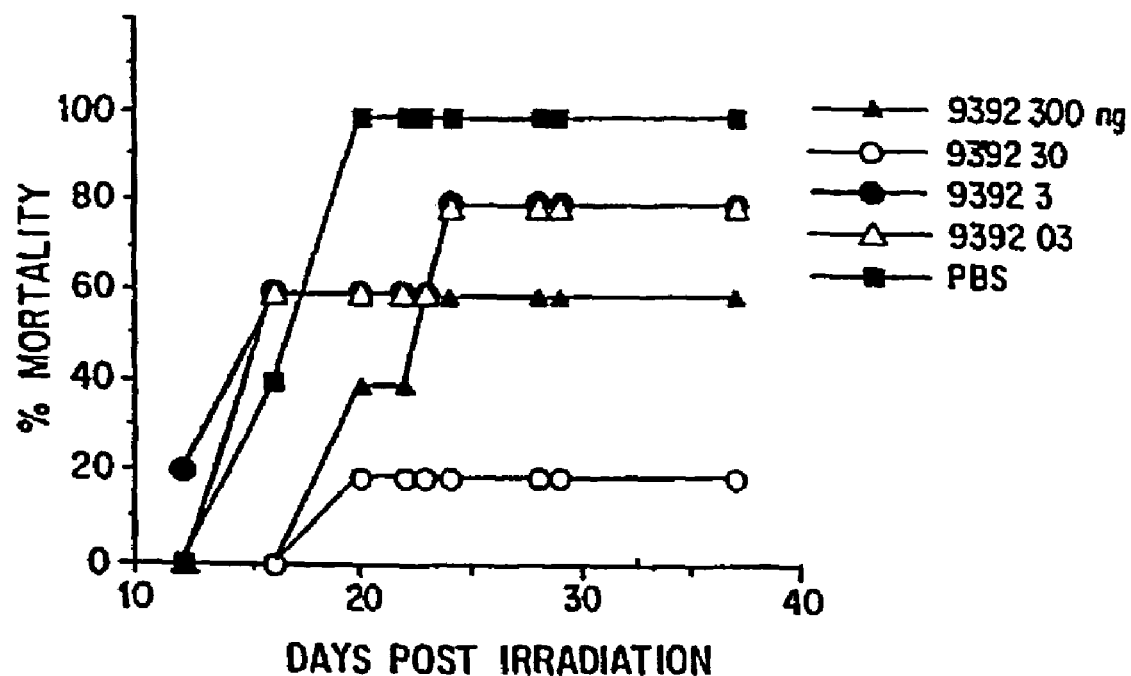
FIG. 39B presents the results of similar irradiation experiments involving the administration of disaccharide 9392 at various dosages relative to control (PBS).

As can be seen from the graphical representation of the results (FIG. 39), the 50 ng/rat dose was effective to suppress the effects of the local LPS-induced inflammation relative to control. Interestingly, a dose of 200 ng/rat failed to provide a significant effect.

6.19.5. Results of Experiments Relating to the Lipopolysaccharide (LPS)-Induced Uveitis in Rats.

Uveitis is the inflammation of the anterior chamber of the eye in response to LPS given systemically. Like the inflammation produced in the preceding Section by the local administration of LPS, uveitis is TNF-dependent. In the present experiment, groups of Lewis rats, 8 to 10 weeks old, 8 eyes per group, were treated at Day 1 with either H-9392 (at a dose of 32 ng/rat or 500 ng/rat) or saline (0.1 ml). At Day 2, a 2 mg/ml solution of LPS (50 µl) was injected into each foot pad; each rat received a total of 200 µg LPS. At Day 3, each eye was tapped and the concentration of total protein was measured as a quantitative assay of the degree of inflammation. The results of these experiments are provided immediately below.

| Rats | Treatment | Median Protein (mg/ml) |
|---|---|---|
| No LPS | — | 0.36 |
| LPS | Saline | 18.4 |
| LPS | 32 ng H-9392 | 5.2 |
| LPS | 500 ng H-9392 | 4.8 |

Hence, a single administration of H-9392, at either dosage, was effective to suppress the inflammation produced by the systemic administration of LPS in the rat by over about 70% relative to control.

6.19.6. Results of Experiments Relating to the Radioprotective Effects of Selected Substances Groups of female BALB/c mice, 8 weeks old, 5-10 mice per group, were injected subcutaneously with either saline (0.1 ml, control), H-9392 (30 ng/mouse), or glucosamine (10,000 ng/mouse) 1 day before irradiation, and weekly thereafter until termination of the experiment on day 30. All the mice were irradiated to a dose of 700 rads using a $^{60}$Co gamma radiation source.

The mortality within the different groups of mice was then scored over a 30 day period. The results showed that the mice that received only saline suffered a 100% mortality rate by day 30, whereas the mice that had been pretreated with H-9392, showed only a 40% death rate in the same period. The group of mice which had been injected with glucosamine also fared better than the control group, showing a 20% mortality rate in the same period.

Thus, pretreatment with the test substances of the present invention, allowed the pretreated mice to survive a radiation regimen that would have ordinarily resulted in a 100% mortality rate for the group within 30 days.

In a separate experiment, groups of BALB/c mice (5 mice to a group) were likewise exposed to 750 rads of gamma-rays, except that these groups of mice were treated with test substances (saline at 0.1 ml per mouse; H-9392 at 0.3, 3, 30 and 300 ng/mouse; and glucosamine at 1, 10 and 100 µg/mouse) on the day before irradiation, on the sixth day after irradiation, and once again on the thirteenth day after irradiation only. All treatment ceased after the third and last administration. The results of this experiment are illustrated in FIGS. 39X (saline and glucosamine) and 39Y (saline and H-9392) and indicate that while all the animals in the control group had died by the twenty-second day after irradiation, only one mouse in the 30 ng H-9392 group had died by the thirtieth day after irradiation. The 300 ng H-9392 and the 1 µg glucosamine treatment regimens showed moderate activity in suppressing mortality after irradiation.

These results thus indicate a possible utility of the substances of interest in cancer therapy in which the toxicity associated with radiation treatment may be reduced dramatically by proadministration of the instant compounds. This approach may, perhaps, allow an increase in the dosage of the radiation to higher more effective levels without observing toxic side effects. As illustrated by the experiments described above, the compounds of the present invention are highly effective at certain very low dosages even when treatment is limited to three administrations of disaccharide.

6.19.7. The Ability of Selected Substances to Suppress Allograft Rejection

Figure 40:
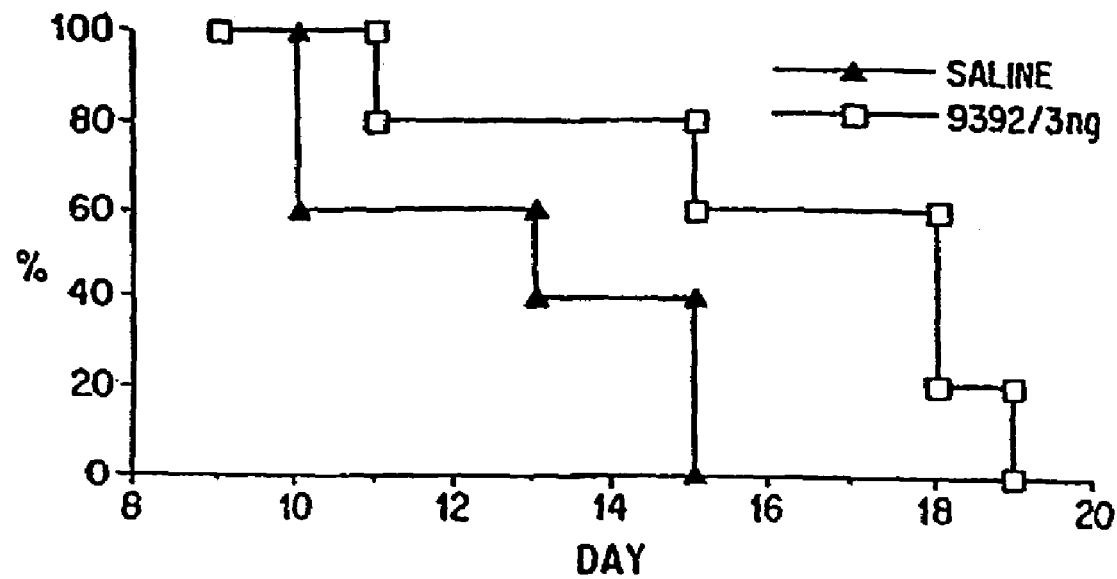
FIGS. 40 and 40A illustrate the results of experiments that illustrate the ability of selected substances of the present invention to suppress allograft rejection. The results presented in FIG. 40 show that a 3nanogram dose of disaccharide 9392 by subcutaneous injection one day before grafting and weekly thereafter, delayed the level of skin graft rejection at 50% by 5 days. However, a 300 nanogram dose of the same disaccharide failed to produce a significant difference at 50% rejection relative to control (PBS).
Figure 40A:
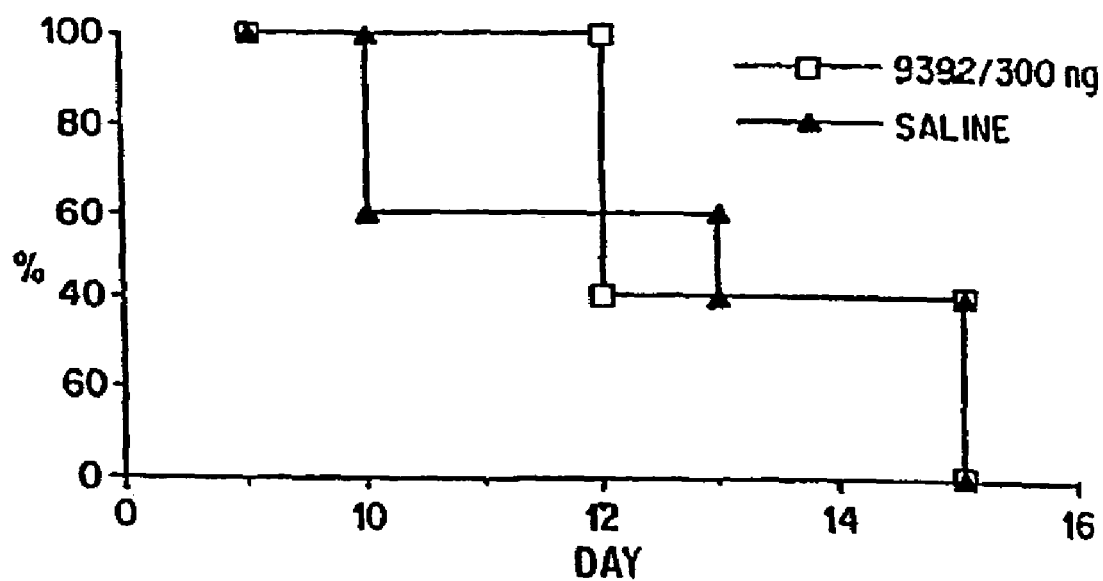

The effect of H-9392 was also tested in skin graft rejection experiments in mice. In particular, skin grafts from C57BL/6 donor mice (H-2$^b$) were applied to recipient BALB/c mice (H-2$^d$) according to the method of Baharav, E. et al. *J. Immunol. Methods* (1986) 90:143-144. The number of days to rejection was measured by the sloughing of the graft. The number of days to rejection was determined for a control group (injected with saline only, 0.1 ml), and test groups that received 3 ng or 300 ng of H-9392 by subcutaneous injection one day before grafting and weekly thereafter. The results, which are graphically represented in FIGS. 40 and 40A, reveal that the 3 ng/mouse dose delayed the level of skin graft rejection at 50% by 5 days! However, the same compound, administered at 300 ng/mouse failed to produce a significant difference at 50% rejection relative to control. These results are very significant given that rejection of a fully allogeneic skin graft is recognized to be one of the most powerful immune responses known.

6.19.8. The Ability of Selected Substances to Suppress the Development of IDDM in NOD Mice It is well known that NOD mice serve as a faithful model of human diabetes Type I. Indeed, all female NOD mice in our colony develop diabetes spontaneously within about 4-5 months of age. Because Type I diabetes or insulin-dependent diabetes mellitus (IDDM) is recognized as an autoimmune disease that may be precipitated by autoreactive T cells, selected compounds of the present invention were tested for their ability to regulate this T cell-mediated autoimmune reaction.

Figure 41:
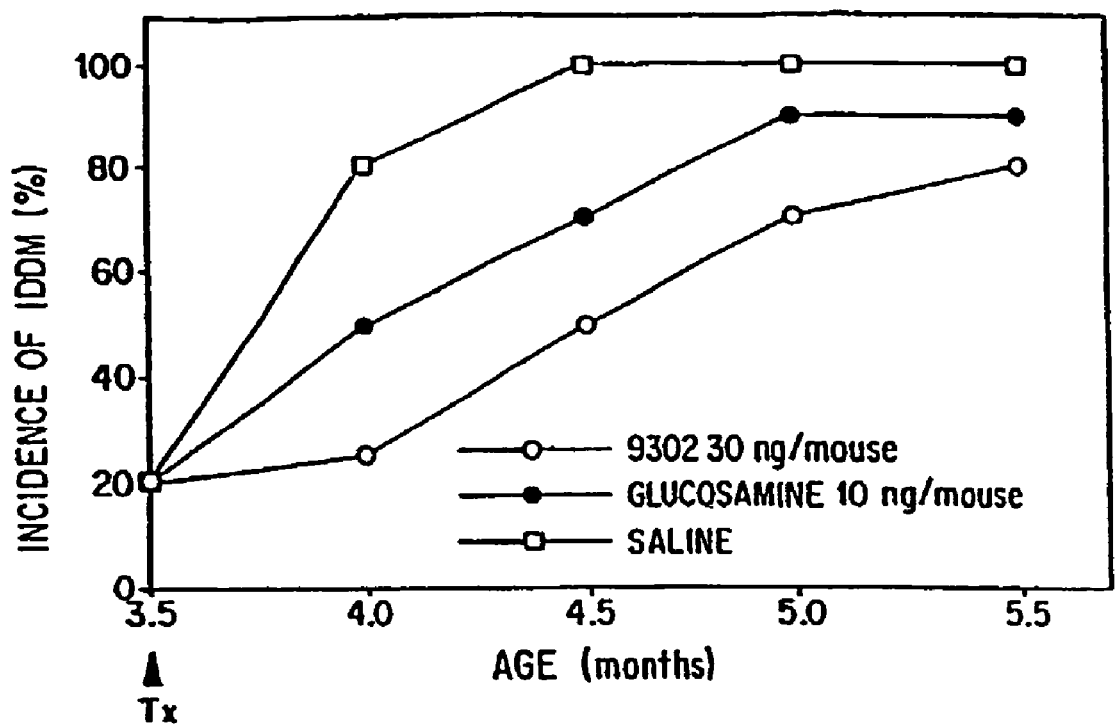
FIG. 41 illustrates the incidence of IDDM in groups of female NOD mice which had been separately treated with either disaccharide 9392, glucosamine or saline.

Hence, groups of female NOD mice, 6-12 to a group, were treated by subcutaneous injection with saline (0.1 ml), H-9392 (30 ng/mouse), or glucosamine (10,000 ng/mouse). All the mice were about 3.5 months old, as shown in FIG. 41, meaning that the mice as a group already endured a 20% incidence of IDDM. The incidence of IDDM can be monitored by the level of glucose in the blood of the mice. Non-diabetic mice exhibit a mean glucose level in the blood of about 140±10 mg/ml. A mouse is considered a diabetic if its blood glucose level is equal to or exceeds 200 mg/ml (i.e., is greater than about three times the standard deviation of the "normal" level). For greater convenience, glucose urine levels were measured using the Clinstix™ dipstick (Ames). This test provides scores of 0 to +3, with a score of +2 or greater on two separate occasions taken as a positive indication of diabetes.

It was thus very surprising to discover that both the H-9392 and glucosamine inhibited the onset of diabetes in NOD mice such that at 4.5 months, when all the control mice were considered diabetic, only about 65% of the glucosamine-treated mice had become diabetic, while among the H-9392-treated mice, less than 50% were afflicted with the disease.

Figure 41A:
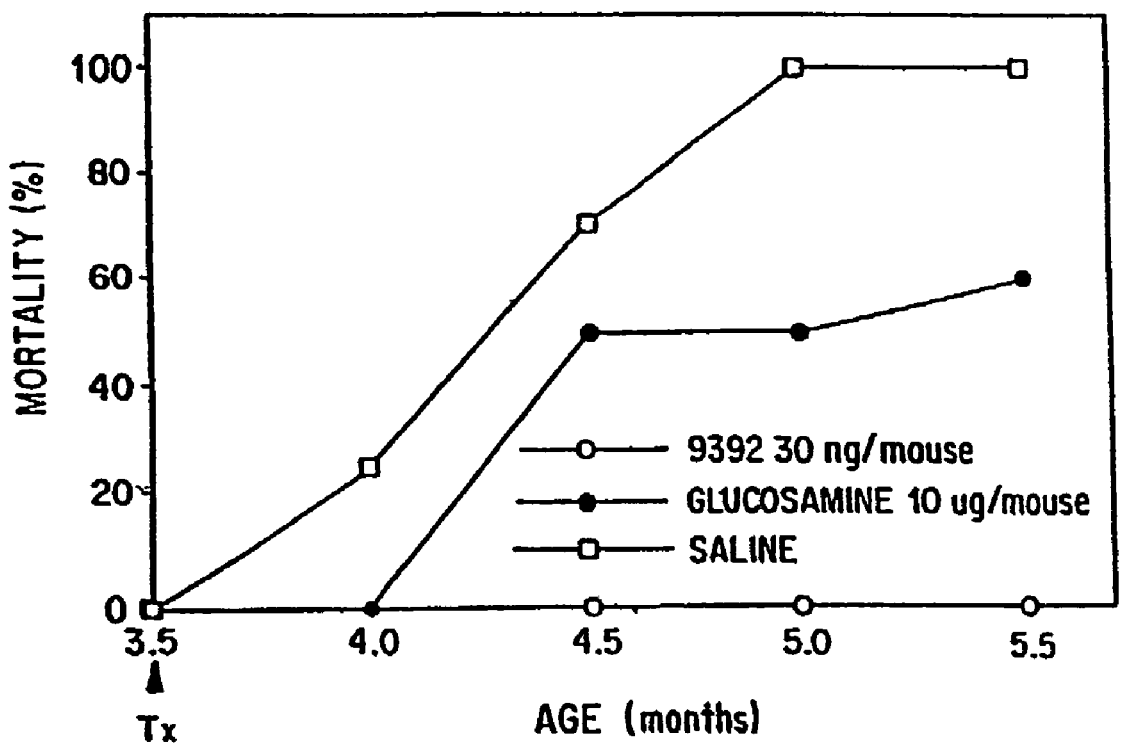
FIG. 41A presents the mortality rate of female NOD mice that, again, had been treated separately with the disaccharide 9392, glucosamine, or saline. It should be noted that in both FIGS. 41 and 41A, the female NOD mice were approximately 3½ months old, meaning that the mice as a group already endured a 20% incidence of IDDM.

Put another way, FIG. 41A shows that by age 5 months, all the control mice had died from their diabetic condition. In contrast, only about half of the mice treated with 10,000 ng of glucosamine had died within the same time frame. Quite strikingly, none of the mice treated with 30 ng of H-9392 died within the same time frame; that is, the plot for the H-9392 results is coincident with the x-axis.

6.19.9. Effect of Selected Disaccharides on TNF-α-Induced Expression of Adhesion Molecules, XCAM-1 and ELAM-1, by Endothelial Cells (EC).

The adhesion molecules, such as ICAM-1 and ELAM-1, are critical in the recognition and subsequent "rolling" (i.e., adherence to endothelium and migration through the endothelium) of leukocytes involved in the inflammatory response. In response to active TNF-α, endothelial cells (EC) express ICAM-1 and ELAM-1. Thus, TNF-α can augment inflammation by up regulating the signals for leukocyte adherence and migration. To determine the effect of the disaccharides of the present invention on the TNF-α-induced expression by EC of ICAM-1 and ELAM-1, the following experiment was carried out.

Freshly isolated human umbilical vein EC were grown in M-199 (Gibco Laboratories) supplemented with 10% FCS, 8% human serum, antibiotics and 50 µg per ml endothelial cell growth factor (EC-GM; Sigma, St. Louis, Mo.). The EC were seeded by adding 0.1 ml of the EC-GM medium ($3.5 \times 10^5$ cells per ml.) to flat-bottom 96-well plates (Nunk Roskilde, Denmark).

Confluent monolayer cultures were washed and incubated with selected disaccharide compounds at various concentrations in 50 µl of M-199 at 37° C. for 1 h. The compounds were then washed away, and the cultures were incubated over-night with preformed TNF-α, 200 IU per ml, in EC-GM. The cells were then washed three times at 37° C. with Hank's solution containing 1% FCS (Hank's 1%), and fixed with 2% glutaraldehyde in PBS. The cells were then washed three times with Hank's 1%, blocked with 2.5% BSA in PBS, and rewashed twice with Hank's 1%. Anti-ICAM-1 and ELAM-1 mAb (Genzyme, Cambridge Mass.; diluted 1/1000 in PBS) were incubated with the cells for 1 h at 22° C. and, then, washed off three times with Hank's 1%. Peroxidase-conjugated goat anti-mouse Ab sigma, diluted 1/1000) was incubated with cells for 1 h and, subsequently, washed off. After adding the o-Phenylenediamine (OPD) prepared by dissolving an OPD hydrochloride tablet in water (OPD is a substrate for peroxidase and can be obtained from Sigma, Cat. No. p9187), the absorbance was detected in an ELISA reader at 492 nm. Samples were assayed in triplicate, and the average of at least three different assays were calculated.

TABLE XXIIID

Effect of Disaccharides on the Expression of Adhesion Molecules by Endothelial Cells in Response to Preformed TNF-α.

| TNFα treatment of EC | Inhibitory compound [pg/ml] | Recombinant human TNFα-induced adhesion molecules (O.D 492)*: | |
|---|---|---|---|
| None | None | 0.12 ± 0.01 | 0.18 ± 0.01 |
| Yes | None | 1.2 ± 0.1 | 2.2 ± 0.2 |
| Yes | 9392 [50] | 0.6 ± 0.1 | 1.0 ± 0.04 |
| Yes | 9392 [100] | 0.9 ± 0.07 | 1.4 ± 0.03 |
| Yes | 1020 [50] | 0.7 ± 0.05 | 1.2 ± 0.1 |
| Yes | 1020 (100] | 0.9 ± 0.03 | 1.5 ± 0.07 |

*Expression of ELAM-1 and ICAM-1 detected by ELISA binding of specific monoclonal antibodies The experiments described above demonstrate that pretreatment of EC with disaccharide compounds 9392 and 1020 endows the EC with significant resistance to preformed TNF-α. Hence, the up regulation of EC expression of adhesion molecules induced by TNF-α was inhibited by up to 50%. These results mean that the compounds of the invention can influence the target cells of TNF-α (e.g., EC), as well as the cells that produce TNF-α (e.g., T cells, macrophages) to inhibit not only the production of active TNF-α but also the propensity of the target cells to respond to TNF-α (i.e., regulation of peripheral reception of the cytokine). Certain disease states, then, may benefit from the administration of the substances of the present invention by imparting on the target cells of TNF-α a type of resistance against the cell-induced inflammatory response initiated by the activated T-cells and macrophages.

6.19.10. The Ability of Substance H-9392 to Suppress the Signs of Experimental Allergic Asthma in Rats Experimental allergic bronchial asthma is an immediate type hypersensitivity reaction in rats which have been immunized and then rechallenged by inhalation of the priming antigen in a aerosolized solution. (Edelman, et al., *Am. Rev. Resp. Dis.* (1988) 137:1033-37). The etiology and pathophysiology of this experimental disease closely parallel the naturally occurring human counterpart.

To assess the ability of substance H-9392 to prevent a bronchial asthma attack, 6 male Brown Norway rats were primed to ovalbumin (OVA) by subcutaneous injection of 1 mg of OVA in suspension with 200 mg AlOH/ml 0.9% saline solution accompanied by intraperitoneal injection of 1 ml solution containing $6 \times 10^6$ heat killed *Bordetella pertussis* bacteria (Pasteur Merieux, S. V.), on day zero. Subsequent challenges consisted of a 5 minute period of inhalation of OVA (1 mg/ml solution) aerosolized in a Devilbiss Nebulizer operated at an airflow of 6 L/min. Respiratory Distress (RD) responses were scored as Grade 0, no signs of distress; Grade 1, tachypnea; Grade 2, moderate labored breathing; Grade 3 severe labored breathing with mouth open; Grade 4, loss of consciousness and muscular tone. Sixteen days following primary immunization all animals were exposed to an initial aerosolized challenge to establish the positive control. The animals were coded so that the observer was ignorant of the subject animal's history. All rats were sensitive to OVA and asthma was uniformly induced in all animals.

Figure 42:
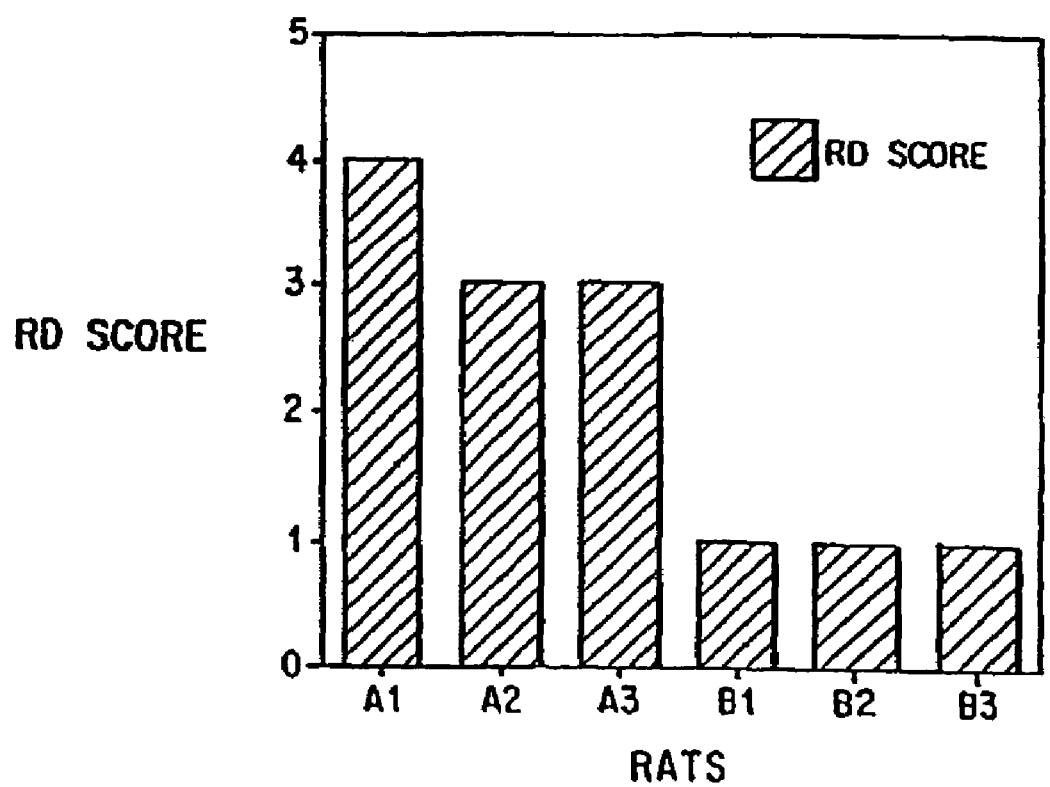
FIG. 42 presents the respiratory distress (RD) score of six immunized rats challenged with aerosolized antigen with (B1, B2 and B3) and without (A1, A2 and A3) treatment by substance H-9392. See text for details.

On day thirty, the animals were divided into 2 groups and given either saline (control Group A) or 30 ng of substance H-9392, s.c., (Group B) and challenged on day 35 as above. The results are presented in FIG. 42. As shown in FIG. 42, the animals which received saline only on day 30 experienced Grade 3 or 4 respiratory distress. The animals treated with substance H-9392 displayed mere tachypnea. The results presented show that administration of substance H-9392 (5 days prior to secondary challenge), to an animal with established hypersensitivity, blocks an asthmatic attack.

6.20. Results of In Vitro Human PBL Bioassay on Commercially Available Neparin Derived Oligosaccharides Commercially available samples of heparin derived disaccharides and polysaccharides ranging in molecular weight from 1,800 and 18,000 were tested for biological activity. The results are presented in Table XXIII. As is evident from the data obtained, all the samples tested, with one exception, gave either no effect or inconsistent effects. As explained in the table footnote, a test result for a particular entry was designated inconsistent if the same qualitative result was not obtained for all three bioassay runs. (Each entry in all the Tables included in this disclosure, which present results of bioassays, was the product of at least three tests. In the human PBL bioassay, each run used blood obtained from different individuals.)

TABLE XXIII

Effect of Commercially Available Heparin Disaccharides on the Secretion of Active TNF Using Human PBL Bioassay.

| Test Material[a] | conc (pg/ml) | Bioassay of TNF Activity (%) | "R" value % × (pg/ml)$^{-1}$ |
|---|---|---|---|
| H 9517 | [b] | Inconsistent[c] | — |
| H 8642 | [b] | Inconsistent | — |
| H 8767 | [b] | Inconsistent | — |
| H 0895 | [b] | Inconsistent | — |
| H 8892 | [b] | No effect | 0 |
| H 9017 | [b] | No effect | 0 |
| H 9142 | [b] | Inconsistent | — |
| H 9267 | [b] | Inconsistent | — |
| H 1020 | 1 | 25% to 35% | 25 to 35 |
| H 9392 | [b] | Inconsistent | — |
| MW 1,800[d] | [e] | Inconsistent | — |
| MW 2,400 | [e] | Inconsistent | — |
| MW 3,000 | [e] | Inconsistent | — |
| MW 3,600 | [e] | Inconsistent | — |
| MW 4,200 | [e] | Inconsistent | — |
| MW 4,800 | [e] | Inconsistent | — |
| MW 5,400 | [e] | No effect | 0 |
| MW 6,000 | [e] | No effect | 0 |
| MW 9,000 | [e] | No effect | 0 |
| MW 16,000 | [e] | Inconsistent | — |
| MW 18,000 | [e] | Inconsistent | — |

[a]Product Number found in Sigma Chemical Co. Product. Catalog (1992).
[b]At a conc range of 1 µg/ml-0.01 pg/ml.
[c]Three bioassays using PBLs obtained from three separate individuals were performed on each test material. A test result for any given test material was designated "inconsistent" if the same result (i.e., inhibition, augmentation, or no effect) was not obtained for all three bioassays.
[d]Molecular weight designations for various Heparin Oligosaccharide Fragments, as described in Serbio Product Catalog (Dec. 26, 1991).
[e]At a conc range of 1 µg/ml-0.01 pg/ml.

6.21. Results of In Vitro Human PBL Bioassay Versus Assay Kit Based on mAb

A comparison of the activity data obtained from the in vitro bioassay based on human PBLs described herein and the results of a conventional monoclonal antibody-based assay kit shows that much more protein is present in the media being tested than what is being detected by the human PBL bioassay as being "active" TNF. The results are presented in Table XXIV. For example, the difference between the amounts of protein produced by T cells in "Control" levels (ca. 274 pg/ml) and when Fragmin HPLC-F16 is present (ca. 200 pg/ml) is not nearly as dramatic as the difference in activity detected by the human PBL assay for the same samples (a 100 percent change in activity). Hence, one may conclude from these results that although the activated immune effector cell may secrete significant amounts of TNF protein, even in the presence of the active substances of the present invention, only a small proportion of the secreted protein is active enough to kill TNF-sensitive cells. This conclusion supports the notion that TNF is produced in both active and inactive forms.

TABLE XXIV

Comparison of TNF Activity Detected by Human PBL Bioassay Versus Amount of Protein Detected by mAb Immunoassay Kit.

| Test Material | Bioassay of TNF Activity (% killed) | | mAb Assay Kit TNF (pg/ml) | |
|---|---|---|---|---|
| None | 45 | Control | 273.9 | Control |
| Fragmin | | | | |
| HPLC-F1 | 72 | Aug$_{max}$ (60%) | 284.5 | Aug$_{max}$ (3.8%) |
| HPLC-F3 | 13.5 | Inh$_{max}$ (70%) | 224 | Inh$_{max}$ (17.9%) |
| HPLC-F16 | 0 | Inh$_{max}$ (100%) | 199 | Inh$_{max}$ (27%) |
| DECM | | | | |
| HPLC-F10 | 18 | Inh$_{max}$ (60%) | 225 | Inh$_{max}$ (17.5%) |
| BPLC-F14 | 13.5 | Inh$_{max}$ (70%) | 232 | Inh$_{max}$ (15%) |
| HPLC-F25 | 63 | Aug$_{max}$ (40%) | 292 | Aug$_{max}$ (6.5%) |
| HPLC-F37 | 90 | Aug$_{max}$ (100%) | 301 | Aug$_{max}$ (10%) |

Figure 24:
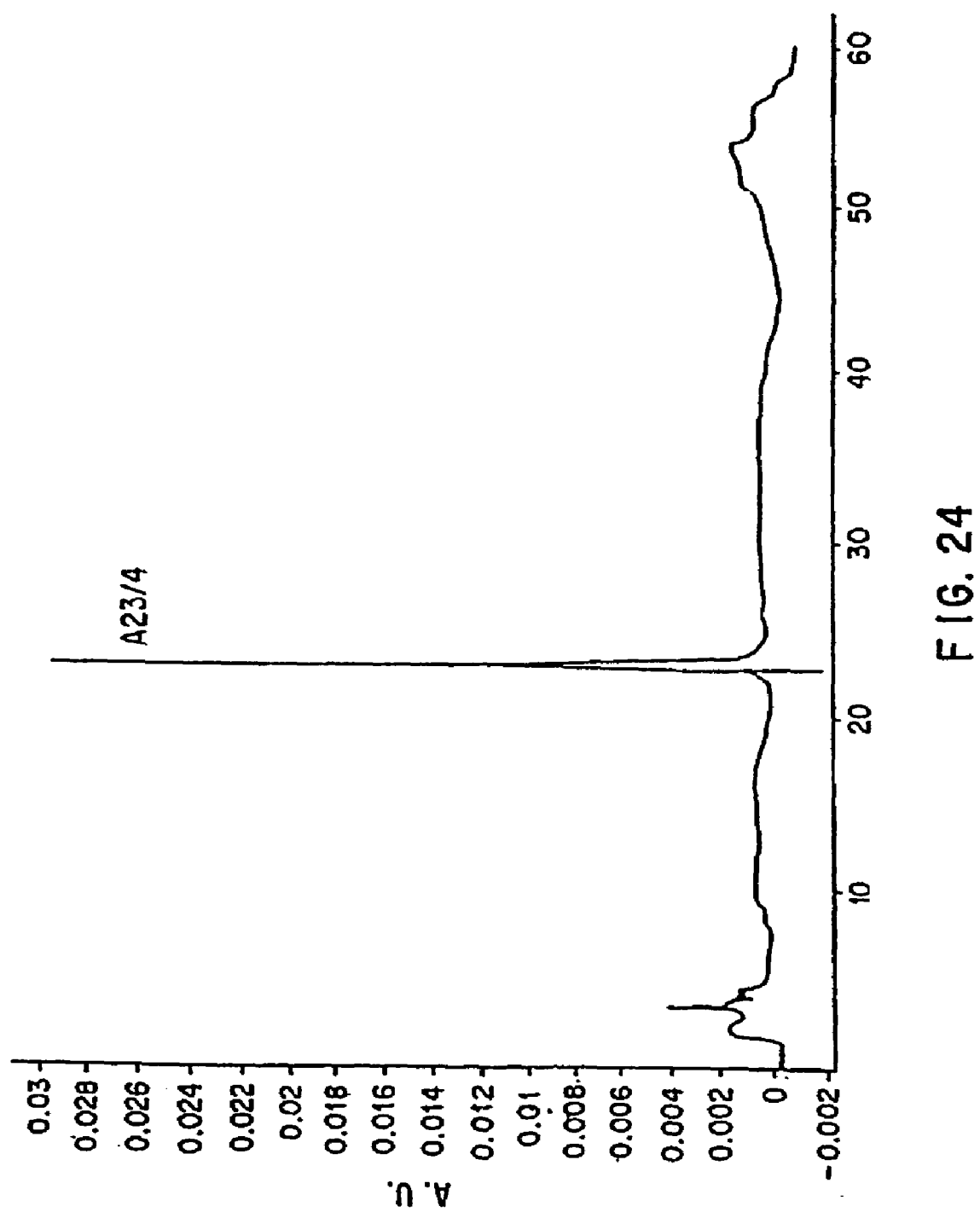
FIG. 24 illustrates another peak labeled "A23/4" obtained from desalted preparations of the peak labeled "1" from FIG. 23.

6.22. Results of Preliminary Investigation of the Structural Characteristics of ECM-Derived Disaccharide A 20 µg sample of an ECM-derived disaccharide was obtained after HPLC II chromatography (FIG. 23) and desalting, as previously described. Subsequent purification, under SAX-HPLC conditions, showed this sample to be greater than 90% pure (FIG. 24, peak A23/4 at 23.10 min.). However, the proton NMR spectrum of this sample (FIG.

31) shows that a contaminant having a repetitive aliphatic —CH$_2$— moiety is present. It is important to note, nevertheless, that the SAX-HPLC purification; tested positively for inhibition under both in vitro and in vivo bioassay conditions.

Figure 32:
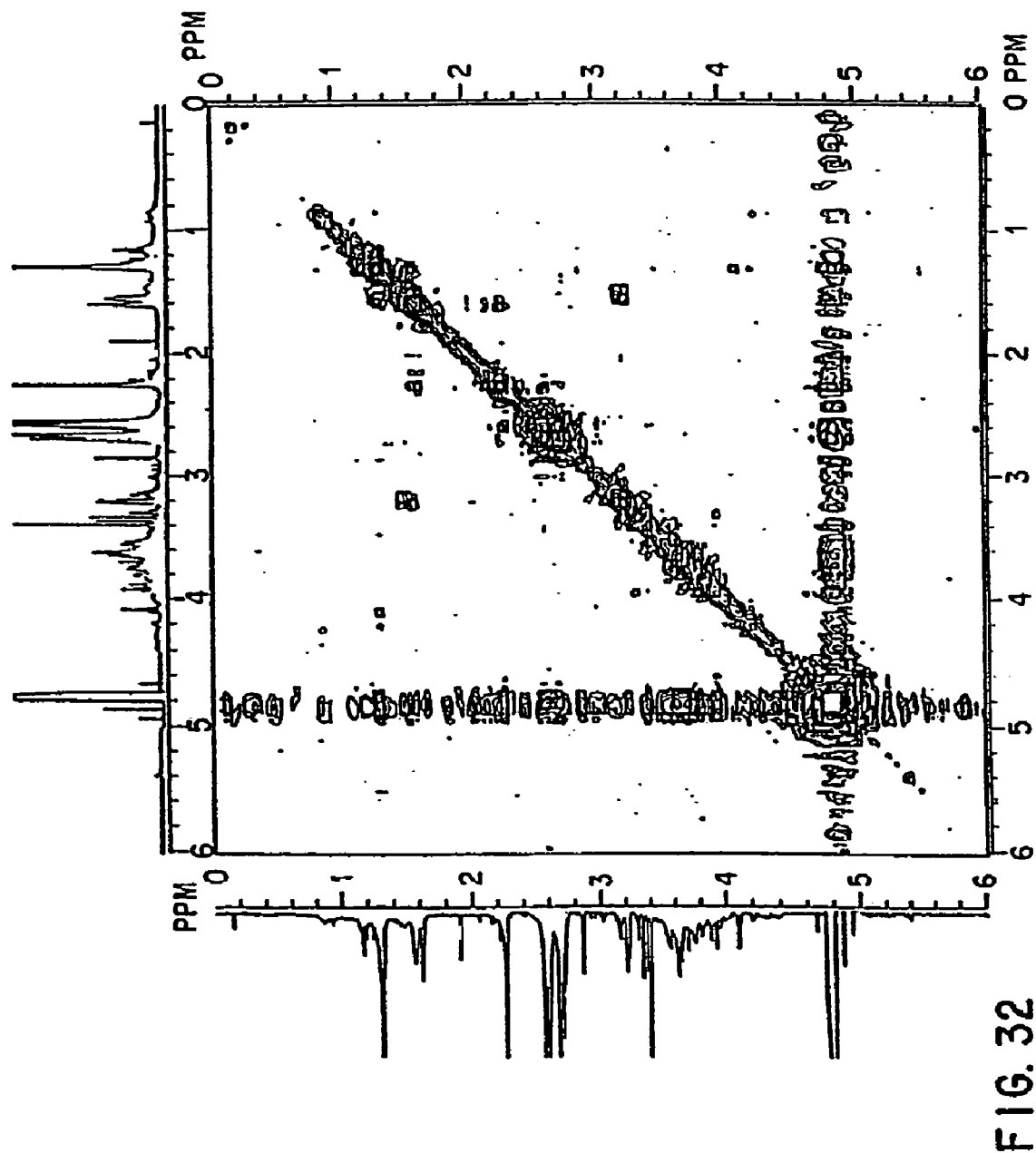
FIG. 32 illustrates a two-dimensional COSY spectrum of the sample of FIG. 31.
Figure 33:
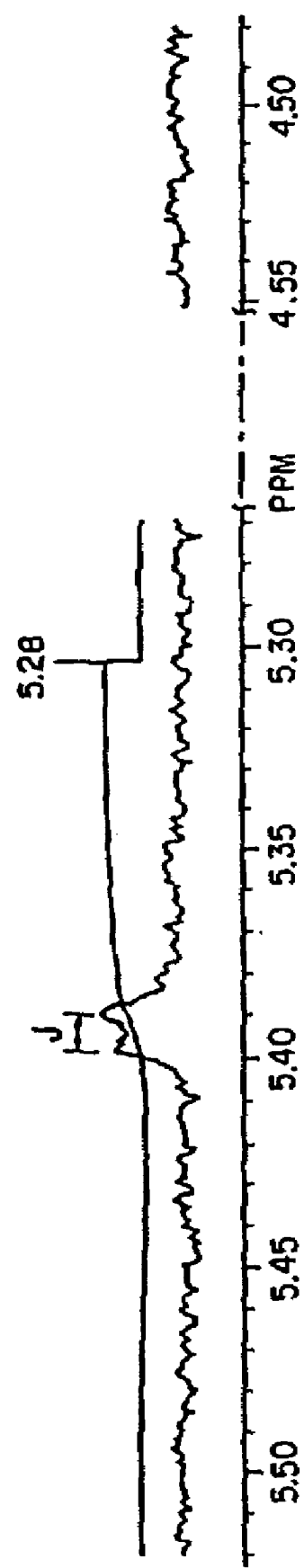
FIG. 33 illustrates an expanded portion of the NMR spectrum of FIG. 31; showing the signal for the anomeric proton.

The proton NMR spectrum was recorded in D$_2$O at 500 MHz at 23° C. A 2-dimensional COSY spectrum was also recorded. The final matrix size was 512×512, N-COSY with presaturation, 1536 scans (FIG. 32). Typical sugar signals are evident between 3-5.5 ppm in both the one dimensional and 2-D spectra. A doublet signal for the anomeric proton is found at 5.39 ppm having a coupling factor of 3 Hertz (FIG. 33), consistent with the presence of a glucosamine sugar unit in an alpha configuration.

The chemical shift of the anomeric proton, together with what is believed to be the beta-glucuronide specificity of placental heparanase, leads to the tentative conclusion that the disaccharide has a glucosamine at the non-reducing end, in an alpha configuration, attached 1→4 to a glucuronic acid residue at the reducing end. Furthermore, the absence of a signal at 6 ppm indicates that the disaccharide is saturated (i.e., there is no double bond at C$_4$-C$_5$ of the glucosamine residue). Thus, the heparanase is not an eliminase but apparently a hydrolase.

Figure 34:
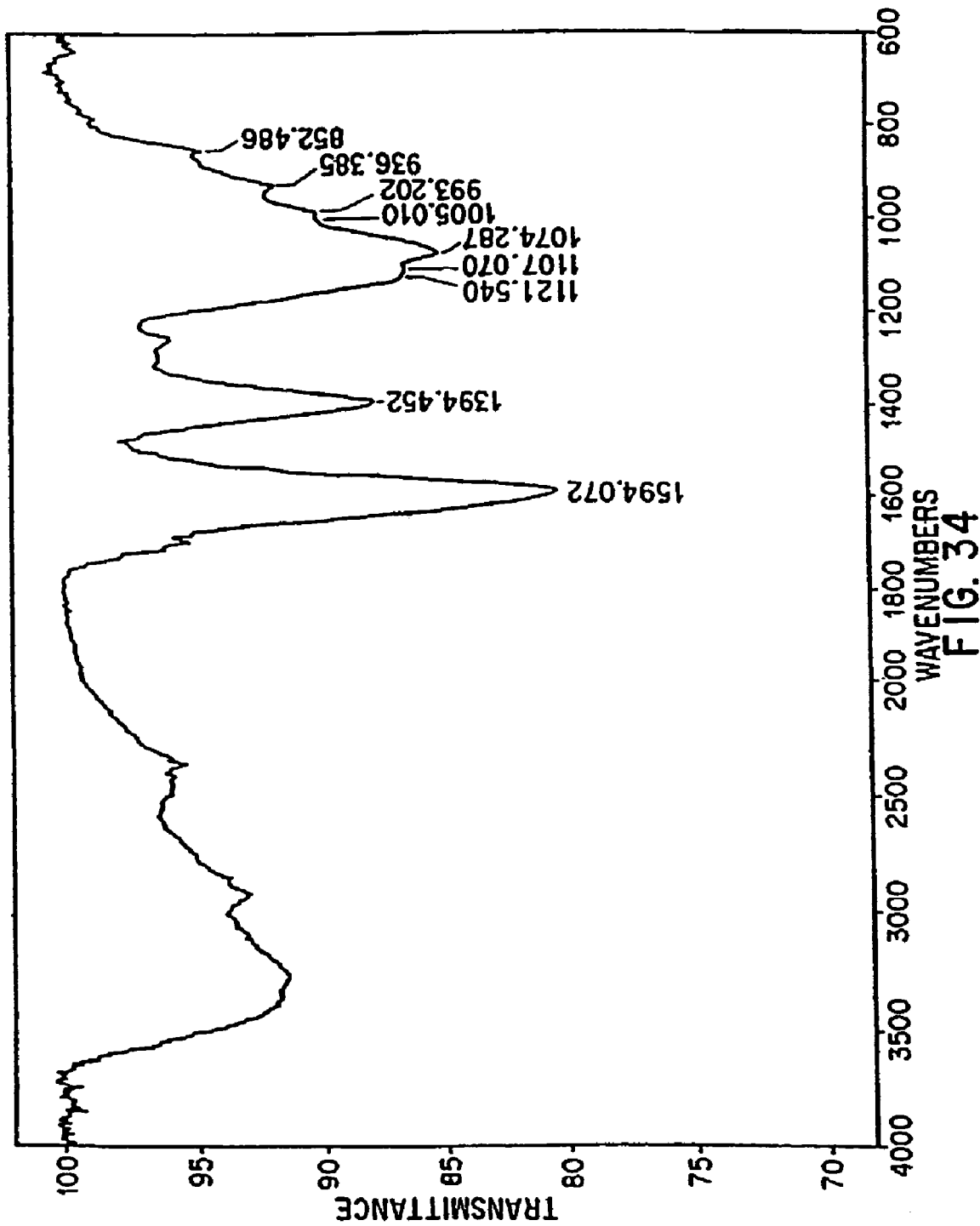
FIGS. 34 and 35 illustrate the FTIR spectra obtained from two separate samples, one indicating the presence of a sulfated compound (FIG. 34) and the other indicating the presence of a partially desulfated analog (FIG. 35).
Figure 35:
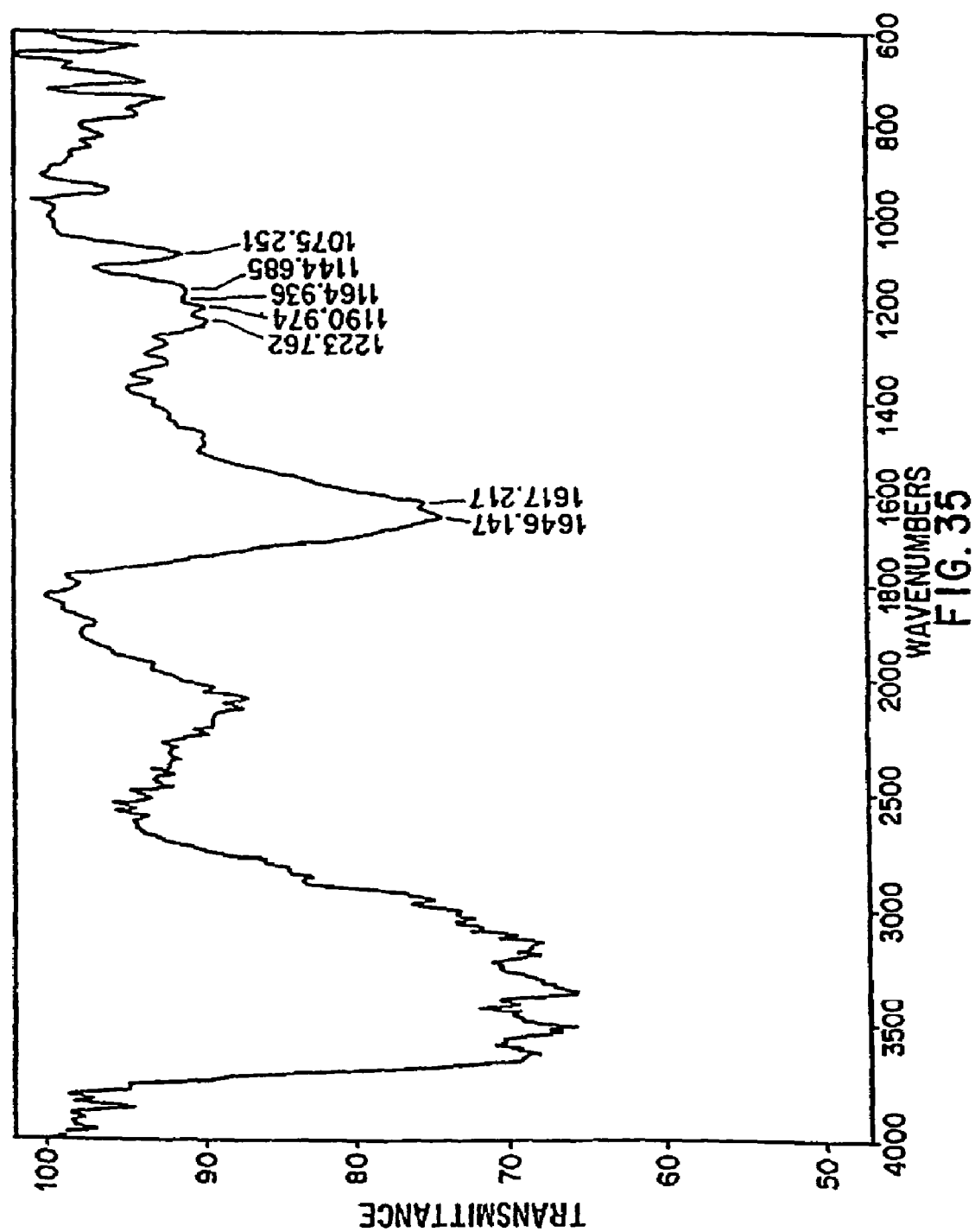

FTIR spectra were recorded on a Mattson Galaxy 6020, equipped with a transmission film detector; DTGS at resolution of 2 cm$^{-1}$; 128 scans using a ZnSe window. FIGS. 34-35 indicate the presence of a sulfated compound and a partially desulfated analog, respectively. FIG. 34, in particular, exhibits absorptions at 3500-3000 (characteristic of carboxyl and hydroxyl groups), 1594 (carbonyl), 1394, 1121, 1107, 1074, 1005, 993, 936, and 852 cm$^{-1}$, at least some of which, particularly the last, are associated with sulfate.

Figure 36A:
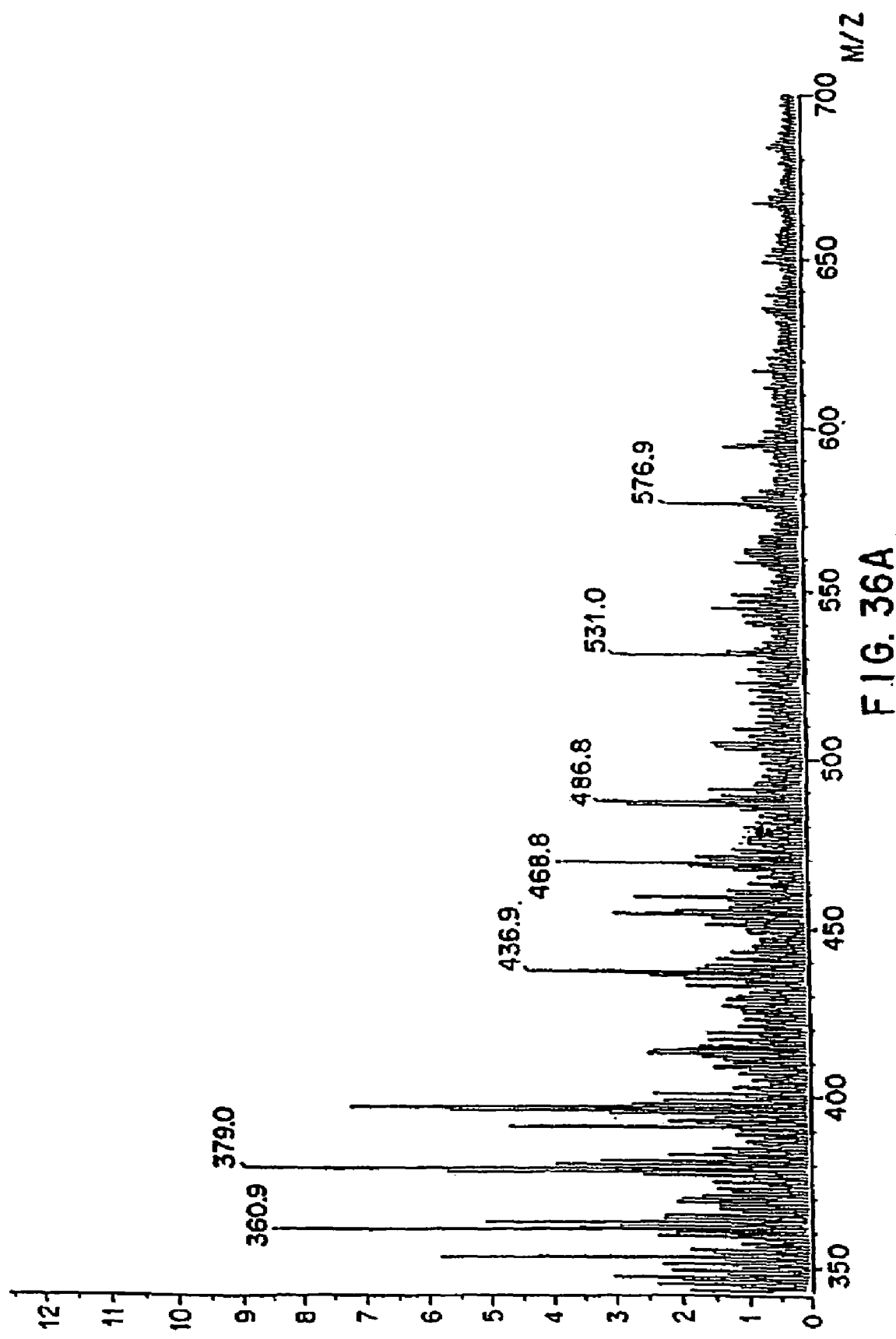
FIG. 36A illustrates the mass spectrum of a methylated derivative of the sample obtained from FIG. 23 in a solvent matrix comprised of DTT:thioglycerol (1:1).
Figure 36B:
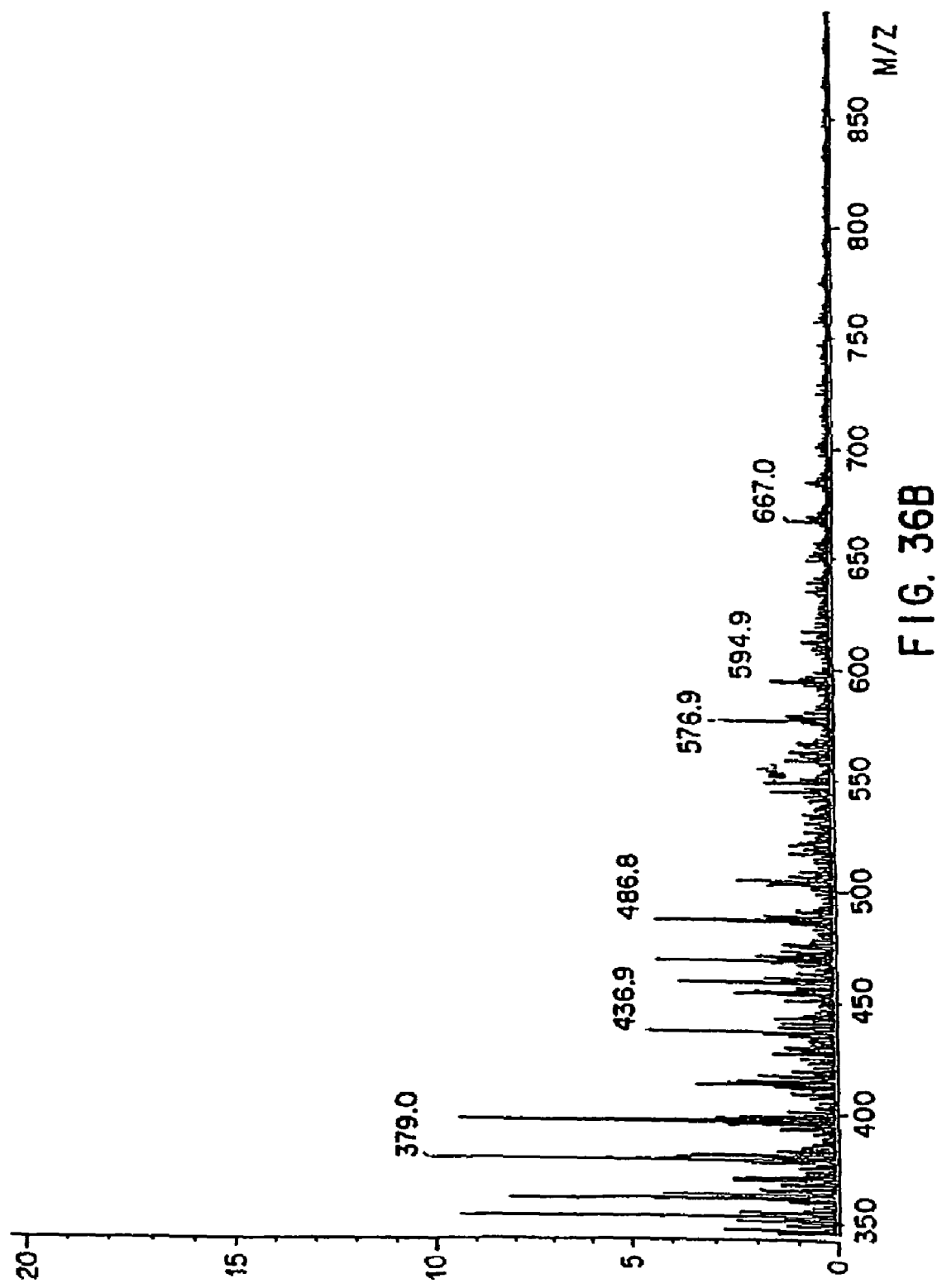
FIG. 36B illustrates the mass spectrum of the solvent matrix only.
Figure 37A:
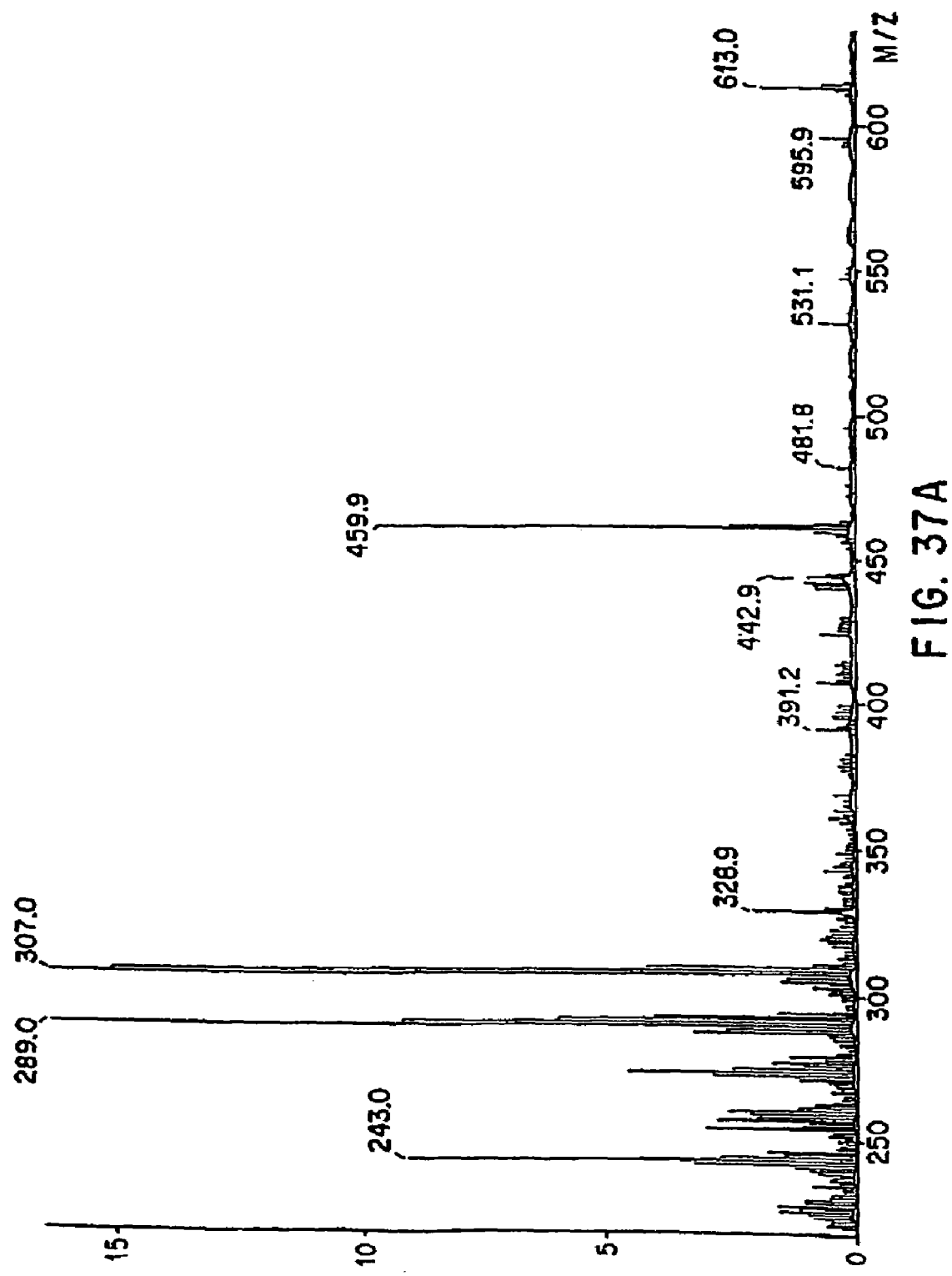
FIGS. 37A and 37B illustrate the mass spectrum of the same sample in a different solvent matrix comprised of methylnitrobenzyl alcohol, FIG. 37A being the mass spectrum of the sample plus the solvent matrix and FIG. 37B being the mass spectrum of the solvent matrix only.
Figure 37B:
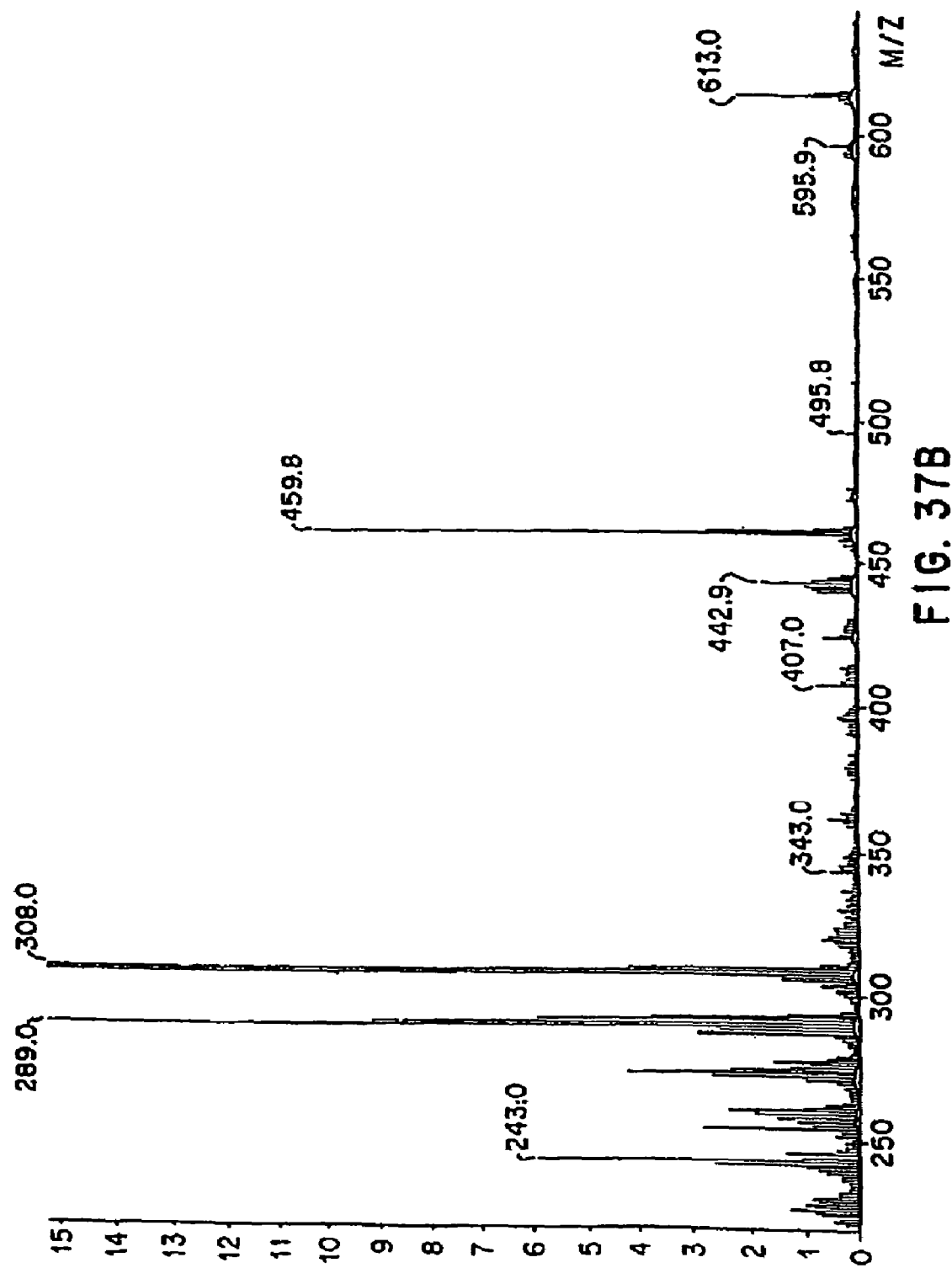

The mass spectrum of a methyl derivative, believed to have lost some sulfate, was obtained on a Jeol JMS HX/110A FAB. Xe beam was used at E=6 kV, emission current=10 mA, acceleration voltage was 10 kV. First, the methyl derivative was prepared by treating a sample of the oligosaccharide with diazomethane in acidic media. The methylated product was next extracted with ethyl acetate. A characteristic ion was observed above the background having M/Z (M+H$^+$)=531. Thus, it is believed that the data are consistent with a molecular weight, for a methylated derivative, of about 530. In order to verify the results, two different matrices were used; DTT:thioglycerol (1:1) and methylnitrobenzyl alcohol (FIGS. 36 A-B and 37 A-B, respectively). The "A" spectra correspond to sample+matrix, whereas the "B" spectra relate to the specific matrix only.

Based on such mass spectral data, a tentative chemical formula for the methylated (partially desulfated) derivative can be proposed: C$_{13}$H$_{23}$NO$_{17}$S$_2$, MW=529.47.

4-O-(2-deoxy-6-O-sulfo-2-sulfoamino-α-D-glucopyranosyl)-(2-O-sulfo-β-D-glucopyranoside) uronic acid is synthesized according to the following protocol.

6.23. Synthesis of 4-O-(2-deoxy-6-O-sulfo-2-sulfoamino-α-D-glucopyranosyl)-(2-O-sulfo-β-D-glucopyranoside) uronic acid 6.23.1. Preparation of 6-O-Acetyl-2-azido-3,5-di-O-benzyl-2-deoxy-β-D-glucopyranosyl chloride 2-O-Tosyl-1,6:3,4-dianhydro-β-D-galactopyranose [2] is prepared from 1,6-anhydro-μ-D-glucopyranose [1], according to Cerny et al. (1961) Coll. Chech. Chem. Cos. 26:2547. 2-O-Tosyl-1,6-anhydro-β-D-glucopyranose [3] is prepared from 2-O-Tosyl-1,6:3,4-dianhydro-β-D-galactopyranose [2] according to Cerny et al. (1965), Coll. Chech. Chem. Soc. 30:1151.

1,6:2,3-dianhydro-β-D-mannopyranose [4] is prepared from 2-O-Tosyl-1,6-anhydro-β-D-glucopyranose [3] according to Stanek and Cerny (1972) SYNTHESIS. p. 698. 6-O-Acetyl-2-azido-3,4-di-O-benzyl-2-deoxy-β-D-glucopyranosyl chloride [A] is prepared from 1,6:2,3-dianhydro-β-D-mannopyranose [4] according to Paulsen and Slenzel (1978) Chem. Ber. 111:2334.

6.23.2. Preparation of Methyl-(benzyl-2-O-acetyl-3-O-benzyl-β and α-L-glucopyranosid)-uronate 1,2:5,6-Di-O-isopropylidene-α-D-glucofuranose [6] is prepared from D-glucose [5] according to Stevens (1978), Methods Carbohydr. Chem. 6:124. 3-O-Benzyl-1,2-O-isopropylidene-α-D-glucofuranose [7] is prepared from 1,2:5,6-Di-O-isopropylidene-α-D-glucofuranose [6] according to Whistler and Lake (1972), Methods Carbohydr. Chem. 6:286.

Methyl-(benzyl-2-O-acetyl-3-O-benzyl-β and α-L-glucopyranosid)-uronate is prepared from 3-O-Benzyl-1,2-O-isopropylidene-D-glucofuranose [7] according to Jacquinet et al. (1984), Carbohydr. Res. 130:221.

6.23.3. Condensation of Products of 6.23.1 and 6.23.2

Figure 43:
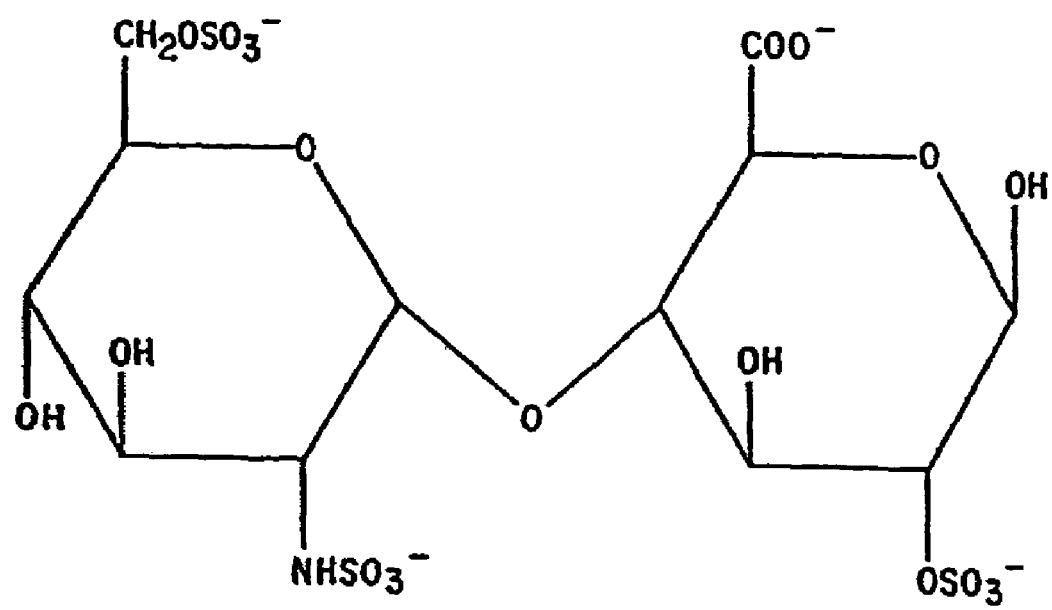
FIG. 43 represents the structure of 4-O-(2-deoxy-6-O-sulfo-2-sulfoamino-α-D-glucopyranosyl)-(2-O-Sulfo-β-D-glucopyranoside) uronic acid, prepared by the synthetic scheme of Example 6.23.

Coupling of the products of Section 6.23.1 and 6.23.2 above is conducted according to Jacquinet et al. (1988), Carbohydr. Res. 174:253. O-deacetylation, hydrolysis, O-Sulfation, reduction, and debenzylation is conducted according to Jacquinet et al. (1984) (supra) to give 4-O-(2-deoxy-6-O-sulfo-2-sulfoamino-α-D-glucopyranosyl)-(2-O-sulfo-β-D-glucopyranoside) uronic acid, which is further purified by SAX-HPLC according to Rice et al. (1985), Anal. Biochem. 150:325. The structure of this product is given in FIG. 43 and it is believed it has the same biological activity as other compounds described herein.

It should be apparent to those skilled in the art that other compositions and methods not specifically disclosed in the instant specification are, nevertheless, contemplated thereby. Such other compositions and methods are considered to be within the scope and spirit of the present invention. Hence, the invention should not be limited by the description of the specific embodiments. disclosed herein but only by the following claims.

The disclosure of all references cited herein are incorporated herein in their entirety by reference.

What is claimed is:

1. A method for treating an inflammatory disease or disorder, comprising administering a pharmaceutically effective amount of a therapeutic agent to a subject in need thereof, said therapeutic agent comprising:
   an N-sulfated 4-deoxy-4-en-iduronoglucosamine containing at least one additional sulfate group or a pharmaceutically acceptable salt thereof, or an N-acetylated 4-deoxy-4-en-iduronoglucosamine containing at least two sulfate groups or a pharmaceutically acceptable salt thereof; and
   a pharmaceutically acceptable carrier.

2. The method of claim 1, wherein said inflammatory disease or disorder is a primary inflammation.

3. the method of claim 1, wherein said disease is a secondary inflammation.

4. The method of claim 1, wherein said therapeutic agent is administered to a subject in need thereof in a dose lower than 5 mg at weekly intervals.

5. The method of claim 1, wherein said inflammatory disease or disorder is uveitis.

6. The method of claim 1, wherein said inflammation is associated with an immune response.

7. The method of claim 6, wherein said inflammatory disease or disorder is an allergy.

8. The method of claim 6, wherein said inflammatory disease or disorder is an autoimmune disease.

9. The method of claim 8, wherein said autoimmune disease is rheumatoid arthritis.

10. The method of claim 8, wherein said autoimmune disease is systemic lupus erythematosis.

11. The method of claim 8, wherein said autoimmune disease is multiple sclerosis.

12. The method of claim 6, wherein said inflammatory disease or disorder is allograft rejection.

13. The method of claim 12, wherein said allograft is an organ transplant.

14. The method of claim 13, wherein said organ is selected from the group comprising: heart, liver, kidney or bone marrow.

15. The method of claim 12, wherein said allograft is a skin graft.

16. The method of claim 1, wherein said inflammatory disease or disorder is arthritis.

17. The method of claim 1, wherein said inflammatory disease or disorder is colitis.

18. The method of claim 1, wherein said inflammatory disease or disorder is psoriasis.

19. The method of claim 6, wherein said therapeutic agent is administered to a subject in need thereof in a dose lower than 5 mg at weekly intervals.

* * * * *